US009663783B2

(12) United States Patent
Freier

(10) Patent No.: US 9,663,783 B2
(45) Date of Patent: May 30, 2017

(54) MODULATION OF ALPHA SYNUCLEIN EXPRESSION

(75) Inventor: Susan M. Freier, San Diego, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 13/988,296

(22) PCT Filed: Nov. 17, 2011

(86) PCT No.: PCT/US2011/061245
§ 371 (c)(1), (2), (4) Date: Sep. 10, 2013

(87) PCT Pub. No.: WO2012/068405
PCT Pub. Date: May 24, 2012

(65) Prior Publication Data

US 2014/0005252 A1 Jan. 2, 2014

Related U.S. Application Data

(60) Provisional application No. 61/414,848, filed on Nov. 17, 2010.

(51) Int. Cl.
*C12N 15/11* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/323* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,102,785 | A | 4/1992 | Livak et al. |
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,833,361 | B2 | 12/2004 | Hong et al. |
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,579,458 | B2 | 8/2009 | Khvorova et al. |
| 7,595,306 | B2 | 9/2009 | Bumcrot |
| 7,750,141 | B2 | 7/2010 | Crooke et al. |
| 8,389,487 | B2 | 3/2013 | Bohn et al. |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2004/0226056 | A1* | 11/2004 | Roch .................. G01N 33/6896 800/12 |
| 2005/0064548 | A1 | 3/2005 | Lindquist et al. |
| 2005/0130923 | A1 | 6/2005 | Bhat et al. |
| 2005/0137155 | A1 | 6/2005 | McSwiggen et al. |
| 2007/0031844 | A1 | 2/2007 | Khvorova et al. |
| 2007/0192879 | A1 | 8/2007 | Yoshimoto et al. |
| 2007/0225209 | A1 | 9/2007 | Roch et al. |
| 2007/0287831 | A1 | 12/2007 | Seth et al. |
| 2008/0003570 | A1 | 1/2008 | Rogers et al. |
| 2008/0039418 | A1* | 2/2008 | Freier ............................. 514/44 |
| 2008/0039618 | A1 | 2/2008 | Allerson et al. |
| 2009/0092981 | A1 | 4/2009 | Swayze et al. |
| 2009/0176729 | A1* | 7/2009 | Tan ...................... C12N 15/113 514/44 R |
| 2010/0204306 | A1 | 8/2010 | Tan |
| 2011/0054005 | A1 | 3/2011 | Naito et al. |
| 2012/0129912 | A1 | 5/2012 | Mouradian et al. |
| 2012/0322991 | A1 | 12/2012 | Montefeltro et al. |
| 2014/0120158 | A1 | 5/2014 | Montefeltro et al. |

FOREIGN PATENT DOCUMENTS

| | | |
|---|---|---|
| WO | WO 03/004602 | 1/2003 |
| WO | WO 2004/106356 | 12/2004 |
| WO | WO 2005/021570 | 3/2005 |
| WO | WO 2007/134181 | 11/2007 |
| WO | WO 2007/135426 | 11/2007 |
| WO | WO 2008/101157 | 8/2008 |
| WO | WO 2008/109509 | 9/2008 |
| WO | WO 2008/150729 | 12/2008 |
| WO | WO 2008/154401 | 12/2008 |
| WO | WO 2009/006478 | 1/2009 |

(Continued)

OTHER PUBLICATIONS

Penn et al, WO 01/57277, Aug. 2001, partial document, pp. 1-105.*
Abeliovich et al., "Mice lacking alpha-synuclein display functional deficits in the nigrostriatal dopamine system." Neuron (2000) 25(1):239-252.
Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.
Altmann et al., "Second-generation antisense oligonucleotides: structure-activity relationships and the design of improved signal-transduction inhibitors" Biochem. Soc. Trans. (1996) 24:630-637.
Altmann et al., "Second Generation of Antisense Oligonucleotides: From Nuclease Resistance to Biological Efficacy in Animals" Chimia (1996) 50(4):168-176.

(Continued)

*Primary Examiner* — Kate Poliakova-Georgantas
(74) *Attorney, Agent, or Firm* — Ionis Pharmaceuticals, Inc. Patent Dept.

(57) ABSTRACT

Disclosed herein are antisense compounds and methods for decreasing alpha-synuclein mRNA and protein expression. Also disclosed herein are methods for treating, preventing, and ameliorating neurodegenerative diseases in an individual in need thereof.

15 Claims, No Drawings

(56) References Cited

FOREIGN PATENT DOCUMENTS

WO WO 2009079399 A2 * 6/2009
WO WO 2011/131693 10/2011
WO WO 2014/064257 5/2014

OTHER PUBLICATIONS

Altmann et al., "Second Generation Antisense Oligonucleotides-Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.
Altschul et al., "Basic Local Alignment Search Tool" J. Mol. Biol. (1990) 215:403-410.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Burre et al., "Alpha-synuclein promotes SNARE-complex assembly in vivo and in vitro." Science (2010) 329(5999): 1663-1667.
Cabin et al., "Synaptic vesicle depletion correlates with attenuated synaptic responses to prolonged repetitive stimulation in mice lacking alpha-synuclein." J. Neurosci. (2002) 22(20):8797-8807.
Chiasson et al., "The application of antisense oligonucleotide technology to the brain: some pitfalls." Cellular and Molecular Neurobiology (1994) 14(5):507-521.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clayton et al., "Synucleins in synaptic plasticity and neurodegenerative disorders" J. Neurosci. (1999) 58(1):120-129.
Conway et al., "Kinetic Stabilization of the α-Synuclein Protofibril by a Dopamine-α-Synuclein Adduct" Science (2001) 294(5545):1346-1349.
Crooke et al., "Basic Principles of Antisense Therapeutics" Antisense Research and Application (1998) Chapter 1:1-50.
Davidson et al., "Stabilization of alpha-synuclein secondary structure upon binding to synthetic membranes." J. Bioi. Chem. (1998) 273(16):9443-9449.
Elayadi et al., "Application of PNA and LNA oligomers to chemotherapy" Curr. Opinions Invens. Drugs (2001) 2:558-561.
Fleming et al., "Early and Progressive Sensorimotor Anomalies in Mice Overexpressing Wild-Type Human α-Synuclein" J. Neurosci. (2004) 24(42):9434-9440.
Fleming et al., "Olfactory deficits in mice overexpressing human wildtype alpha-synuclein." Eur. J. Neurosci. (2008) 28(2):247-256.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al., "Activity of a Novel bcl-2/bcl-xL-Bispecific Antisense Oligonucleotide Against Tumors of Diverse Histologic Origins" Gautschi et al. (2001) 93(6):463-471.
Iwai et al., "The precursor protein of non-A beta component of Alzheimer's disease amyloid is a presynaptic protein of the central nervous system." Neuron (1995) 14(2):467-475.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kramer et al., "Presynaptic -Synuclein Aggregates, Not Lewy Bodies, Cause Neurodegeneration in Dementia with Lewy Bodies" J. Neurosci. (2007) 27(6):1405-1410.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Lee et al., "Membrane-bound α-Synuclein Has a High Aggregation Propensity and the Ability to Seed the Aggregation of the Cytosolic Form" J. Biol. Chem. (2002) 277(1):671-678.
Leumann, "DNA Analogues: From Supramolecular Principles to Biological Properties" Bioorganic & Medicinal Chemistry (2002) 10:841-854.
Lewis et al., "In vivo silencing of alpha-synuclein using naked siRNA" Mol Neurodegener (2008) 3:19.
Maher et al., "Comparative hybrid arrest by tandem antisense oligodeoxyribonucleotides or oligodeoxyribonucleoside methylpbosphonates in a cell-free system" Nucl. Acids. Res. (1988) 16(8):3341-3358.
Marti et al., "Clinical Overview of the Synucleinopathies" Movement Disorders (2003) 18(6):S21-S27.
Martin, "Ein neuer Zugang zu 2'-O-Alkylribonucleosiden und Eigenschaften deren Oligonucleotide" Helv. Chim. Acta (1995) 78:486-504.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Reynolds et al., "Rational siRNA design for RNA interference" Nature Biotechnology (2004) 22(3):326-330.
Rockenstein et al., "Differential neuropathological alterations in transgenic mice expressing alpha-synuclein from the platelet-derived growth factor and Thy-1 promoters." J. Neurosci. Res. (2002) 68(5):568-578.
Sanghvi et al., "Heterocyclic Base Modifications in Nucleic Acids and Their Applications in Antisense Oligonucleotides" Antisense Research and Applications (1993) pp. 273-288.
Schulz-Schaeffer, "The synaptic pathology of α-synuclein aggregation in dementia with Lewy bodies, Parkinson's disease and Parkinson's disease dementia" Acta Neuropathologica (2010) 120(2):131-143.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Souza et al., "Chaperone-like activity of synucleins." FEBS Lett. (2000) 474(1):116-119.
Srivastava et al., "Five- and Six-Membered Conformationally Locked 2',4'-Carbocyclic riboThymidines: Synthesis, Structure, and Biochemical Studies" J. Am. Chem. Soc. (2007) 129(26): 8362-8379.
Uversky, "Neuropathology, biochemistry, and biophysics of alpha-synuclein aggregation." J. Neurochem. (2007) 103(1): 17-37.
Wahlestedt et al., "Potent and nontoxic antisense oligonucleotides containing locked nucleic acids" PNAS (2000) 97:5633-5638.
Woolf et al., "Specificity of antisense oligonucleotides in vivo" PNAS (1992) 89:7305-7309.
Yoshida, "Multiple system atrophy: alpha-synuclein and neuronal degeneration." Neuropathology (2007) 27(5):484-493.
Zhang et al., "PowerBLAST: A New Network Blast Application for Interactive or Automated Sequence Analysis and Annotation" Genome Res. (1997) 7:649-656.
Zhou e al., "Fine Tuning of Electrostatics around the Internucleotidic Phosphate through Incorporation of Modified 2',4'-Carhocyclic-LNAs and -ENAs Leads to Significant Modulation of Antisense Properties" J. Org. Chem. (2009) 74:118-134.
International Search Report for application PCT/US11/61245 dated May 18, 2012.
Chen et al., "RNA interference targeting a-synuclein attenuates methamphetamine-induced neurotoxicity in SH-SY5Y cells" Brain Research (2013) 1521: 59-67.

(56) References Cited

OTHER PUBLICATIONS

Fountaine et al., "RNA Interference-Mediated Knockdown of a-Synuclein Protects Human Dopaminergic Neuroblastoma Cells From MPP+ Toxicity and Reduces Dopamine Transport" Journal of Neuroscience Research (2007) 85:351-363.
Gorbatyuk et al., "In Vivo RNAi-Mediated α-Synuclein Silencing Induces Nigrostriatal Degeneration" Mol. Ther. (2010) 18(8): 1450-1457.
Liu et al., "a-Synuclein produces a long-lasting increase in neurotransmitter release" The EMBO Journal (2004) 23:4506-4516.
McCormack et al., "a-Synuclein Suppression by Targeted Small Interfering RNA in the Primate Substantia Nigra" PLoS One (2010) 5(8):e12122.
Murphy et al., "Synucleins Are Developmentally Expressed, and a-Synuclein Regulates the Size of the Presynaptic Vesicular Pool in Primary Hippocampal Neurons" The Journal of Neuroscience (2000) 20(9):3214-3220.
Sapru et al., "Silencing of human α-synuclein in vitro and in rat brain using lentiviral-mediated RNAi" Exp. Neurol. (2006) 198:382-390.
Monti et al., "Alpha-synuclein protects cerebellar granule neurons against 6-hydroxydopamine-induced death" J. of Neurochemistry (2007) 103:518-530.
European Search Report for application EP 11840796.4 dated Dec. 4, 2014.
GenBank Accession No. NM_000345.3, retrieved online on Jan. 25, 2016.

* cited by examiner

SEQUENCE LISTING

<160> NUMBER OF SEQ ID NOS: 143

<210> SEQ ID NO 1
<211> LENGTH: 3215
<212> TYPE: DNA
<213> ORGANISM: Homo sapiens

<400> SEQUENCE: 1

```
aggagaagga gaaggaggag gactaggagg aggaggacgg cgacgaccag aaggggccca     60

agagaggggg cgagcgaccg agcgccgcga cgcggaagtg aggtgcgtgc gggctgcagc    120

gcagaccccg gcccggcccc tccgagagcg tcctgggcgc tccctcacgc cttgccttca    180

agccttctgc ctttccaccc tcgtgagcgg agaactggga gtggccattc gacgacagtg    240

tggtgtaaag gaattcatta gccatggatg tattcatgaa aggactttca aaggccaagg    300

agggagttgt ggctgctgct gagaaaacca aacagggtgt ggcagaagca gcaggaaaga    360

caaaagaggg tgttctctat gtaggctcca aaaccaagga gggagtggtg catggtgtgg    420

caacagtggc tgagaagacc aaagagcaag tgacaaatgt tggaggagca gtggtgacgg    480

gtgtgacagc agtagcccag aagacagtgg agggagcagg gagcattgca gcagccactg    540

gctttgtcaa aaaggaccag ttgggcaaga atgaagaagg agccccacag gaaggaattc    600

tggaagatat gcctgtggat cctgacaatg aggcttatga aatgccttct gaggaagggt    660

atcaagacta cgaacctgaa gcctaagaaa tatctttgct cccagtttct tgagatctgc    720

tgacagatgt tccatcctgt acaagtgctc agttccaatg tgcccagtca tgacatttct    780

caaagttttt acagtgtatc tcgaagtctt ccatcagcag tgattgaagt atctgtacct    840

gcccccactc agcatttcgg tgcttccctt tcactgaagt gaatacatgg tagcagggtc    900

tttgtgtgct gtggattttg tggcttcaat ctacgatgtt aaaacaaatt aaaaacacct    960

aagtgactac cacttatttc taaatcctca ctattttttt gttgctgttg ttcagaagtt   1020

gttagtgatt tgctatcata tattataaga tttttaggtg tcttttaatg atactgtcta   1080

agaataatga cgtattgtga aatttgttaa tatatataat acttaaaaat atgtgagcat   1140

gaaactatgc acctataaat actaaatatg aaattttacc attttgcgat gtgttttatt   1200

cacttgtgtt tgtatataaa tggtgagaat taaaataaaa cgttatctca ttgcaaaaat   1260

attttatttt tatcccatct cactttaata ataaaaatca tgcttataag caacatgaat   1320

taagaactga cacaaaggac aaaaatataa agttattaat agccatttga agaaggagga   1380

attttagaag aggtagagaa aatggaacat taaccctaca ctcggaattc cctgaagcaa   1440

cactgccaga agtgtgtttt ggtatgcact ggttccttaa gtggctgtga ttaattattg   1500

aaagtggggt gttgaagacc ccaactacta ttgtagagtg gtctatttct cccttcaatc   1560

ctgtcaatgt ttgctttacg tattttgggg aactgttgtt tgatgtgtat gtgtttataa   1620

ttgttataca tttttaattg agccttttat taacatatat tgttattttt gtctcgaaat   1680

aattttttag ttaaaatcta ttttgtctga tattggtgtg aatgctgtac ctttctgaca   1740

ataaataata ttcgaccatg aataaaaaaa aaaaaaaagt gggttcccgg gaactaagca   1800

gtgtagaaga tgattttgac tacaccctcc ttagagagcc ataagacaca ttagcacata   1860

ttagcacatt caaggctctg agagaatgtg gttaactttg tttaactcag cattcctcac   1920

ttttttttt taatcatcag aaattctctc tctctctctc tctttttctc tcgctctctt   1980

ttttttttt tttttacagg aaatgccttt aaacatcgtt ggaactacca gagtcacctt   2040

aaaggagatc aattctctag actgataaaa atttcatggc ctcctttaaa tgttgccaaa   2100
```

```
tatatgaatt ctaggatttt tccttaggaa aggtttttct ctttcaggga agatctatta   2160
actccccatg ggtgctgaaa ataaacttga tggtgaaaaa ctctgtataa attaatttaa   2220
aaattatttg gtttctcttt ttaattattc tggggcatag tcatttctaa aagtcactag   2280
tagaaagtat aatttcaaga cagaatattc tagacatgct agcagtttat atgtattcat   2340
gagtaatgtg atatatattg ggcgctggtg aggaaggaag gaggaatgag tgactataag   2400
gatggttacc atagaaactt cctttttttac ctaattgaag agagactact acagagtgct   2460
aagctgcatg tgtcatctta cactagagag aaatggtaag tttcttgttt tatttaagtt   2520
atgtttaagc aaggaaagga tttgttattg aacagtatat ttcaggaagg ttagaaagtg   2580
gcggttagga tatattttaa atctacctaa agcagcatat tttaaaaatt taaaagtatt   2640
ggtattaaat taagaaatag aggacagaac tagactgata gcagtgacct agaacaattt   2700
gagattagga aagttgtgac catgaattta aggatttatg tggatacaaa ttctccttta   2760
aagtgtttct tcccttaata tttatctgac ggtaattttt gagcagtgaa ttactttata   2820
tatcttaata gtttatttgg gaccaaacac ttaaacaaaa agttctttaa gtcatataag   2880
ccttttcagg aagcttgtct catattcact cccgagacat tcacctgcca agtggcctga   2940
ggatcaatcc agtcctaggt ttattttgca gacttacatt ctcccaagtt attcagcctc   3000
atatgactcc acggtcggct ttaccaaaac agttcagagt gcactttggc acacaattgg   3060
gaacagaaca atctaatgtg tggtttggta ttccaagtgg ggtctttttc agaatctctg   3120
cactagtgtg agatgcaaac atgtttcctc atctttctgg cttatccagt atgtagctat   3180
ttgtgacata ataaatatat acatatatga aaata                             3215
```

<210> SEQ ID NO 2
<211> LENGTH: 115001
<212> TYPE: DNA
<213> ORGANISM: Homo sapiens

<400> SEQUENCE: 2

```
agaatcatct aatgatattg tggttatttt taaacagtcc ttaaattttg tggatgcata     60
ctgaatgttt acagctgaaa agatatatat aaagcttgaa tttggtaaaa aaaaaaaaaa    120
aagagggagg attggtagtg ataaagtgag tggacttatg gatgagacat gatcagccat    180
gcattgaaaa aatgtaaaag ttggatgatc ttcacatgag agtcctttat tctgtctact    240
tttgcatatg tttgaatatt tcccataaca aaaagttgaa aatagagtga tcacatgagt    300
taatctccta atttacaaaa aagaaaactg gaaacagaag gagaacaaaa cttgttcaag    360
gtctcaaagc cagacagcaa actagctccc aagtccaacc ttcttgctct ggtcctaagc    420
aaacaaaaaa tattaatatg agctactgca ttaaggaaag tctgcttttc caaagggcag    480
accaatagtt caaggaagag tttaaataat aaatatttgt gatcttactt tcatgctttt    540
ctattttcca ctgaacacat atgcattatc ttctatatgt cttttatgta taatcatttg    600
cttcctgttc cttgtggttt taaagttgtt ttgtatgttt aaatttgatt ttactcaaat    660
ttcagaaccc aaattagcgc aagaatcaga caaagcataa ctttctataa atataaaaac    720
aattaaaaaa aaaacataca gcaaaaacga gttgttgttt ccccccctcct cttccagtgc    780
ttaactaatc ttccgaatcc aggcacagaa agcaaaggct ttctgctagt gggaggagct    840
tgcttctcca ttctggtgtg atccaggaac agctgtcttc cagctctgaa agaggtgaaa    900
atgtgttaag cgatgcaaaa attgtcttga agttcgcgtg tgtatgtctg tgtgcatgtg    960
```

-continued

```
cgtgtggtgg gtggggggag agaaaagggg gtgtcaattc tgagggcaac gagaatcaga   1020
agtcagaaag gtgagtggtg tgtagcatct ccctttcaga aggggctgaa gaagaaattg   1080
gatatgatgg tccggtaggc taaatcacgc tggatttgtc tcccagataa agggaggtct   1140
gcaaagtaag tcccatttct agagcgaaaa gccttaggac cgcttgtttt agacggctgg   1200
ggaatattta ttccttgttc cactgatggg aaaatcagcg tctggcaggc gctgattggt   1260
ggaaaggaaa atggtgatag tggcgtggaa agaggatttg ctgagccttc tcctgcctcc   1320
tcaacctgtg actcttcctt agtagtctcc ctttcaccct caggaccctt tccggctctt   1380
cctagattaa gagcaaacga aaaccttgaa gatatttgaa ctaaagcgac ccctaacgtt   1440
gtaacctgtg accgtgatta aatttcagcg atgcgagggc aaagcgctct cggcggtgcg   1500
gtgtgagcca cctcccggcg ctgcctgtct cctccagcag ctccccaagg gataggctct   1560
gcccttggtg gtcgaccctc aggccctcgg ctctcccagg gcgactctga cgaggggtag   1620
ggggtggtcc ccgggaggac ccagaggaaa ggcggggaca agaagggagg ggaaggggaa   1680
agaggaagag gcatcatccc tagcccaacc gctcccgatc tccacaagag tgctcgtgac   1740
cctaaactta acgtgaggcg caaaagcgcc cccactttcc cgccttgcgc ggccaggcag   1800
gcggctggag ttgatggctc accccgcgcc ccctgcccca tccccatccg agatagggac   1860
gaggagcacg ctgcagggaa agcagcgagc gccgggagag gggcgggcag aagcgctgac   1920
aaatcagcgg tgggggcgga gagccgagga gaaggagaag gaggaggact aggaggagga   1980
ggacggcgac gaccagaagg ggcccaagag agggggcgag cgaccgagcg ccgcgacgcg   2040
gaagtgaggt gcgtgcgggc tgcagcgcag accccggccc ggcccctccg agagcgtcct   2100
gggcgctccc tcacgccttg ccttcaagcc ttctgccttt ccaccctcgt gagcggagaa   2160
ctgggagtgg ccattcgacg acaggttagc gggtttgcct cccactcccc cagcctcgcg   2220
tcgccggctc acagcggcct cctctgggga cagtcccccc cgggtgccgc ctccgccctt   2280
cctgtgcgct ccttttcctt cttctttcct attaaatatt atttgggaat tgtttaaatt   2340
tttttttaa aaaaagagag aggcggggag gagtcggagt tgtggagaag cagagggact   2400
caggtaagta cctgtggatc taaacgggcg tctttggaaa tcctggagaa cgccggatgg   2460
gagacgaatg gtcgtgggca ccgggagggg gtggtgctgc catgaggacc cgctgggcca   2520
ggtctctggg aggtgagtac ttgtcccttt ggggagccta aggaaagaga cttgacctgg   2580
ctttcgtcct gcttctgata ttcccttctc cacaagggct gagagattag gctgcttctc   2640
cgggatccgc ttttccccgg gaaacgcgag gatgctccat ggagcgtgag catccaactt   2700
ttctctcaca taaaatctgt ctgcccgctc tcttggtttt tctctgtaaa gtaagcaagc   2760
tgcgtttggc aaataatgaa atggaagtgc aaggaggcca agtcaacagg tggtaacggg   2820
ttaacaagtg ctggcgcggg gtccgctagg gtggaggctg agaacgcccc ctcgggtggc   2880
tggcgcgggg ttggagacgg cccgcgagtg tgagcggcgc ctgctcaggg tagatagctg   2940
agggcggggg tggatgttgg atggattaga accatcacac ttgggcctgc tgtttgcctg   3000
agtttgaacc acaccccgag tgagcagtta gttctgttgc ctacgccttt ccaccatcaa   3060
cctgttagcc ttcttctggg attcatgtta aggatacccc tgaccctaag cctccagctt   3120
ccatgcttct aactcatact gttacccttt agaccccggg aatttaaaaa aggggttaat   3180
cttttcatgc aactccactt ctgaaatgca gtaataacaa ctcagaggat tcatcctaat   3240
ccgtggttag gtggctagac ttttactagc caagatggat gggagatgct aaatttttaa   3300
tgccagagct aaaaatgtct gctttgtcca atggttaaat gagtgtacac ttaaaagagt   3360
```

-continued

```
ctcacacttt ggagggtttc tcatgatttt tcagtgtttt ttgtttattt ttccccgaaa   3420
gttctcattc aaagtgtatt ttatgttttc cagtgtggtg taaaggaatt cattagccat   3480
ggatgtattc atgaaaggac tttcaaaggc caaggaggga gttgtggctg ctgctgagaa   3540
aaccaaacag ggtgtggcag aagcagcagg aaagacaaaa gagggtgttc tctatgtagg   3600
taggtaaacc ccaaatgtca gtttggtgct tgttcatgag tgatgggtta ggataatcaa   3660
tactctaaat gctggtagtt ctctctcttg attcattttt gcatcattgc ttgtcaaaaa   3720
ggtggactga gtcagaggta tgtgtaggta ggtgaatgtg aacgtgtgta tttgagctaa   3780
tagtaaaaaa tgcgactgtt tgcttttcca gatttttaat tttgccctaa tatttatgac   3840
tttttaaaaa tgaatgtttc tgtacctaca taattctatt tcagagaaca gttttaaaaa   3900
ctcatagtct tttaaaaaat aatcaagaat attcttaaga atcaaaatca ttgatggatc   3960
tgtgatttct tttaccatca tgaaaaatgt ttgtcaattt taatccattc tgatttttaa   4020
aatatgactt tgatatgccc ctgtgatgtg tataaagaga cctatttgtg gccctaaaat   4080
ggaaagaaca gattagtctt tgatagagtt acttcatgtg atcatttggt ctctgtgaac   4140
actgaggaca gagaaaagtg cttgagggct gctactaatc tctcagaaac atttgtatag   4200
ttcatccatc aaatgacaca catactaaaa gaataaagaa attgatgctt attacctact   4260
tgttcctaaa gttccacctt ggggtataca cccaaactct gactctcttt tctgtaactt   4320
gaactgtatt caattgagtg ttattttaca aaccactttg aattccttgg aaaagaatag   4380
acacacactc tcatccacag gcatagacac acacactcaa cacagacaca ttgcccattc   4440
ttcctctctt ctttctcctc tgagcttttt cacattctct ggtggcaact atagcagtaa   4500
gagtcacagg atgaacagtc aggtggagga tgaccacatt gagttgccta gctgaaacat   4560
gtgctccgtc tatgtctgca aagtgaaaga aagctacact atctcttcaa catagatcag   4620
tgggggaaat tttatacttg ggatgattta tatgaatgca tctcatcaaa gttcacaaca   4680
catttttttt tcagtttttt attttcagtt tttagagtca gggccttgct ctgtcgccca   4740
ggctggactg cagtgatgct atcatagctc actgcatcct tgaattcctg ggctcaagtc   4800
atgcccccac ctcagcctcc tgagtagcca ggattatagg catgtgccac tgcctcatta   4860
tttagacttt tcttatgttg acttaatctt cccacaaatc ttcaattaaa ttactttttt   4920
tctaccttaa aacatatttt cagaaagtca ttgaaatagg gtgttacaag aggaaaaaat   4980
tgatgagtta attttaaata ttttatgaag tgtgaattat acctttttag atggaatttg   5040
gaatactgaa tcagtgacat gcagtttatc aatatctttc cgtttgtcct cagatttcca   5100
agttctgcaa gcacaagttt ctttgactta gttacctttt aactgttcat tgaaatcatt   5160
ttcaatgtct ctcatggcat ttaacacata gcacattcta taaatttttt attggttaca   5220
ttctgagttc taattgagag ttgaacttac acacagaatt taagataaaa aatgaccatg   5280
tgaagacaca atagtatagt ccagggattg gcaaaatttt gggtaaggaa tcagatagca   5340
cgtattttaa gccatgagat ctatgtcttg gccaggtgcc gtggctcagg tctttaatcc   5400
cagcactttg agagcccgag gctggtggat cacttgagcc caggggtttg agaccagcct   5460
gggccacatg gtgaaaccct gtgtctacaa acaacgcaaa aattagccgg gtatggtagc   5520
atgcatgtgt attgccagct acccaggagg ctgaggtagg aggatggctt gagccataca   5580
gctcactgca gaggttgcag tgagctgaga tcgagccact gcactccagc ctgggtggca   5640
gagtgatacc ctgtctaaaa aaaagaaaaa aaaatctatg tctcaattct gctgttgaag   5700
```

-continued

```
tgtgaaggta gtcataaaca ataactagtg tggctgtgtc ccaataaaac ttcatttatc   5760
aaaacaggtg gtgggctgga attgtcttgt atgttgtagc ttgctgacta ctgatagagt   5820
ggaaagaaca tgcactaatc acacaaacca aagttttagt tgagactaca tcacttatca   5880
cctttagggt cttggggaag cgtacttaac atctctgagc atcacttccc tgattagtaa   5940
aaaatatgat ttagaaaact gcaactacct tgcagttttt gtgggaatgt cataataaga   6000
caggacatat gaataattga gcacactttt atatatagga accatggtta ttattatcaa   6060
ataaactctc caacggaata attactttgc caacacgttt tccatttatt cttttatcct   6120
tcattacata actagtttga aagattggag gcgaccaaag accattttat aatttcactt   6180
atggctgaag atgtttggta gaagcctcat aagaaaagta atctcattcc tttataagaa   6240
tatactttta acaactactt tttaactcat tgaagaacta ccttaatgat cagtgttatt   6300
tttatgggtt ttgttccctc catttttgtt atctgcgtac accaatttc aatcaacata   6360
cttcaattta atagacaaaa atttcttcaa atgactcaga aattaattag atctaaatcc   6420
aaaagcagaa agatttaatt atctttatat aatgctcagt aatataaatg caataaatac   6480
aagaaaatga tgatctttga gtgtcttcca atgccactct gctcaataag cagcagtggc   6540
catcagtgaa attgatagca aattctcaag tcaaaatgtg cttcacctca ctaagctgac   6600
aaagtcaaca taacatgcac aacagggata actgagttct caaaactctc aggtattact   6660
tctgaccttc ttctccactc tgtgctcttt tgaggttggg aagacaagat agggtgtgtg   6720
tgggacacct ccgctcaggg aagccatcag ctctggtgtc cctacagcat ttataccttg   6780
ctagtcacat aaccacttgg cacctatttt gtaggtgtac gttatcaatt acagattact   6840
cataaattaa aggctaacca tcaattacag attattagta aataattatg acctcaaaga   6900
acaactgatt ggtttgatac atggtaacct tatgaggact ctcatttatc tcgttttttt   6960
aagttatata cctatctctt tggggttgca ctacaaaaat ataaaatatg ttgcataaga   7020
tatttataaa aaataattaa ttataagttc taatggtgtg gtttagtggc attctttttt   7080
ttttcttttt ttctgagata gggtctcaat ctgtcatttc actccaggct gaagtgcagt   7140
ggtgtgatct cggctcactg caacctccgc ctcctgggtt caagttattc tcctgactca   7200
gcctcctgag tagctgaaat tacaggcatg caccaccatg cccggctaat ttttgtattt   7260
ttagtagaga tggggtttca ccatgttagc caggatggtc tcgaactcct gatctcatca   7320
tccccgacct cggcctccca aaatgctggg attacaggcg tgagccattg cacccggcct   7380
agtggcattc ttttttaaaa ataaatttaa ttgtgtatat ttagggtatg caacatgatg   7440
ctatcagata cattagacac taaaaaatta ctatattgaa gcaaattaat atattcataa   7500
tctctcatag ttaccttttt tgttgttttt gtggcaaggg cagctaaaat ccacttattt   7560
atcatgaatc tcaaatatag tacaatttta tcacctacag tcctcataca ttagatctgt   7620
acacttttc atcttacaca tctgctactt gcttggatcc tatggcctat atgtccctat   7680
tttctaccta cttttccacc cctattaacc ctgtttttta cgtagtctct gtatatttga   7740
attttgtttc aagcttccac atatatgtga gataatgtaa tatttttctt tctgtgtttg   7800
gcttatttca cttagcataa ttttgtctgg gttcatccat gttgtaaatg gtaggatctt   7860
gttttttag ggctgactga tattccattg tatctatgta ccacaatctt tttatctacc   7920
tatctatcag tagacacttt agttgtggct attatgtttt tcttttttc tttttggag   7980
acagggtctt gctgtcaccc aggctgcaat ggagtggtgt tatcatagct cactgtaacc   8040
tcaaacttct gggctcaaga gatcctcctg ccttggcctc ccaagtagct gagactacag   8100
```

gcatacatta ccatgcctgg ctaattttta atattttttg tagatatagc atctcactct 8160
gttgcccaga ctggtctcaa actcctaatt caaatttaga atagagtatg acaattctgt 8220
aaaatataaa aaacatgtcc actccgtata ggaagttata caatgagaag aagacaaaca 8280
ctatttacat tactcttgat aagtttttta caaagaaata aaacacttta atttctaatg 8340
ttttaaattc tggtttgcta aataaataaa tattagtttt agtgttttta aaattcctta 8400
tatagttata agtgatcttc ctgcctcagc ctcccaaagc actgggattc caagcaagag 8460
ccactgtgtt ggggcccttg gaaacagata tgctgaaatc ttttcttgtg gatctacacc 8520
cagaagaggg attgctgggt catatgctac tctattttta atttttcttt tatttttagt 8580
gaatatgtaa taattgtata taattgtggg atccagaatt atatttccat acatgtatac 8640
aatgtgtgat aatcaaatta gggtaattaa catatccatt acctgaaaca tttatcattc 8700
ctttgtggtg ggaacagtaa aaattaaaaa ttctctcttc tagatttttg aacatatgca 8760
ataaactatt gttaagtata tcaccctaca gtactacaga atgctagaac tcattcctca 8820
tatttggctc caatttcata ttctttaacc aacctctcca tatcctcccc tccctcttac 8880
cgttgtcagc ctctaataat cataattcta ctctctactt ctatctcatt gtctttgatt 8940
tagaatatgt ttcataattt aaccaaaggt caaattctta ggtactgcta aggcaaagaa 9000
caaagatcgc attccagctg ttagacattt cttactacta gtcattttta agacaacatg 9060
gggtgcaggt ggtgaggatg agagatagag attgaaacat attctcttaa atatcagctg 9120
ttctcactct gcatagttcc agcacaaaca aattccaggt actatggtta gttaaataac 9180
accagccact aacaacacaa ttcaaatttc tgttaccaca gtataccgaa agtcattgca 9240
taaagtacaa actttgctgc taactcttca gccttcaaat cattacataa ataacagaaa 9300
cccattataa tcagtgacaa aaccacagca cttctttcaa agctttttgg agattggttg 9360
cttcacatct gttatgcagt tcatacagac agcaatgccc ggacttgtgt ggccacattg 9420
tctcccagtg gtgagcccat gtgatgtttc acgaaaatgc gcaatcaaaa gaggaaactg 9480
gccagcaaag atgaaagagt agcaaacaaa ggaagtgaaa cattctggaa gtaaaatttg 9540
aatcaaacat aagttgatgt atacaggaag tagctaccct gaggatgttg tcactgctgc 9600
aattcaggag actctaaata tgcagtcaga ggaacgtagt gaggtgaagg tatccgtata 9660
atggggaaag aggttgtgat aaagagtgaa ggtgtcccag aggaagtgtt gctgaaaaat 9720
acaccttatg ttaaatacac tgtcagtata tcatgacatt aaagtgcaaa tgataacatt 9780
ttgtaaactg atccaaactt aaaaaggagt atgataattc tgtaaaacat aaaaatcatg 9840
ccgattccat aaattataca gtgtgaatta cactgaaaaa tccaacatta gagaggatat 9900
gaatacaatt ttttacaagc ataattttaa taatacacat aataattatt tgtattcaag 9960
tttagtaatg ttcaaggttt ggaagaaatt ctgatcctgt gtagagaccc tagtttgaat 10020
gtgcttatag cctattatta catgtgtaat gttacataaa ttacttaact cggattttta 10080
atttcatcag ctatttaaaa tgggcataat ataactatat taaatggctg ttatgaagat 10140
taaataagat gatatgtaaa atgtgttttt tgtttgtttg tttgtttgtc tgtttgtttt 10200
tttgagacag agtcttgctc tgttacccag gctggagtgc agtggcacaa tcttggctca 10260
ctgcaagttc tgcctcccga gttcatgcca ttctcctgcc tcagcccctc ccaagtagct 10320
gggactacag gcacccgcca ccacgcctgg ctaatttttt gtatttttgg tagagatggg 10380
gtttcaccat attagccagg atggtctcga tctcctgacc tcgtgatctg cccacctcgg 10440

-continued

```
cctcccaaat tgctgggatt acaggcatga gccactgcgc ccagcctaaa atgttttttt  10500
tacataatgg gtgttcagca catgttaaag ccttctctcc atccttcttc ccttttgttt  10560
catgggttga ctgatctgtc tctagtgctg tacttttaaa gcttctacag ttctgaattc  10620
aaaattatct tctcactggg ccccggtgtt atctcattct tttttctcct ctgtaagttg  10680
acatgtgatg tgggaacaaa ggggataaag tcattatttt gtgctaaaat cgtaattgga  10740
gaggacctcc tgttagctgg gctttcttct atttattgtg gtggttactg gagttccttc  10800
ttctagtttt aggatatata tatatatttt tttctttccc tgaagatata ataatatata  10860
tacttctgaa gattgagatt tttaaattag ttgtattgaa aactagctaa tcagcaattt  10920
aaggctagct tgagacttat gtcttgaatt tgtttttgta ggctccaaaa ccaaggaggg  10980
agtggtgcat ggtgtggcaa caggtaagct ccattgtgct tatatccaaa gatgatattt  11040
aaagtatcta gtgattagtg tggcccagta ttcaagattc ctatgaaatt gtaaaacaat  11100
cactgagcat tctaagaaca tatcagtctt attgaaactg aattctttat aaagtatttt  11160
taaataggta aatattgatt ataaataaaa aatatacttg ccaagaataa tgagggcttt  11220
gaattgataa gctatgttta atttatagta agtgggcatt taaatattct gaccaaaaat  11280
gtattgacaa actgctgaca aaaataaaat gtgaatattg ccataatttt aaaaaaagta  11340
aaatttctgt tgattacagt aaaatatttt gaccttaaat tatgttgatt acaatattcc  11400
tttgataatt cagagtgcat ttcaggaaac acccttggac agtcagtaaa atgtttattg  11460
tatttatctt tgtattgtta tggtatagct atttgtacaa atattattgt gcaattatta  11520
catttctgat tatattattc atttggccta aatttaccga gaatttgaac aagtcaatta  11580
ggtttacaat caagaaatat caaaaatgat gaaaaggatg ataatcatca tcagatgttg  11640
aggaagatga ggatgagagt gccagaaata gagaaatcaa aggagaacca aaatttaaca  11700
aattaaaagc ccacagactt gctgtaatta agttttctgt tgtaagtact ccacgtttcc  11760
tggcagatgt ggtgaagcaa aagatataat cagaaatata atttatataa tcggaaagca  11820
ttaaacacaa tagtgcctat acaaataaaa tgttcctatc actgacttct aaaatggaaa  11880
tgaggacaat gatatgggaa tcttaataca gtgttgtgga tatgactaaa aacacaggag  11940
tcagatcttc ttggttcaac ttcctgctta ctccttacca gctgtgtgtt ttttgcaaga  12000
ttcttcacct ctgtgtgatt tagcttcctc atctataaaa taattcagtg aattaatgta  12060
cacaaaacat ctggaaaaca aaagcaaaca atatgtattt tataagtgtt acttatagtt  12120
ttatagtgaa ctttcttgtg caacattttt acaactagtg gagaaaaata tttctttaaa  12180
tgaatacttt tgatttaaaa atcagagtgt aaaaataaaa cagactcctt tgaaactagt  12240
tctgttagaa gttaattgtg cacctttaat gggctctgtt gcaatccaac agagaagtag  12300
ttaagtaagt ggactatgat gccttctagg gacctcctat aaatatgata ttgtgaagca  12360
tgattataat aagaactaga taacagacag gtggagactc cactatctga agacggtcaa  12420
cctagatgaa tggtgttcca tttagtagtt gaggaagaac ccatgaggtt tagaaagcag  12480
acaagcatgt ggcaagttct ggagtcagtg gtaaaaatta aagaacccaa ctattactgt  12540
cacctgatga tctaatggag actgtggaga tgggctgcat ttttttagtc ttttccagaa  12600
tgccaaaatg taaacacata tctgtgtgtg tgtgtgtgtg tgtgtgtgtg tgcgtgtgtg  12660
tgagagagag agagagactg aagtttgtac aattagacat tttataaaat gttttctgaa  12720
ggacagtggc tcacaatctt aagtttctaa cattgtacaa tgttgggaga ctttgtatac  12780
tttattttct ctttagcgta ttaaggaatc tgagatgtcc tacagtaaag aaatttgcat  12840
```

```
tacatagtta aaatcagggt tattcaaact ttttgattat tgaaaacttt cttcattagt  12900
tactagggtt gaatgaaact agtgttccac agaaaactat gggaaatgtt gctaggcagt  12960
aaggacatgg tgatttcagc atgtgcaata tttacagcga ttgcacccat ggaccaccct  13020
ggcagtagtg aaataaccaa aaatgctgtc ataactagta tggctatgag aaacacattg  13080
ggataaatcg gctgctatca taatcattcc tctcccacat cagataaatg aattaacttt  13140
ttgaataggg ttatttaata taaagtgctt aagtctaatt atgagaagaa ataagataat  13200
tacacttcaa tggttaaaga gagggagaat aatttgcata ttatgcctga tgtaaaatgt  13260
ttattatggg tacatattaa gtgctaacta attgttaatt gttcttgcta caagtcttaa  13320
tgcagggaaa caagaaatta ttacatagta cctaatatta tcttctaata ttaaagaaac  13380
aatttcccct aaattcatcc cattagcttt tttttttcg gtggggcagg ggagaaatac  13440
agacttcagt aaacttgggc tgggaacttt ctacctacaa agttcaaata aaataaatta  13500
tcctagttag ataatatcaa tgaaaaatcc accaacttaa atcctggctg tttgatctca  13560
ggaaattatt tcagttatca acttaatgca tcatattata gaaatatatg aaaatgtgtt  13620
taattaaact tactgaatga tatgtttttt caggtacttt aaaaataaac tatgatataa  13680
agttacctat ttttcatgca agtatagtat aaagaaattt ctaacactgg agattttctg  13740
aaggttttga ttcttataaa tttattacat cataatgaac aaaactaatt ttcaacatat  13800
tatgatttaa atttccttag taaattgttt caaatttatt ttctttaaat ccatatttac  13860
atatgtatat ttaaatatac atatttactt gtataacaat tcaaaaccat atattaattt  13920
tataattttg tttaatgtca aaggttagat ttggctatat ctattctaaa agttggtatc  13980
acatttcctt tttggaattt tatttttaaa gtagctaaag tcaaatataa acctattatt  14040
tatattaatg cagacattag aggtagacac taaattcatt ttagtatatt ctaaattatt  14100
tattatctac tatgaaataa tataaagaaa aataaagcag aatccctgat ttcaaagaac  14160
tcaattgccg aaaaacagtt accatttatt agacccaaaa tgtactaata tgagtgtgtc  14220
tcttttcctt ttgttttgtc acccgtcatt tggaatgtca gtgagtagag agatagtgtg  14280
aaaggccctc aaggggaaaa atagaggtta aaggtcagca gagaccctac tagagaaatc  14340
agttctacag aaatgttttt aaatgtgtcg attattgcta catgtacact ctgtcatttt  14400
gtaatgtagc cattttattt atgattataa taataaaaca acaaaattat aataatgtgt  14460
agagtacatt ttactgtgca gtgtattgca ttaaaactag attaaaattt atacatatat  14520
aaaaggctat ctagatatta taaaatttat ggctggatct gtaaaaaatt caaaacctat  14580
ttttaatctc gctttgagat tttataacaa gaaaatgttc gtttcaagca aaattttcaa  14640
ttcacgtcct tgaaaaggaa aaaaatgaca acttgaaaca cataattgac tatttttaaa  14700
ggatcaacat ttcagaaatg ttttaaaaca taagattttc agtacagctt ttcgctggca  14760
tttaaatcga actttgaatt gtaaatagct cttgctctta aggagacatc agccatatcc  14820
ttagaagtgg cacggagttg ttaggtagtt gtacaaaatt ctagcctaaa agacaaatag  14880
ggagcaacac tactgtggac cgtttctggt cttgggctgt gtggctatgt caggcttgcc  14940
cacattgcct gtactaagga gaaagcctct tgtccttaca gacccccttta gcttacatag  15000
tctatttgaa aacaaattgc tttgtccaca ccatttaaat attggcttca ggccaggcgc  15060
ggtggctcac gcctgttatc ccagcacttt gggaggctga ggcgggcaga tcacgaggtc  15120
aggagatcga gaccatcctg gctaacacgg tgaaaccctg tctctactaa aaatataaaa  15180
```

-continued

```
aaattagccg ggtgtggtgg cgcgcacctg tagtcccagc tgctggggag gctgaggcag  15240
gagaatggcc tgaacccggg agtcggagtt tgcagtgagc cgacatcgtg ccactgcact  15300
ccagcctggg tgacagagca agactccgtc tcaaaataaa taaataaata aataaataag  15360
taaatattgg cttcttcaac tggtgagatg aaacctatac aatagtcatg tgaatagcac  15420
taaacagctg acatggtgta actcctctca gactgaggct tatctgggga gtacaaagca  15480
tgtcaagaaa atgtgccttc atttccttag atgagtgtcc ccatcctcca ctctcctcca  15540
ctgttctcct ctctgcttct atgatatcaa cttttctttt tctttagatt ccacatgagt  15600
gagatcatgt ggttgtttgc ctttctgttt ctggcttatt taactgaaca agaaagtttt  15660
tgacatgaaa ttaaacttct gcttgtaaac tcaattcaaa ctatttacac tgtcttctca  15720
aaaatgttaa cttattttaa taaatctact gaatgaccgt atctcatttt gttttatgaa  15780
aagaaattgt aagggtgctc aatagcctct tcattttcat actgtctagc tcctgtgctc  15840
ctattaaaat tactgcaaat ttagcttttt aagaaccctt tgtttcacta cctgaagttc  15900
tataaaaaga tccaagttcc ttcacaaccg tttcttatgc tgttattcgt acatatgtga  15960
taataccacg tctgaacacg tagataataa gtaggggctg ggtgcggtgg atcatgccta  16020
taatcctagc actttgggag gctaaggcgg gtggatcacc tgaggttagg agttcgagac  16080
cggcctggcc aacatgatga aaccctgttt ctactaaaaa tacaaataat aataataata  16140
ataattagcc aggtgtggtt gtgggcacct gtaatcccag ctactcggga gactgaggca  16200
ggagaatagc ttgaactcag gaggcggagg ttgctgtgag ctgagattgt gccattgcat  16260
tccagcctga acaacaagaa tgaaactcca tctcaaataa ataaataaat agaagtatgt  16320
attgtgttgc ttagaaggtg tggtggaaat taacttgctg agtgagatca aaggattggc  16380
actgaattga aataaagaaa tattcatgct gagtctggtt caaatataac tgcacctgta  16440
agaattgctt tctgtaaact ttccatagta taaaccaaat ccaaatcact catggcttta  16500
cattcctgat cgttaaactt gaagcacttt ttaatactgc atgactttag ccaaaatatc  16560
ttagccaaga ttcaatgttt ggttgaacca cactcacttg gacatcttgg tggcttttgt  16620
ttcttctgac cactcagtta tctatggcat gtgtagatac aggtgtatgg aagccgatgg  16680
ctagtggaag tggaatgatt ttaagtcact gttattctac caccctttaa tctgttgttg  16740
ctctttattt gtaccagtgg ctgagaagac caaagagcaa gtgacaaatg ttggaggagc  16800
agtggtgacg ggtgtgacag cagtagccca gaagacagtg gagggagcag ggagcattgc  16860
agcagccact ggctttgtca aaaaggacca gttgggcaag gtatggctgt gtacgttttg  16920
tgttacattt ataagctggt gagattacgg ttcattttca tgtgaggcct ggaggcagga  16980
gcaagatact tactgtgggg aacggctacc tgaccctccc cttgtgaaaa agtgctacct  17040
ttatattggt cttgcttgtt tcaggcatta acccagataa atgccatgca aattttataa  17100
ttattatgat tgtttcaatt tctggaagaa agttaatgaa acaaaaaatg tagtaaaatg  17160
ccaaaggaac agtgacattt cagaaagaat gagggctttc atgttaattg taagtcttgg  17220
aatttctctt ccttggagta acaaatccct ttgtgcctaa tttcctaatt tccaaaataa  17280
agttctttta cttatttctt tatagtgaca tcatctctta ttaaatggca tatctgcata  17340
ttacataaca gttcattgcc aaatacatat ttgtgggaaa tgagagactt aaaatacata  17400
ccaaccagag atatagtttt gaggtagatt ttaaaattct gagaagaatt ttgactgaat  17460
ttttttgaca aacatgggac acgaataaga ttataccaaa gatattataa ctttcatttt  17520
aaatatggaa ctaatacagt atgaggtgtc aacaacgttg aagtttcaca aacatcacca  17580
```

ctacaacagc aaaataattt ttgctttttc cctgccacaa tgacctcctt gctatttctt 17640
gaataaatca agcataccct tgccctgaca cgttcttggg gaggcctgcc ctaatctata 17700
taaaattgga gccattcttc tcacctctgg tattcccagt ctccctactt tttttccttc 17760
tttctttctt tttctttttc tttctttctt tccttctttc tctctttcct ttctttcttt 17820
tcccttcctt ccttcctttc tcccttcctt ccttcctccc tctctccctc ccttccttcc 17880
tccctttctt tctttctctt ttttctttct tgcttccttc cttccttctt tccttttctt 17940
tctttttcct ttctttgcca aagtgttatt cacctttaaa tataatacat aatgtgctta 18000
ctttaatgta tgatttttat tttatttctc ccttctagaa tgtaggcacc atgagagtga 18060
aatatattta ttttgttcat tgatatttca caagtgtctg ggagagtttc caacttacag 18120
tagacaatta acaaacattt attaaattaa ggagggaagg aagtgagtaa gcacaacaac 18180
tttcatttct gggtctttta taatcatatg cttagtataa gaacagtgct attcagctat 18240
ccaaaagtta caatcaaaat gattttggat gaatatcttg aaaattgtga gaaagaagtt 18300
ttatttgctg gcaaactatt ctgggttgtt tccacttcat gtaatcctaa gtagcagcct 18360
taccttgata gcccattaaa actctgataa taaaaaggca gaacaaaaat atctgtgata 18420
tatttagatt tactacatgt acttacatgt ctagtgtctg gtgcaatgga tgctaatgat 18480
ggcaaatcct tactgggctt ctagtgaagt tcttcagcta atgtttgaat gcatggttgg 18540
tcatggtggt accccttttgt acaaaatatg cttttcaaat aatcttatta gggataataa 18600
ttatattaat tcctggtttc catctaaaat tttaattcta tttatagctt cgtaagattt 18660
cacaagttaa gagggacctc agattaaatt agtacacagg caattaatca gttttgtgtc 18720
tccgaccctt ttcacgggct aatagaagct atagaccctc ttagcttcag aaaaatgcgc 18780
actcacatac gcacatcaaa gagcttaatg ggaagtccat tgacagaccc tctgttcaga 18840
tcaatcttct gattgtagag atgaggaaac agaaatctac agaggaagtg ggtagtccaa 18900
gattgcacag tcatttggaa tagactggac accagtagta cttttccagc cactatatca 18960
cttccccaag cacttcctca aaacttacct tcctttgggt ctttatacat tcagttatgg 19020
acaactagat ttaactagag gattttattg cttcagaata ttaagcaaca gggaaacatg 19080
taccgtcttt tattcacctg catttaaggc atacaatata aattgcaaat ggagcatgaa 19140
agtgcttaat cttttacaaa actgggtttg ctttccaccc atctaaaaat acttctattt 19200
attttaatat ttaaagcaga aatctaagtg atgtgacaaa attaatcatt tggagatatt 19260
tcccttatag gtagtatagt ttcttactga tttctaatat gaaaatgaag ccatagaacc 19320
tagaaattgc agcatagttg tggaaataaa cattggactg agagtgaaaa tggctagtct 19380
tcctctctgc tcatacacca cctgactgga taacctttcg cagatctcct aaaagtcttt 19440
ctcataaaat gaggaagctc tactagaaaa ttgttgaagt ctaatttagc aataaagttc 19500
tgagtttcta taataattca aagaatactc taataaatgt ctgcaattgt ggtcacatct 19560
atgggatgct aaaaaatctg gatggtttca atgaaagtat ttaatttgtt cattatgaac 19620
tttgaaataa tttatttcat tttttaaact ttgatcaaaa tgaccctggt aaatagaaat 19680
aagcaaactc tttttgcttg aaatgcttat taatgactgc attgagacac tcattcatca 19740
ttcaagaaag aatgtttgct cacactgtgc cagaaacttg gaggaagagg gatgtgacaa 19800
gtaggggtac tggatgtcta gcttgtagaa gtggattaat ggctctgctt ttaagatcag 19860
gaacactgaa agggagtaat ggcaccggtt ttcacctttc atgccctttg agggtatctg 19920

-continued

```
gtccatcacc ctctagttga tgagggaggg aaagttccct ctcccttcac aaataggtgg  19980
aaattaaatg acataattct gaacaaccaa taaatcgaga gtaaatcaaa gcagatacct  20040
gttttgttaa tttgatcata tgaatgtagc tgcccttagt aataatttct aagtataaga  20100
ctagttaaag gacaaatgag ttatcttgaa ttataagatt ttgttttaca gaacaatatt  20160
aactcttgtg tttagtacat tagaataata gatcttttga tccatatttt tactcatgtg  20220
cacataagaa gttatcagtc atacaattca tttcttgaag ttcatacctt tcattggcag  20280
agtagaaaca ggttaaaagt gcacaggcag aaattttaag tgcaaagcaa cagtgatgtt  20340
atatagagaa aatttatatt tcctacttct attgaagaag aaagatctgc ttgttctaag  20400
aatattgtac aaagaaagtg acttgaatca gcgttattct gtaatgctac tatgcgtgca  20460
gtgtggagta gccactagaa cacttggtct atcccagctc ctcaacagtg tcttgcttgt  20520
ggctggtgct caaataaatc cttgctgaac taatgagcat ctctttcatg ccacatggaa  20580
tgctctaaaa gagttggatc ctgaagtttt tatatttttg taattttctg gagttttaga  20640
gagcaaaagt cctgaataaa ctgtgaagcc actgcctgac aaataataca gcagtcagct  20700
tcgttatcat atcccattga gacacgactt atctacatga tgattaatag ttttcacgca  20760
agaaataagc ttgaaatgtc tgttgccttg gatacttaaa acatccaggt tcagcgatgt  20820
tatttattgt tgttcaaaat cagaatgaag ttcctaagca atgccatttt ggaaaaatta  20880
catcaatata ttatgaacaa cttttttttaa atcttgattt caaatggatt gacacgtgta  20940
tattctgtaa taatcctgac ttaattcata aaaggatagc tagccagttg tgtgctagat  21000
gaataaaaaa aaagcaggtt ttaaaatgtc aggtttgaca ttgtgaatat aatatctaag  21060
tatcctttta ctcatttcct ttgacttact atggctgtca tgttgggctt catgaaaatt  21120
tatttttaaa cacttgagtg ttatggaccc tctgattaaa tgattaatca gatgatgtat  21180
gttgccatca gctgaatcat ttaatgttga tttcacaaac aagcacaggt cacaggcaac  21240
atttcagatt tctttgaaga agcacacaca ggtcacaggc ataatcttaa aataatttta  21300
taacaaggta gtaataagag atgtcaggac tggagaaata ttttaattta tagtaagctt  21360
tccccttaag tgtctaataa ttgttaatat aatacattgc ctcaaataat taaaagtttg  21420
gttcttgtcc ttgtgcttga cttcagaaga taaccagatg actattaggt atatttagac  21480
ctaaattaaa agctttgaga cacaatgaat tgcctgattt gtatttgtgt ttcgagtggc  21540
atatactatt actggcacta taatcttaga ttaaagcata ctgtgattat taaagaaaaa  21600
tttaagattg atttgtttct aaaggtatgt aacagtgaca ttttgcaatg tggtatgtaa  21660
aagttggtat ttctcactca tatgagagcc cactaatggt acataaactg tccccactta  21720
gaaacacaat tattatggcc tttctttgta tctgacaaaa tttcactggg ttcaagatgg  21780
atgaatagtg aattctaatg acccttaatc ctgtaaggtt ctaggtggga aagtactctg  21840
taattatgta taaaattata aggaaaatag gcttactgct atgttttcat taaaaatcat  21900
taactgagta cttaatatgt gccagacact cagctgggca ccatgagaaa tacaaaactg  21960
agtaacatat gggtggctcc tgccttcaag aaatgggcag ttcaggccgg gagactgaca  22020
tatttaccct gggaaaaagg gagcagctgt ggtctctgag aacaatatgg tttgttacaa  22080
gtatatatcc atcatggaaa aaaagagatt tatcttagaa atgagagagg ctgatgctct  22140
caataaatat catacattaa attgtgtttt tgtcagtaga ctgaaattac ctcacataca  22200
cgcacagata gtagccatga tattttagct gcttagatat agagacaaat acttccaccc  22260
aaatcttagg atcagtggtt aatagtctgt aagcattaca atcccacaac atatgcatga  22320
```

ctatacatcc aattttaata ttcaaagaac tgattgcgat gatagttttg tttgtcaaag 22380
aaatgtatta taggatgagt gggatagaac tgcatcacgt tacaccaaca aataggttta 22440
aatcatattt gtgcacttcc cttgttcctt cataaatgtt taacatagct taaaattctg 22500
tggactgcaa cgtgagagca atgaccacac ttctgtgaac ccatttttac tgtgcatgtg 22560
ctaacgtcta ttgttagtat tccttcactt gcaaagatgg catgataatt ttgctggttt 22620
cattaatgag atactgttaa atgtaggatg acttcaaact tagttgtatt gtaaaattat 22680
ttttaattgt atacatttaa gttgtacagc atgatgtttt gagatactta tctttattta 22740
tatatatata taatatacac acgtatataa aagtgattcc tacattgaag caaattaaca 22800
tacccatcat catatggtta tctttgcttt tttactatca gtgcctaaaa tctactttct 22860
tgaaaaatta ccagtatgca ctacaatatt attaacaata atcttcatgt tgtacattag 22920
atctttagac ttactcatct tacatgactt aggtttgttt ttacctctac taccatctga 22980
gccatatttc cactttgtaa tttgataata aacttggaaa aatagcactt atatgtttag 23040
gtgacgggca taaataggat aagatgtgtt tatatattat tccatatatc ttgtctccaa 23100
ctacaatgat aaacaacctg tttgtcccta aaaagtaaga aataacttga cttttctgcc 23160
ccttcaagca taggctgtta gcttttaagt tttagggaga cattgatgat gctatttgct 23220
ttatcaagag gaaattgtca aaagaggtct tttggttctc aaactattca aagtatttaa 23280
aaatcaggac aaaatatgtt tacgtgatat tcaagggtac agaaatgagg taaatgagat 23340
gccaattgta tttgtcatgc aaatatataa ttacgtgtat gagagttaga tgatacatct 23400
catcaattta attgttcttc tacaaggaga aaatgaacaa tttgtcaact cgtatatgaa 23460
gtaattttta taagaaattt tattaaaact tttaacaaca tttggatttt taagttgcaa 23520
tttaaatatc cccttctacc aggtgattct ggaatcacta agcagttact tgtgaaaatt 23580
ccaaagtagc atttaattct tattaatgtc atagtgaata ctaatgcaaa gaatactgag 23640
ccagaaatta tgcttgttga ataaatagat tatttattga acaagtaagt gaaaaaaatgg 23700
aaataaagaa cggatatata ttttatcttc ctgcttagat gtgggactgt cctacttttc 23760
tctggtgttc acaacaacaa tatgataaat ctaattggaa ttcagttcat aggaatgaat 23820
tcagttacat tatggattgt gatgaataat gtacactttt aatttaatga aatcaaatag 23880
attttaacta tctatgctta caatggggtg acataagtct gacaatcctt aatatcaagt 23940
catctccaat tcacatgtat acacactttt tttctatttg gctattggga atcctcacaa 24000
aaatcgaaaa ttgccctttc agtgtacgtt acggtatttc atgccacaca gattttctga 24060
ggttgtacat acagctttgc cttgaggttc caatttttgc tcagtggatt gagtatatat 24120
tatttgctat atatcagaag aggcatgtgc ttcctactta tgtcaggtaa ctttgggatt 24180
aatataattg tcctacaaag catagataga tagaaatact tcatccttaa tttctaatat 24240
tatgacatat ctaaagtagg cacctttaaa agttaatctc cactaaatac taatgactgc 24300
ttatagtggc aattcatctt tcatggtagt cctcctacaa aggtatacta acatttatga 24360
gtttgaaaca aaggcaattc acaagtgttc tgctagagat ggtctatatc tgctgtttga 24420
tccagcatga tggccagctg gccctcctgt gcatgacggc tcgtggttta actgcaccat 24480
tttgtttggt catatacagg gaaaacatgg catggtgtgg agggcatggg cttgaattca 24540
gggaacagag agttggtctt ctctctctca ctctactgga tgatgtcatc tcccctctct 24600
aagcatgagt tttcttatct gtgaaataaa aatgttgaat taaatgagtt caaaatgctt 24660

-continued tcagtctgtg tttaatagct tgaatcttaa gacaatgtat tcaattatgc gttgccagat 24720
ccctggcaac tcatgtaacc tttctaaacc atagctactc atctgtaact ggccagccaa 24780
ctgcccaggg ttggagtgtg aatgaaataa gataatgcag acaaaagatt tttaaaaatt 24840
gtagtgcatt atacagttgt aatattttgc caagaactta cattttctct aagaagtgtg 24900
tcgatacatg atcacagaaa atcttttcca tattcctttg tagtttgatg atattaagta 24960
agtaaattgt ataacacaaa gagggaaaag catcactgaa catgccgttt tatttagcta 25020
aataaaatgt aatcactatt agttttcctc tgatttcccc aaagtcatgt gattccattg 25080
agtattatgc acatggtata attagaatgg attctctgct caaataattt tgggaaacat 25140
ttaaattaac aaagtttaaa agtatctctg ttaagctgaa gcaaatctca aaggccttaa 25200
tattgtatgt aagaggaata gttaccatct ttcctaatgc ctctttgacg ccaaacccat 25260
ggagaatagt tctaggtgtt cagtaaaaca cagatttggg atgccacagg ttaattggaa 25320
ctgtcccctg caatcctttt ctctttttct taataatggc tgattgcagg tcctagatga 25380
aagacattta gagagattat caggactcag catcccatat cagaatccat tcttttatag 25440
tcattttctg ttacatttct tgggacaaca ccaaagaaat gaccatcttc attcacatag 25500
gctttgtacc aaatgctgac aaagatcctt ggtgacctag atgggggcag gtctaagtag 25560
attgcagctg taaaattggc tgatgaatga tctcagcccc ttttactcac actcaaaggc 25620
aggacagtcc attaagggga aggagggcag agtttttcct taggccaatt ccctatgcca 25680
gaacttttta gaatggaagc atttccagag gagaaacaac cccaagcaca gttcaaagcc 25740
ccctcctccc aagttcattt gaaagtggga tggtttatct gcaaaggggg aaaagatgag 25800
ggatagggac gggaatatcc ctacccttca gagagtctgg tttcatcctg cacttttact 25860
gcacagccac aaatgccttg gggtgaatct acaatatgat acatcatatg gtctaaacgt 25920
gcctggctga tcctctctaa tacttcaggg gtctaaaagg gataacatgc tctcctgtta 25980
ctcaccgact ctgtccgcca tatttcaccc agccagccac tgccttcact tccgtccgag 26040
gcctaatctg agcccatggg aaacctaaga accccctacca caactgcctc aactcttggg 26100
aatcagggtg tatgggggtg acaggaagtg agcatacatt ctccaacttg atatgtcagc 26160
ccccacgtct gtatgaatgt ttgctcacac tgtgactgcc ggccttgctc ctcaggctgc 26220
atcctaccag ggagtaagac ccaagtcctt cctgctttca gacaacacca agcctcatga 26280
gtccccactc agaggaagga ccagagacaa actctaatgt tccactaata cttcccttct 26340
tattactttc cttgaaaatc ccttctccct ctttcttttt atacttcgct aatgaaaggt 26400
aatgaaaggg tctggcactt ggaatttaga attgatacat ggtttttaac ccgcggacgt 26460
attccacaat aaccccttgca tcttctacta agatgtgggc taggaaggga ccagccagtt 26520
cccagggtca cagtgcctca gctgatgttt catattttca gcaactttat gttagagatg 26580
tccatcaatc agaacaatat ggttagagaa taaactaata aaagtcattt ttgaggacat 26640
gttggaagtc tatcaaaagc attgaaatta tgcatgctct gaccagtcgc atgtctaaga 26700
atttaaatat gatcataagt ttaaatatga agatgtttat cacagaattg attataaaac 26760
aaaattgaaa aaaatagtgc tagaagtttg atcataggga cctcattaaa tgcattatgg 26820
ttgatccatg cagtggtttg ctgaacagcc attaaaatgt tgtagaataa ttattaatgg 26880
tgtggaagga tgctattgtt gcagtatgtg aaaagaacaa attacaaagc agtttgtgca 26940
gcataaatatt tttatttttt aaaaacctgt atgtggctta tgtacatata aagacgtgga 27000
ataaatgcac aaggtactca gtttttctca gtgaagccca ttttgcattt tgggctgggt 27060
aattcttcgc tgtggagaac tctcattcat tgtaggatgt ttacaagccc tgggccttac 27120
ctctttaacg ccagtaggca cccccagcat ggcaacaagc acaaaatggt ctctctcata 27180
ttgcccttga ggaaattttg caactaagta actattactg ggtcctagat tacagtctgg 27240
attattgcgt tcctttctta tttttatttt ctccaattcc ctttaataag catgtactgg 27300
attcataaaa aaacaacata aatggtaatt acaatattcc gcactggtta aaacttatgt 27360
aaataagcat tctgctgctt tagccacaat tgcaatttat gctccttctc tttcttaagt 27420
tcccagttcc cacgtacatt cattcgactg attcaaaagt cattttagct tgatagactc 27480
ttaaaagtta gagttatcat ttctgctatt tattctttca attatccatt tgtccaccca 27540
tccatctgat ccattttgtt gatgcatgct gtgtataaaa tactacacca gcctggtgcg 27600
gtggctcacg cctgtaattc caggactttg ggaggccaag gcgggtggat cacctgaagt 27660
caggtgtttg agaccagcct ggccaacgtg gaaaaaccct gtctctacta aaaatacaaa 27720
aattagccag gcatggtggc agacgactct aatcccagct acttaggagg ctgaaccagg 27780
agaatcgctc gaacccagga gatggagttt gcagtgagct gagatcatgc caatacactc 27840
cagcctgggt gacagagcaa gactccgtct caaaaacaaa caaaaaaaat acaatgccaa 27900
gcatcataaa aaatatagtg atatataaga cctatttgtt gtgctctagg cattgacatc 27960
tagctgtcaa ccattaatat gtgtaggagt ctatctatca atattatgga ctgtgcttga 28020
agacttcttc cccaatcttt ttctcttccc attaagtttg aagtgaggtt ttctgagtga 28080
agtatcatag tacatacagt ctcattattt ttcaaaaatc tctggttata gtacatttct 28140
ttcctttatc ccctttgttc ccaactatca aaccattttg gatatccagt attggtatcc 28200
agtattatta aaaagcaaaa cagagaacta ttaacaaaaa aatttgtagg agtaattggt 28260
tgtatggtat ccagtactat tagatagtaa atcagaaaat tattaacaaa aattttagac 28320
gaataatgga ttgtcttgcc caagtgaatt gagtgattta gttgttcttt catttttagc 28380
aagtacagct gatcatttga ggccttactc attgtttgat tttgcaaatt cttactatta 28440
taaatgtttt gggctctgag aaagctgttg tcttaatctg tttgtgctgt tataacaaaa 28500
tacatgagac tgggtaattt acaaacaaca gaaatttatt tctcatagct ctggaggctg 28560
ggaactccaa gatcaaggca tttgtcttca ggttcagtat ctggcgaggg ccggttctct 28620
actcccaaga tggtgtcttg tcactgtatc ctccagaggg ccaaatgctg tgttctcaca 28680
tggtagagag atagaaaggg ccaactcact ccctcaaggc ctttcataat gttaccaatt 28740
ccacttgtca gggctctgcc cccgtgactt tattacctct gcaaggcccc accacttaat 28800
actatcacgt tggttattac gatttatcac atgaatttcg accatactag ttgccatcct 28860
ttcattttca tatatcctta aaactttgcc tttctcattt taatgtactt tatccacagt 28920
atgccaactt ttcgatactt ttgttaacct gtctgacgat atataggaaa ctgtaaaagt 28980
gcagtttttg atacactctt tagctgcccg tttacttcta ctgtcgttag agaaccccat 29040
ccatagtgca tgtgtttatt ttgtgtatga acaaagactt tatatatagt ttgggtcatt 29100
tttattcatt agtgcttccc ttataatctc tgaataccat tttattagta catactgcta 29160
ttcttaatag taactagcat gcctgatcat cccaaatgtc taggttcaca ttttaaaata 29220
agttatatct ttgggcttaa cagtttattg aaaggtaaca aggattgagt catagttgta 29280
tgtttttgga agtagaattc aactgtaaat agaaattggt tgtttagatc tcactatata 29340
tgaaaaaatg aaggctttag gagaaaatct ccccaaagta cccatttttc atgtgataaa 29400

-continued

```
tatcatgaaa tgatttgaga aaaaaatgta tatttgttac agctaacaaa tatttgtgtt  29460
ttttattctt catggagaga atgaaatttc ttctcttctt tacacatttc tttttcttat  29520
tagaaactaa ttggtgcctt tataaaaatt aactgcagag cactaacgtg tatatataag  29580
tattatgtag ggtgtagggt atgttcaggg tatggtgtgt gtgtgtgtgt gtgtgtgtgt  29640
gtgtgtgtgt agctgtgtgt gtatataatg aaatatatgg tagtgttgtt tcagaaatct  29700
gcttggtctt cccagagttc attcatctta taaattcatc tacattgatc tctatttttg  29760
gaatccatga aatgtttttt ggcagtactt cctttaatat agtgtgctgg aaatctggaa  29820
atttctagcc agattagtta caaaaaatta gccagtggtt ttgcactctc tatagaatca  29880
aggcccaagg cctactcttg ttactcaggg ccttgtttta tctggcctct ttcttttcag  29940
ccatatagct ctcaaatact caacaaaatt cttcattcta ggtagacaag tatcttcaaa  30000
atacttccca attatctaat aactgtctta ccactaagaa ggcttttatg tctcctgtct  30060
gaattttatc catgcaaaaa agtccagccc aagcctccag aactccaaaa agttatccct  30120
aactgctgaa acacagtaat ttcactatgt gaaatttcac tttggtctcc tagcatttgc  30180
agatatacca tacatatcct tgatcctttt cctttcatac cttttatatc taacccttaa  30240
gctaataatt ttacctacac tgtaattcaa aatgtatccc cagtcttacc atgtctccct  30300
tctctactgt taccacccta ggctaggcct tcatcatttc tcacctggac tccttcccta  30360
acctctgaac tgatctgcct gcttccactt agacacccaa cctagtccat tcttgagcag  30420
tcggaataat tcttttaaga aagaaaccag atcacatccc cctctgctcc caaccatcca  30480
gtgacctctt atcatacata gaatgaaatg caaatcttta ctgtgtttta aaggccctac  30540
attatctgga cctcagtaac ttcttacttc ctatcccttt tctccttgta tgccaccctc  30600
caactacact ctaactacac tgtctttttc cctgttcttc agacctgcca accatatttt  30660
cactgctcaa ttaatatgta gaaaatgaat tgtttgttaa atgtagactg tttccttctt  30720
aaagcaaaga taaatgacat tgtcttcaaa aacaactaac tgcccagaat tcctgatttt  30780
aattttaaaa agacaaactg caagaatgtg ttaaacagta aggaaacaat tcactacttc  30840
agaattctat atgatttcac tgcacgttag taattttgta tattatagaa tatgagggta  30900
ttctaataaa cttaactcta tgctgtatac ttatcatgat agctcatttt cttatatgtt  30960
tataacagca ctacttattg tacatggata cgtgggaaat aaattaattt tctccttaag  31020
aacaaagcaa ccatttcact catgagataa atcttgaaga tttaaaaact acttataatt  31080
aattatacat tattcatata atgttaagta ttttcttagt aaaccacata atttagaatg  31140
gcaattggac agatgggcag aaccacatgc atccactatt aggcagttgg tgagcataag  31200
atgccagaaa gaagattagg aatatcaagg cagggagctt ccgatcgctc ttgaaaacat  31260
tgacccttca ctcctcactc tccacgatgc atttcctttg aaaagtaatg ccttccaaaa  31320
caaagttctc tgttttatat ctaaacttac tcaatagttt ctcatggtta ttgatatata  31380
aaaaataaag taaaatgttt aggcagacca aaagaagaat ttccccctcc ctctgccttt  31440
tatgccaagg tgacagctat gaaatgtaca gtacgtttcc tctgcaagga atgtagcagt  31500
gttccattgc aagaagatga gagggagaga aaggttgcac gctgaggaat atagtgtcat  31560
ttgtcactgc ctagactcat cagctgtgtg gaactctgag aggcaccagg cttctttatt  31620
tatttcttca gaaacttcag caaaaaagat ttcattagga gcagagaaaa atgtgaaaaa  31680
cgaattagct tttgtgatgg ggagtagtca tctctgaata ttgatcaaga ttaagagggt  31740
tgtcttcgta acttctttta tccatagtct atactgattt aactagaaaa ctaatttcag  31800
```

gtggtatttc gggtgtggca gatctttata gtaaatgaag aatctagtca aatctactga 31860
aaaactctgc ttactttaat gtttgatctg gttgaaacca ttttagctta acaatccttc 31920
ctctgaaaca gggaatcaat tgatatccta cagcaaaatt atgtggaagg gccattagct 31980
tcacatccaa tgcaaatttt gcctgtgttt actcttcccc aatccaaaat atatcagatc 32040
ctagatgcca gtgaaatcgt ttgagctaga tggcttgagg gtcatagctt ttttcatttc 32100
ctgttctcag acctcttata attgatagaa taaaatcaga agagccctag agctgtccca 32160
cctattctgc ctcacaaaag tagaagtaat ggcaaccact atcataggga tcatgctcac 32220
ctttttctta ccagacaaat ttggatatta gcttgaaatt aataccttcc ttaaaatgtt 32280
ggaatttggt tatatgcgaa attttgctct atttattcat tatattttgt atggaattat 32340
ttttgcccta tattttcact taagtgttct ctacccaaga ttttaattga acccaaatca 32400
gccagacaca cagacatgga ttttgctgcc accaaggtta attcttcttt taaagttaac 32460
ttttaaaatt tggtaaaata tagctttgaa aatttgcatt cgtctagtgt ttgttatgta 32520
tttcccccctt ttgtttgatt atatgtctat atttttcttg tagaaattga tttttaacct 32580
gctttttatg ttagctttta tgagcttctg tctgaattct gaatatgtct ttcttaatgt 32640
cttctaaatg tttctttctg gattattaaa agatttatta ggcttttaat aattatattt 32700
gttaccttag ggaatgtgtt tgaaaatatt ttaaatggaa ttgccagtta acacagcatt 32760
gaactttttc ttgttagaga tacattgttt tctaggcatt ttattgggag agaagttagt 32820
atgatataat gtctttggct gatattaact cttctaagat gcattgtttc tgagaacacc 32880
attgtctgat ttcattcagg gaaatttcac acaagccagt agagtcaata ctttttttcaa 32940
gacctgttaa ttgatatata taaaaacttg ccattgttta catgcccatt tcagatcctt 33000
tatgtgacct aagctagaaa tgcattttaa cagcatttgt ttttccaaaa atatttattt 33060
atttatttat tatagagata gcgtctctct atgttgccca ggctggcctc gaactcctgg 33120
gctcaagcaa ttctcctgcc tcggcctccc aacagtgctg ggatacaggt gtgagccatt 33180
gtgccaggcc cttgttttta ttttttttga acattgtatt ttgaaagggg tttgaaggtg 33240
atccctagat agcaaccagt aatgattcga gcagcaaaac aatctaaaaa gtaattttat 33300
aagaaaatgc agaacataaa tgagcccata aaaaattata ttaggttcta tttacattac 33360
taccttcttt cacatgtaat atttcactaa catttaatga atttctgtgc agtgccatat 33420
accattatga attctaggat agaagaatga gtgagaaatg ttcttaggcc ttaggaagaa 33480
ggaacaagca tctctgtgta atagttattt caactcttct tttacacctc attcccatat 33540
taaatctcag aaaagctaaa gtaatagcta tcccagatct attttagact ccagacactt 33600
acttcaatgt cttgttctcc ttatcagact ggaatcattc caaacctctt aacttctggg 33660
caaccatgat aatgcgacag aaaggacact aaatctgtcg caaatttatc ttgatattct 33720
atccagtctt acttggtact gaaggtcaca agtaaaataa ggtggttgtt ttttgtttgt 33780
ttttttttt ttgacagaag agaaaagaac actgtgagca cagagtgaat gtctaacatt 33840
gattcttgag tagcaggaat tctctatgcg agaggatctc tatgcaaaaa gatctcatat 33900
tctagcacaa tttaaggatc tctatgcaaa gatatcccat attttagcat tatcaataag 33960
ctatggggta atatattgta tgtggtgtgg cttgaattct agaaatttga tttctagaaa 34020
tggtccctgt agttaaggat atataatgtg gccgtctcca gttttctatg aggaatagga 34080
aaatactatc attattagct gtgtgaccat ggacaacttg cttcgttctt cagttgcatc 34140

-continued atctgtataa aataagaata agaaaattta catctgcaag gtgtgatgga gatcacatgg 34200
gataattgtg gtcccagagc ctggcacaaa agggcttaat atttataatc ctccccattt 34260
ctccgtatac tctaaaggaa gtttattgct tatcaaattg tgccgtggtt agttgtacag 34320
cttccctgcc aaattgtaaa ctccaacact aatgtgacgt tacattttat atagtgctat 34380
gattttcaaa ttgtttgcat aatttcaaat acacagtaaa ttgcttttta ttagtataat 34440
tattgctatt gtcaatatta ttattacaac agcttcacag taagatgggc agaaaaaaat 34500
ttaatttcca ttttacaaat gcacttttga ggctcacaga agtcaaatag accaaagtca 34560
cagggctagt gagggaccca gaagaaacaa attgtaattc actgattcca agttcagtgg 34620
ttgccttact gcatcataaa ggctattaca caatccaggt gtatcatatg attcttgtct 34680
atatattcat acatatcaga aaaagtgttc tactcaaaat tgctagcaat caacagatac 34740
tgatagtcat tagtacttaa atctttatca aatgaaatat taatacccat gaaagagagg 34800
acaatgaaag gtttgtatca tttgtatgtc acaagtcaac ttttttcaat cactcattat 34860
tagtttaact gtaaaaaatt atttacattt agcgtgaaac tttcctgtat tctcaacata 34920
tttccttcgg tagaaaagca aacctccagt tctctgttct ttgcttggat acttgccagt 34980
ttgtaactca gctatcaaac agtaaagctc acaaaacact tattaaaatg actaaaatcc 35040
aaaacaccaa gagcacagca tgctggtgag atgtggagca acaagaactt tcattcattc 35100
actaatgctg gcaatacaaa atggtacagt aactttggaa gataggttga caatttctta 35160
cgaagctaaa ctatacttaa catatatatt tgtccatttt cacagtgcta aaaagaagtt 35220
cccgagactg ggaaatttat aaaggaaaga ggtttattta attgactcac agctcagcat 35280
ggctgaggag gcctcagaaa gcttataatc atggtggaag gagaagggga agcaaggcac 35340
ctacttcaca aggtgacagg aaggagaatg aatgcaggag gaactaccaa acacataaaa 35400
ccattagctc tcgtgagaac tcactcgcta tcatgagaac agcatggggg aaacagctct 35460
catgatctag ttacctccac ctggtctctc ccttgacatg tggggattat ggggattata 35520
attcaagatg agatttgggt ggggacacaa agcctaacca tatcaccata tgatccaaaa 35580
tcatgctaca tgatattcac ccaaaggaaa tgtaaactgt gtccacacca aaacctgcac 35640
atgcacgttt atagcagctt tattcataat tgccaaaact tggaagcaac caagatgttc 35700
ctcaataggt gaatgaacaa aaagactggc acatgtactc aatggaatat tattcagtga 35760
taaaaagaaa tgagctatca agccacaaaa acacatggag aaaacttagg tacgtaagcc 35820
agtttgaaag gttgcattct atatgattcc aatatatgac attctgaaag agacaaaatt 35880
ctggagacag taaaaagatc agtgattgcc tggggctctg agaaagtgca gagggatgaa 35940
tgggtgaagc acatggcatg tttaggacag tgaaactatt ctctatgata ctgtcatggt 36000
ggatacatga ccttatacct ttgttaaaac tcagaatttt acaatacaga gtgaattcta 36060
atataaacta tggactttag ttgtaataag gtatcaatgt tatttcataa gttttaataa 36120
tgtaccacac taatgcaaaa ttataataat aggggaattg ggggaagggt aatggagtat 36180
atgggaatgc actgtaatct cagtacaatt attccacaaa cctaaaactt ctttcaaaaa 36240
tacaagctat tggtcaggtg tgatggctta taccagtaat ctcagcactt tgggaagtca 36300
agaccctcag atcacttgag gccaggagtt cgagaccagc ctggccaaca tggtgaaatc 36360
ctgtctctac taaaaataca aaaaaaaaaa aagaaagaaa gaaaagaaag aaagaacaga 36420
agaaataaaa gaaagaaagg aaagaaagaa agaagaaaag aaagaaagag aaagagagaa 36480
agaaagaagg aaagaaagaa acagaaagag agaaagaaag aaagaaaaag aaagaaagaa 36540
agaaagaaag aaaagaaaga cagatgcggt tgctcatgct tgtaatcaca actactcggg 36600
agactgaggc atgagaatcg cctgaactca gaaggtggag gttgcagtag ggtgagatta 36660
cgccactgca ctccagcctg ggtgacagag caaggctctg tctcaaaaaa aaaaaaaaaa 36720
agctattaaa aatatgtaaa gctcagtcta gatacagtac cagaatagta ggaactttat 36780
ttcacctgtc ctacaaatta tggttgtgtg ccacttgggt aaaactcaga atccaaatat 36840
gtgaatgtaa gatttatggg gaaattattt gtatttcaaa ataatcctta atgaatgcac 36900
tccttctaaa gtagccatta ataaagcagt taatgtttca tttaattata gattaatgta 36960
cataagatat gccaggaatg caattaggaa ctgggaaggg ggtgttattc taataacttc 37020
cacatagcat tgtgagacat tttctgcttt cttcaaattt catttaatta cattttaaac 37080
aaatattttt gtgagcctat tatatagtcc ttcgctagca ctgaggagac atgctttgtg 37140
accttggtga tttcacattc aaatttccct ttcacctaca ctcttccttg tttttttcatg 37200 cctgtgtaga ttgtaaattc ttcctcagat taagacattt tattcacctt tgtaacatcc 37260
acagtatcta gcacaatcag tgccttcaaa aacaattggc ctcaagaatt gattgactca 37320
atgagtgact gaaagactaa attaataagt acacatctat ttgtacttcc ctgcttactt 37380
ataaggtatg acaatgaaat actgagacag ttatacatta cttacggact caatctcatt 37440
tctttacaat ctctattctt cttttttgag tataatgtta ttttacaatt ccactaactt 37500
gtcactcttt attataaatt catatctcca tttcacctga gaataataaa ggcaaggaag 37560
tattttaaat gatcttgttt tttataacta gcattcattg agcaaatcaa agtatgaaaa 37620
taatataggt gtcagtgatt attataaagt tgtatgcaca aaacattcca atgattgggg 37680
ccaatacaga gaaaacatct caatatttgg aattttgctt ttctgtaaat actttgatat 37740
gtacttacat catatcaatt ataactcctg ctgaaaacaa acagtgcaca caaatttggt 37800
agttggagga gactttataa agggactaat tacgaaggtt tagaccgggt taggaaaaac 37860
acacggaata gtgcaatact ttaggatggc aacagcgagc accgttataa ccactaggcc 37920
aaaatgaact aaatgaacag ggagattacc atttatcaga aaaagaggga gaaaggaagg 37980
agagatgacc aagcaagtcc tatgtgaaga cggctgcctg acttgagctg tgtgatcttt 38040
ggactgatac cacctgcctg cactggccta gcagggcgag aatagtcaat atctggaaaa 38100
tggatcacct gaccttactt tcctccctcc ctgtttcctc tttgtggtgt ttccactggc 38160
caaactcaca gcgtagacaa aaggagtgca ttgatgtagc agtggttcta atccagggcc 38220
aattgtgctc ccagggaaca ttagtggtta tcacagctca ggggaggaag ggagaggagt 38280
ggagtgctac tatgattcac tgagggattt ttttaaacat ctacaatgca caggacatcc 38340
ttccacaaca aagtatccag ttaaaaaatg tcattactgc caaggttgaa aaaccgtggt 38400
gtagtcagta caattcatct tctccaggca cagtgcagga gtggggtgga gtgtctgaag 38460
gggaagaagg aagaaaccag cacaccccac aaaagtaacc aatgcaaata ccaaatagga 38520
aaagacagca cttaaaatac aaaagtctca ggaatatatc tgatagtgtt ttatggaatt 38580
tattaaaatt tagcctggag tgagtaatat ttagcaagcc aggtttgtct ttagagaaat 38640
ccttgtgggg tttatacaag gatttattaa caaagggcac acacaatact catattacag 38700
tcagtctggt tatgtaaaac atgggcaaga atgtaatagg acaatgtgat gtattcacaa 38760
aggattttag gactacacag ataatcctct aatgctttca cttacgtact atgaaaggct 38820
atagtttgca tagtgatata gccacgtaag atagtaaact tgacattcat gcagctatac 38880
atgtttgcac acaccaggat gcatgccctt tctacctggt tgattttttta ttcttttatt 38940
aatctctaat ttattcccca gaacactctc cataaaaact ttctcacaac ttaaatcttt 39000
aatctattgt gtggatttct gactcattct ccaagctttt cctcttccct ccgcaatgcc 39060
ttatagtctt atgactattt atccctttgc ctacatttct agccagatct cttgcctgat 39120
acacactctc atatttctct ttgcacgcta cacattttta tttagatatc acactactac 39180
tttgatttca acaggtctca gtttaactta atttttcctt caagcaagga gtcccttcat 39240
atcagttatc accattggca ccagaatttt tcttatgact tcccatgacc tacaatataa 39300
accatataaa tcactgatgc ctccatagtt ccctccctct caaatttagc cataagatga 39360
ttttaggatc cttgtttttt ccaatctctc tttcattctc tcccccatct cttccattat 39420
gaaggtttgg ataggacaca actcatgcct agattagtgc aatagatgct gagcctgtgc 39480
agcggtagtt tagctttctc tcctggttaa ctttaactgc cacatatatc acttcacacg 39540
tcatttttca ttcaaacgta tttaactggc tcttcattca taagaagctg gaatttgtcg 39600
tttgactgat attttaaaga ttttatattt tttctccatc ctcgttctaa tgttgtatct 39660
tgtgtcattt gttcattcat aaacttaaga cttagctaac cactgagcat ccaggaaatt 39720
cagtatctat catgtgaatt ctctaatact ggttgatcca ttgtcaccag agcatagcag 39780
gcttctcctg cctttatgta tgtttgtcat atagttcatg cctaaaattc tttcttaaat 39840
cttaaattcc taagatacac acttttgccc aagatcacag taatctctgc cataatctct 39900
gctggaatct gttcactgtg ttgctcctgc taaacttctt acagatgact ttttttcttt 39960
ttggtttccc tggtatctag tataatttct tatataggta ctcaataaat gtttcctgtt 40020
gatctctaca cctactctgt acaataccat agtgactaga cacatgttgc tatcaagcat 40080
ttcaaaagta gctagcctga gttgagatat aggggtaaaa tacacaacag atttcaagac 40140
atattatgaa aaaaacccat aaaatttctc agtaattttt ttatagatta catgtagaaa 40200
ctataacatt ttgaataagt tgtatcaaat aaaatataaa attcacccgg ttctttttaa 40260
tttgttaaat gtggtggcta gaaaatttaa aattacataa ttggctcaca gaataattat 40320
aatggatggt attgctttag atcaagtttg tctaacccgt ggcccatggg ccacaagcgg 40380
cccaggatgg ttttgaatga gatccaacac aaatgtgtga acttccttaa aacattatga 40440
attttttgtt tgttttgttt ttgttttttt ctcatcagct atcatgagtg ttagtgtatt 40500
ttatgcatgg ctcaagacaa ttaattcttc ttcaaatatg gcccagggaa gccaaaagac 40560
tggacaaccc tgctttagat agtaaagcat atgagtagtt aatgtgtact ataagcagtg 40620
tgatctgata gactatttaa tgttgtttga tggtacatta ttcaagtcga ttattatgtc 40680
tacctatgca gtttaacgac ggtaatgaga gagggcagct tgattacagg tcttatcttt 40740
tgactaactt gctaggccac ctgagaagga cccaaattat ctgaatgctt aactcaacta 40800
atttgtattc acttgaagaa tttcaaggat gtttatatgc catcaacttg ctttaaattt 40860
tttctctcag tgaaaatttt tcttaaaatg agtatgtggt attcaaattt atccttgttt 40920
tctatgatta tcttttcata gcactgtggt ttccaggaac cttttttttt ttgagatgca 40980
ttctacatgt aactattgca cagtttgcat gtagtaaggt tcattattct tctacttttc 41040
caaacacctg gcatgtttac ttgaggttgg tacaccttgt atcccagatt ttgctgtttt 41100
taacttaaat attgaatatt ttgattaaac attatggaaa gtttaaatgg gtcaagaaaa 41160
atagcttttc ttcccatgaa gaacaatacg gcataggagt taagagcata gatttaaagt 41220
cagaaaacct gtgctgccta cttgtgcaaa gtcacttaca tgctgtactt ctgtttcttc 41280
atctgtaagt tctaccccta ggtatttact taagattaat ggaagcatat gttcatacaa 41340
tgacttgtac agaattattc acgatagcat tactcttaat agctctaact ggtaacaaca 41400
caataatcaa tcaacaattg tgctgtattc atacagcaga atactactta gcaacaaaaa 41460
tggaatggac tactgataac ctcaacaaca tggatgaatc tcaaaactat catgctgtgt 41520
gatgccaggc acaaatcagt acatactata attccagaaa agacaaatgt catccatggt 41580
aacaacaaga tccatgcttg ctggaggtag aggcatcagt tcagtcattc aggaagctga 41640
ttccaagatg gtgttagaat tacaaccatc cacaagagat ttattgcagg caatagctat 41700
gaaaggtaga aagagaacag gagaaaaacc aggcaaggaa aaaccacaat gtagttgtga 41760
tatcacttca aagggaggca gaaggaagga gaattgggta ggaatagcca cagattacag 41820
tgcagttaca agaaagtctt ggcttccaac aaaggttact tgttgaggag tcatgcatta 41880
ggcagacatg tctgggctgt agtttccttg ctgctcccag tcattggctg gaggccagtc 41940
tgggttcctg tgctgtggtg gatcccattg ctgctgcagc aggaggccaa tagcactcct 42000
ggcagctaat tggagagaaa agatccaaga ggtgtacctt catggctacc cccatggggc 42060
tggggtggag gtggaggaga aggagaagga attaactaga aaaaggcaca aaggaaaatt 42120
ggggaaaata atgaagatat atgatttctc aattgtggtg gtcgttacat gggtttatta 42180
atgcatcaaa actcaagaaa tgtacattta aaatgagtgc atatgattgt aagtgaatta 42240
tacctcaata tagttaattt tttaaaaatc atagatttct ttatatttaa tgcatgaaca 42300
taaacctaag acactcctcc actccaaaac ttaattacct tgtgatcagc agagcagaag 42360
gtactttgtg atatataggt agagaagatg aagtcttgtg acatttaaca agggacagga 42420
aaatggacct tgtcctaagt taccaaactg caaaaatatc acctacaaag gctattcata 42480
acatacattt tcaagggggt tacaatattt gcctactata aaattttgga tctgtaaagg 42540
ggttaaatta tttgtgcagg ggaataaaca tcaaagaaac attaagaggt ccagagaagt 42600
aaaataggaa gggtcttttg gctagaggag atatttaact ttcagaacat gtggaattaa 42660
gttgtattga ttatgatctg atcttcttcc ccctaaattt gatcctcttc ctgtaatcta 42720
ttgtttccat catcttcaac tcttcccttt ccctctccct tgtccctcag ttctagtcaa 42780
tcacaaagtc ctacagtttc actttctgta taccttattt ctggaattca tctctagact 42840
tcaaaatata tatatatata ttttttttt tgagatggag tctcgctctg ttgcccaggc 42900
tggagtgccg tggtgcaatc tcagctcaca gcagcctctg ccacccaggt tcaagcgatt 42960
ctcctagttc agcctcctga gtagctggga ttacaggcat ctgccaccac gcctggttaa 43020
tttttgtatt ttcagtagag atggggtttc gccatgttgg ccaggctgat ctcgaactcc 43080
tgacctcagg tgatccaccc gcgtcagcct cccaaagtgc tggaattaca ggtgtgagcc 43140
actgcttcca gcccaaaata tcttaagtag ataattgcac gactaatctc tgcttttctc 43200
tcccagcagc cttccaaatt catgtctcac agctgacaga gttgttcctg ccttcagatt 43260
catgacctgg ctctgtgttc tagctcaggc tttctctctc atatcacctc ttgcctctct 43320
gttgccccca tattttcccc tctggttggt tggtgctcct ttggaaccct ctgcatatct 43380
tttcaagaat attatgactt attatgccta taaactttgt ttaattattt atttctaaaa 43440
tttgacaggg aactttccga aggcaggtat tgtgtctttc tcatttaaaa gcaaattctc 43500
gcctggcatg gtggctcatg cctgtaatcc cacactttgg gaggctaagg tggacagatc 43560
acttgagcct aggagttcat gaccagcctg ggcaacacag ttagaccaaa aaaaaaatat 43620
atacgaaaat tagcctggca tggtggcaca cccccgtagt ctcagctagt ctggtagctg 43680
aggtgagagg atcacttgag cctggatggt tgaggttgca gtgagctgtg attgtatcac 43740
tgcactccag cctgggcaaa aaagtaagat cctgtctcaa aaaaaaaaaa aaaaaaaatt 43800
agtgaatcct cagtgtttaa aaagtccata aacatactaa acatagaaga cctccaaatg 43860
aaattaatca attattattt agtgggttgc ttctcttttg ttttaatata gttttaacaa 43920
agagtaaaag ttatgatctt tttatatgta aaataaataa tgccgggttt gacataaatt 43980
ttaggaaaac tagagacgct acttcctaaa aattttcttt ctataatctt cctaaatatt 44040
tttccataaa gtacaaaata atagaaaaaa attaagagat tgagtatcct ttcaggaagt 44100
gatatgacaa atagggttcg agaactattt gaattctcac cacttttcat aagggcagat 44160
ctcaagttaa atttttctat tcgaatttaa atgactttca ctggaatacc attacagaaa 44220
agcttctgtg tttagatggc aatatggagt ttcttttctt ggaatattaa ttgaaggaga 44280
agtcttaatt ttttaagtct atatctccgt atatatttga acctatttta tatgttagtc 44340
cttctcttta gtaaccttca tccacagtga acaagattta cccttacctt taagcagtag 44400
cggctacttt atgtgaagtg aacagctgct ttttttatct gcatctagac atcaagtagt 44460
ccagagtcct ttctaacacc ctagcaatag aagtaagaat attttgacca ttccatgact 44520
tgatgatact tctagtaata atactgtatt attaaaaaca aacaaacctt tgtgcagtgg 44580
taattgaagc agttccttgg gaacatgtat taagtacttt ttagcagtta agtccactct 44640
ctgtaggtta aggaatattt aaataaaata atgtggcaaa tgagttcaag atgataaatg 44700
cgatgagaac taaaacagct ttaattttat gtgggaaata aatagaggaa aagtacatta 44760
cagggctcct ggacttattt ctttcttcaa agtgtttctc ctagcgaata ttattactat 44820
tttttctctt aagtaaaaaa tacacaaagt atgaatctac acaggataat aatattgaag 44880
ttaaggatga tgtctcctcc ttcactctcc aaaatactat ttacttggct tcatggaaat 44940
ctctctcact ccaattccac cgtgtcaact gaggtcttct gttctttctc tccctatagc 45000
atattcctgt tacataaatc ctaaactgtg tcgtgttagt cacacactgt aacctctaga 45060
taagcgcctg tccagaggtt ctcaatcaga gccttgcaaa tatgtattaa atcaatgggt 45120
catcttcagt gtctcagtgg gcccttggat atgttttgca gactgctgtg agtatgtagg 45180
gatgtccagt atcgagggaa gtgtggatgg ctttcattgg ttcttatagg gctgaagaac 45240
acatagagca gtaagcactt ctactgtagg gagagatcga gcttctccca tccccactgc 45300
tggcaccacc accaccctac accccatttt gagttctgaa agtgaatcct tgagaaagaa 45360
cacacaaaac aaccatcata atagtgggca cagctgtggg tggtagaata acattcccaa 45420
gcttcttttc ctacacatga ttaatattaa ttcagcaaac atttattcag ctcctacttt 45480
taaacaggca ctattctagg tactaaagac atagaggcaa agcatacaag actctgcctt 45540
tgtgaaacaa ttaagaaata agtaaaaaga aaagaaacag aaaaggcaat ttggatagtg 45600
tcaggtgcta taaagaaaac aaaatgccat tttaataaat aataataata caatgttttc 45660
atactatgtg ctagacacta tgctagtagg tatttataga cataacctca attaatcctc 45720
aaaatggcat gttgatatca ataccccaag tttacatatg agacttaaga tgtctgagta 45780
tattccccca ggtaacaatt aatatgcaca ataaaacttt ttgctcattc atttattaac 45840
ctatgttgat tgagtaccta ttttgtgtca ggcatcattt taaggcacct ggatatagtt 45900
atgaacaaac aaataaaaat ctctgccctc aaataattaa tatctcacag aggttaggca 45960
aaatataatc agaaaataag tataacgtat aggatgccag atcatgaaag aagctatgaa 46020

```
tggcatcaag aagctggaaa aggcaaggag acagattttc tcctagagtc tccaaaacag  46080
aacacagtcc tgccgacacc ttaactttag gctagtgaga cccctattgg acttcagact  46140
tacaatccca caatgtaata aatttgtggt aattcagtag gggaacaata gaaaactaat  46200
acgatatcaa aacaaattat atcatagaac aagaaaatgt aattgtgaca aataatacct  46260
acaaaaatgt tgtaaatgct aggcaaataa tgtgtttaaa gcacttaggc caatgttcaa  46320
cgtaaagtaa ttcatgctat aatatcatca tcatcattac caatatttag gggctctaac  46380
aaatgatgta cgtgtaagca gatgtaagaa aatttccttg ctgaagagga ggtattaata  46440
gagtatataa caatagataa caaattccaa ataaaggcaa actaaatgtt ttattggatt  46500
aaatttaatt ttaaaaacta caagaggccg ggcgcggtgg ctcacgccta taatcccagc  46560
actttggaag gctgaggtgg gtggatcacg aggtcaggag atcgagacca tcctggccaa  46620
catggtgaaa cgctgtctct actaaaaata caaaaattag ctgggcctgg tggcgcgtgc  46680
ctgtaatctc agctatttgg gaggctgagg caagagaatc acttgaacaa ccaaggagtc  46740
ggaggttgca gtgagccaag attgtgccac tgcactccag cctggcaaca gagtgagatc  46800
ccgtctcaac aacaacaaca acaacaacaa caacaacaac aacaacaaca acaaaactgt  46860
gagatccatg gtgggctttt aagaggaaaa tgcaagctaa ggtttgttta gactctgagt  46920
actgcatgtg taaaaataaa ggcatgatga aaagatcaag agattagagt gatacttttt  46980
atctactagt gtcagagtca tgaccagggg attggctatg agaatacata agctgtgcca  47040
ggagtaatcc aaggagattg tttcaatttg gaagagtgtc cacagaatga ttctcatact  47100
agacgttggg ctattgtaaa gaaagttggt aggtactcca tcgctaggat catatcaggg  47160
agaaattgaa caggatggcc ctaatgaccc tgttgtaccc ctagcttatg gattaggcaa  47220
gtcacttcta ctcgtatacc ctgtttcccc atttgtaaat aagaggatgt gttactctaa  47280
ggatctctaa gattctttgc agttgttaaa ttgcatagct ctccactgat tccatggtgg  47340
aaatttgcta ttctattaca aatattctaa atgtatgaga tatcagacat actcatttaa  47400
aaaacaaaat acaaaaaata agtattctac aaataaacac agataatgtt taaattctat  47460
atgtctttgt ttctcttcag aagcatccaa aatacaaacc atctaagagg caagaaaatg  47520
tcgtgatgtt cctagtgcaa gttaaaaaga tttgctttcc tcaagtcgga aagcccttct  47580
catttttgag gttttttttct tcttttttttt ttcaagtgaa agcattttgg aggagtcaat  47640
atccatcttt aaaggtagcc aggtcacatg tatacatatg taactaacct gcacaatgtg  47700
cacatgtacc ctaaaactta aagtataatt taaaaaaaaa gaatttaaat aaaaaaagaa  47760
aatcagagag aaaaaaaaaa agatgcatgt gcaccctgat actaccatcc atagtgatac  47820
ggtttggctt tgtgtcccca cccaaatctc atcttgaatt gtaacccccca tgtgttgagg  47880
gagggacctt atgggaggtg attggatcat gggggtagtt tctccatgct gttctcatga  47940
tagtgaatga gttctcataa gatctaatgg tttaaaatca tggcacttcc ttttgctctc  48000
tctttctcct gccatgtgag gtgtgccttg cttccccttc cccttctgct atgattgtaa  48060
gtttcctgag gcctcctcag ctatgcagaa cggtgagtca attaaacttc tttctttata  48120
aaaaaaaaaa aaaaaaaaaa ggtagccagg taaaaattac ttgtttccag gacattttca  48180
cctgaaagaa gcattgtcat ataacataga agcaagaaat ccagtagtgg gggttattta  48240
aaaatagctg gaaaatttca atcagcatga gtttgaagca acaatttatc atcacctttt  48300
atggtgggtg gggttaagaa catttcagcg ggcaaagtgg tggtgatggg gaagagacac  48360
```

caggggaggt gattcccatt gcattgcttt gtaaacagag gcacaggttc ttcatttttg 48420
tcacacaaaa tcacagctat gcagaattta ttaatttatt cttctgagac aagaaaaaag 48480
ccaccaaagg aaaccaacag cttgctcctc tcacactggg ggaaccatat gagagactta 48540
tctatccctg actttaattt tgacctgagg agagctcctc ttaaggaaaa caaattaatt 48600
caatgactat actacttaat cattgacctt tatttaataa gagatttttc cataggatat 48660
gctgagctgt ctcacttaca tcagttgtgt ctcctgaggt gggtgacagg agaccacaaa 48720
tattgcatag cacacaaatc gttaatagca gctgtatacc aaaccattac ctaaatatgt 48780
agagtacaat tcattctcac taatgtcaga gagcatgcta taaaatggtg aatccggaca 48840
gctgaagata ctgaataata acctctattt tgaacaagtt tacagtgttc caatcagtaa 48900
ttaaattgat acctgatgaa tatatgtgtg tgtatgtatt catagcagag atggttttcc 48960
tgagataagg attttgttat tcggataggc tgctgctgga attgtccttc taccccttgtt 49020
tctttgtcct tagtcatcac tcatacctct ttccactctt ctgccatcac ttttgtcacc 49080
aaagtcatgg tcctttcccc gccgattgct gctgcaggtc tagggcacca agacttaggc 49140
agcactcacc atgtgccaag aactggacca caggtaccat ccagcattgc tcatggagac 49200
tctgtccctt tctgtaggac accctccttt tagctagcaa cccctccacc acctagagcc 49260
tctggacctc tcattttaat attaagaact aggaaaactt accgctgaga ataactagta 49320
caactagaac tggtagagaa atctgggtct cttgggaatg gatttttagg ctttattgat 49380
tagaggtgta ttaataatgc agtgttatag tttcatgaca taacgaataa aaaagttcat 49440
tttggacttg cctttcagct ccctaggagc taaaagacgt atttaatgta acttgtgtgg 49500
tggaaataag ttcttttttc aggcaaaaga tgtgcaaacc catctgggga agaaacatta 49560
aaaactaagg agacagtgtc ctagataact atgttctttt cctgttttag tctaaaataa 49620
tgattagttt tcttatatat cttcatttgt cttggttcct tttagcccaa tttaataata 49680
ttattgcaga tattgatgaa aacctttacc ttcctcttaa ttcatcaaag tacttgataa 49740
aatttataca tagtacatta attgggaggt ttttatgaga ttaattaata taatgaactg 49800
atgttgaaat tatttaaaac ctgaattatt attgtattaa gtaggacact taatacagtt 49860
aatcagttct gtctttattc atttgtgaga atttttggca agctattgtg aatattcagg 49920
gaagggaatg tatttttagc aggaatctta tacctcctac atagaaatga agcatttact 49980
gaaacatcca tgaaacaaaa tgtttctgaa tgtgtactat acacttgtta taagcccctt 50040
ttcttctgta gctatatttt ggagaaaaat ctttgctttg acaaaaaaaa ttatgttgac 50100
ttacacatat attttataac taagcagtgt ttggtttgtg ataaaggata caaaaatata 50160
aaaatgttca gcacacgtaa gtaaggcctt gttgacagtg tgagttatgc tactggatac 50220
tcaaaaggaa cattcagtgt tctcaggtgg tctctagact gtctcaagcc taggaagata 50280
ttttataagc aaaggaataa gagaaggaag attcagattt aatccaagtg aagaattcag 50340
ttttgtgtgc cttatcctgt tattttgaga ggcagccaaa agatgctggt cagcaaggag 50400
aattgtaagt tgggcagcca actctgattt ctcaacctct tagctgtttt cttaaactca 50460
gaatttttaa tgaatttaaa tgtccatatc aggtagactt tggggatgct tttaccagtg 50520
attttcagaa tgttactttc tggcatttct tttcacgtag cattatatta aaaatgaatt 50580
cattcatcca ccttcccttg tccttactaa ttttccctcc tactcccttc ccccttgttc 50640
ttgccatggg gacatgcaaa cactggtggt tgatgtctga gcaaggctgc tgacaggggg 50700
aggaaggaga tgtcaagcag aggtcaatgg cagtgtgccc agcagcctag gaagtaggag 50760
ggaaaagaga gagagacaga gatggtggat gaaagagaaa gccaggatga ttatggtggt 50820
tatgatactt gtcatgctga acacccaatt gagcacccaa taagcacata ataatttaat 50880
catcctctgg cttggatggc agtgttctat cagtgttgac ttcctggttg tgacagtttt 50940
acagtgttag tgtagaagag aatccttgct ttagagaggt acttactgaa gtacttaggg 51000
ttaatgcacc attgtgctgg aaaaagatac gcacacacac gcacacacac acacacacac 51060
actctcacac acacgcacaa atacatccat gtgttaggca gagggagcaa atgaggtaaa 51120
atgttaacaa ttaggaattc tgggtgaagt ggatagaggg actctttgac tgttcttgaa 51180
acttctctat acatttgatc tgtttcaaat tcttcagaaa atcaaactac aaaaacttaa 51240
ttcatttagt gaacatctac tgaacatctg tatattaaat agtgttaaat gaatgtcaat 51300
taaaatgctc aaacacagta gaggttgatt ctcattcaca taagtccatg gtaggtgttt 51360
ttggcaggtg ggtgagtttc tcccttaggg agattgagga acccagactc ctcccaagtt 51420
gcagccccac cgtcttctga ggggatgcat ccatacccac ttcgaagtag catacattat 51480
ttcctttctc attcctttgg ataccagcca caatttattc aaggtagaca gaaaattgta 51540
gtatatagcc atatgccctg acaaagaagg gagaacagat tttggtggac aactagcaaa 51600
ctctgataca atctgttatt aagcactgtg tgtggataga tgctaactag aaggagatta 51660
tcttcccttc agcaaatata aactgaatgc cgtttatttg gttgaaacta agctagatca 51720
tgggagtata gaaattttat aagaagacat agtcacttct gtcagtgagc tcaagaagaa 51780
ttagtatgcg gaatgtaatc atacctacag gggcttgtg ccacttaagt aaaatgaaac 51840
attattttga gtacaattta gcaataaatg tactacgaga tcattaaaaa tcatgtttga 51900
atgttattgt gtcaaggatg ggaaaaagac ttttgggttg tagacttgat aattatagtt 51960
aaaaacagtt tttattcttg tttagtctta ttttttatgt ttaaacatat ttatacttgc 52020
taacatttat acttgctaag taaagactgt ttttacaacc atgacaagaa caaaacatat 52080
tagtaatgca aatgccacat ttcctacaat caactaatca cactaacata tttgcatgga 52140
agaatcactg ggattgatct ggccacgtgt gtagtcatgc ccaaaatgtg aagtccatct 52200
gttttgcaat ttttttaac cactgttatc caaatgctcc ttggattttt tttattagtg 52260
gatatatttt ggaggtcaga caccctcttg gctagatcat cacctttata acaaatatat 52320
atactattct catggaaata tatttagaca ttgccctact gggaattttt ttcaagtaat 52380
taatgtacag cttgtgcaac agcttgatct tggcttcatg gaaataattc actcttagca 52440
gcatctaatg ccacaaagca tttatggatg tcagctcaga acttactttt atttatctct 52500
gagttacttt ttttttttt tttttgagac agagtctcac tctgtctttg gcttgtccct 52560
aacctcttaa cagacttaat attaagctcc atttcactca gtcgttctgt tgtcatataa 52620
atgagacatt ctacaagcat agtttttagt ttctgccaga gcatcataca acattgtgag 52680
ctatgatgaa gataaagacc tagagaagat atttaatatg aagttcatta tctaatattt 52740
ggtatgtgtg gcaaaatagc aatctactgc ttggttctgc tgtaatctat ttacccaccc 52800
atcccatctt tctttcaatt taaaaggata atgattttag tcacgattat acataaaccc 52860
attaccatag gcaataaaca atggggcaaa ccattggtcc catagttgga gtgtggtctg 52920
aagtgtgttt tggtggagag agatctatgt ctggagatag ctaacatgga tttggatccc 52980
agatctgctc ctacctgttg ctgtgcctgt gaccaaatca tgtgatctct ctggtttcag 53040
tttacttgtg aataaagtaa ataccttcat caacacctgt ttttgaatac aatgtttttc 53100

-continued tgtaattttt gcttcttata atgttataat gatcatcctt acatctaaat cttggtttac 53160
attttcatca attcttttgg aaagattgga gaagtaaatt ttggagatgt atgtcggcta 53220
ttaaaaatgt ttaatttttt aattaaaaat taaaacgttg aaaaatcctg atgcaaaata 53280
aatgcattat gcttagtgaa ctcttctcat ttcgaagttt attcaccttc ttgtttttgc 53340
aagtttcctg aaaaatgcat ataaagtcac taagttagca gaactttata aaattatata 53400
actatatata atcttttgat atcagtgaag ccagctgatc ctatagaaat aatgtaggaa 53460
ttataatcac tagcacataa tttaagagtc ctgtggtctt attcatgtta tttaccctct 53520
ctgaatctta catatagtaa gagggttatt atacataata tgtgtacatg tatacaggta 53580
agtaagtata tatgcttatg tgtaaaagca gagttattgt gagagtcaaa tggaaatgtg 53640
aaagtacttt gtagtttttt attactatta ttaattttta ataaaatggt aacattcatt 53700
taataatcat tagttttaac ttcagattgt actggatttc ctctagtatt tcttaagatt 53760
agtgaataaa gtatttctcc taataaatat attgactact gtctttcgat caaacatatt 53820
aggtatattt ttacagtagc atcaggcagt gaaaatttga agctctttat agaggactga 53880
tttatgatga aaaggaataa catgaacaaa tggaattata tgaagcttcc ccagaaatat 53940
ctaagagggg ccaattttaa gaaatatctg acttcttttt catggacatt tcaaaataaa 54000
cctaactcat atggtacagt ttttaagagg gaaaagaaaa aaccatctga gaatctctgg 54060
aattctgccg aaagtatcac ttggcatttt attctacctt ctggatgcag ttgattgaca 54120
gtagtgttat gatgccaggg gtatagtgac tagaaaaaga aaaccaggga attcagtgtt 54180
cttgctcatg aagaacagct tggttcttta aaaacaatga gattttgcca ccccatctca 54240
caaacctatg atttgtgaga acaatccctt ttgtgttgca agacttttac atttctcttc 54300
ccacactata ttagaagaat aaacattgct tcataagtac cgattgatag tctcatttca 54360
tatttttaaa atagagttac tttaaggtta aatttttcat gtagattaaa atgactaagt 54420
aaccattcac atatttcaaa taaaatatat ttttactaca aaaggaaaat aactagattc 54480
ttaagtgtta tagtcaagtg taattgagta atatgaattc taaatgaatt tctaagatct 54540
gctcagcttt cactacttta ggaaggaaca acttaagaaa aattttaata aagatatctc 54600
ttcacacaca tggcagtgtt gtacttagag aacatgaccc aaaatttttt atgactgcat 54660
attgaattcc tgatactctt gggaagctcc aaaagcacca gtggagtttc cagatgtaac 54720
tgtggctgca gacccgccag tcccggtgtt ggaagggatc attataggct cttgtgtgca 54780
gactcatctt cagacccaga ggaattaaat aacttgccca aagtcgcaca actttctcat 54840
ggtaggttgg gcactagaat aaatattgct ttttcttaag agttttagcc tccgtattat 54900
gaaatcttct atgttctgct gatgatatct cctttcttca tctgttttct atttttaagc 54960
aatggaaata caaacttgca actccccatt tccaacacaa cttagaaaaa acaatattta 55020
aagaaaaaat tacaggcatc tcatctcctt tacctgacag atgcttgata gtaatggcct 55080
ctagataggg atgacatcta atataaatgt gtcctttcaa gtcaagcttt ctctgttcat 55140
tagtagaaat attgtatatc aagtgtgcaa aaattttctt caacagggag ctttgtttcc 55200
ctccttttat tataacaatc tgagctttgt ggtcccaggg tctcctagtg cctgtcttta 55260
ggtctgttta ttcacatgaa gaaagcatgt catatagtat tatctaagac tcaggctgct 55320
tatgcatgat gacagaaggg ttcccaggca caaacattca tccatgcatt catccatcca 55380
cctattcatc cattgatttg gctgataatt attgactact gttgagttgc cctcagattt 55440
agtttctgtc cttctgccat ggggaaatat ggggttaagc cacaacatac tcttctcttc 55500

```
tttttctgca ccttcttagt atatttagtt ccattttgtc tagccctgcc tctgacttct  55560
ttgttgtact tcaggttttt tatcattgaa agttatttct ggatcataga tcattctctt  55620
ggtcactttg cttgttcact tataaaatta attcagaaaa aatgacccac agtaattacc  55680
gtaaatcaca gaccataaac tataatactg tatattgtat tatagtacag aaatatttat  55740
actttaaaat gttttaaata tagatattat aaaaagatat gtctcatata agtaatataa  55800
atactttttt attacctctt ctctccctat tctccaggcc agtgttttaa aaatccatct  55860
ttatatgtcc atcctggaaa aaactcatga tcataaatga gtttctcaat agagtttata  55920
agcccacagt tgaaacacaa ttgtcttagc atccatttag ttgtcatact tttaagattt  55980
aatggcaaat attatgtttt gtttcttcaa aagaaatatt ttaaaatttt agtaaaggca  56040
gttagagaag gtagagataa tggactgttt aatcctactt ttcatcccac aagtgaacaa  56100
aaaaatgata aaacattttt cccaaaatgt agctttaact atacttaaat ttggactaaa  56160
atgggagata tcttttctac tattgaaaag ccgtgtctgt agattaatgc taaaatcggg  56220
tgtaaaagca aaatttgttt ggcttgattg ccaatggccc attcatttgg ctacagaaac  56280
aatagcacat agcaacagat aatgatgtga gatcacctag ctcaagtaag agtgtctgat  56340
ccgtcaaaaa tatatacatc aagattcaaa agaaatgtgt gtttctcaa gtcatctctg   56400
taaaaataca ttaaatagag gaatagaagt ttgactttga aaatacattg cagacccaat  56460
ccgtctttcc tattttctgg tgaaaagtat caaatatgtg gaacctggaa ctgctattct  56520
ccttcttaaa aatctttctt aatattctat tgataactgg tgcaagccta actttttgtc  56580
ttacccgatt cttctcacac caaagtgata ggaccttcag gtagcctttg gatagaagat  56640
aaataataat ttaactattg atggaagtta gtattagaat tagacttgga agtctatgga  56700
ataaaatgat tctacaacaa tttgtacttc agacattagt ataacaaaac atgtttgccc  56760
gtgcatgcgg aaacaaccaa tttcatgtgg atgcttatat tcacaaagga gtaaccacct  56820
ggggtttccc actgttgctc cagagaaaac tagcagcagg agaacttctc tgaaggtatc  56880
aagacatctt taaaaaacac ttgttaagtg ttggttcagc taaagcaggg agttttcagt  56940
tagtaatggc ttttaaaaat taaaacaagt ttagcatgta ggtcattaac cttgaatcac  57000
tgtcatgatt attattaacc atctgttctc aaatcgaaag atatttttct tttctagatc  57060
acatttattc tcacattgct caatttcact atatatcaag acatgaaaac tgtaaaaatc  57120
acaccttcta cattattatt tttattgaaa aattcctaat gaaacagtgc gctctgggat  57180
agagaaagga actaactgac attttgcttc ttaacttgtt tttatgcaag ttctaagtgg  57240
tttctggcca tgtacataaa agacaaatat ctggaaaaaa aactagcaga agtcagttat  57300
ttggctctat ctactttgag aattatgtta tataaatgtt aggaaatttt ttgtaatatt  57360
cttatttaga aatgaaatat aaaaagtttt aaaaatatct aaggacagta tacagtccta  57420
aagtaaagct gttaggtaaa tgctacacaa tcctcttatt acagagtcac ttacctgaga  57480
atataagaag agggcctctt gtttaagagt aaatgtgagc tgcaatcagg attctgcact  57540
catttggaca cttagttttg tttttccatg actggtgttg cctgttactg agacacctac  57600
ctgtcatgtg accacagctt atgttacaat gtgtctagtc agacttagag atgtgtgaaa  57660
gagcagtacc tagacgggaa actatgggtc tataaaggtt ttgccttctt gggcggagtt  57720
caaactagga agccacaaaa cttccagttg cattttcaca gattaatgaa atatatttta  57780
cacttttcct gaaagatatt ttatttgtgc aaaccttgtt acaaagtaca gccagttgat  57840
```

-continued taatcgatga agtgatttgt agtggattct tatattttgt gtaagggtat atgtgaggcc 57900
ctatatatga ggctttctat ataatgaagt ataattcagt tcagcatttc aattcagcaa 57960
tcacttattg ggcctctact cagttgcctt cagggcttta taatttaatt gataaaggga 58020
ggttaattaa ttaattataa caacagatcg cttaatagtg taactactaa tttaattaat 58080
gacaaataac aatacattaa aagaaatgca ttaataaaaa taatatattg gtgttataga 58140
caataatttt ctgattaact ttattattat tatttcaata gcttttgggg agcaggtggt 58200
ttttggttat atggagaagt tgtttaggta tgatttctga gattttggta cactcataac 58260
ctgagcagca tacactgcac ccaatgtgta gtctttcatt cctcaccttc ctcccaccct 58320
tcccctcaag tctccagagt ccattatatc attcttatgc ctttgcatcc tttagtttag 58380
gtggcagtta taaatgagaa catgtaatgt ttggttttcc actcctgagt tacttcactt 58440
agaataatgg tctccaactc tatctacgta gctacaaatg ccattatttt gttccttttt 58500
atggctgagt agtattccat agcatccaca cacacccccc tatgctttat atatatatgt 58560
aaatatatca cattttcttt atccactcat tggttgatgg gtatttaggc tggttccata 58620
tttttgcaat tgtgaattgt gcagctataa acatgcatgt gcaagtgtct ttttcatata 58680
atgacttctt ttcctctggg tagataccta ggagtgggat cgctggaaca aatgattgtt 58740
ctacttttag ttctttaagg aatctccata acttttccat ggtggttgta ctagtttaca 58800
ttcctaccag cagtgtaaaa aaatgttccc tttttaccac ttccatgcca acgtttattt 58860
ttttattttt taattatggc aattcttgca ggagtaaggt ggtatcacat tgtggttttg 58920
atttgcattt ccctggtcat taaagatgtt gagcattttt tcatatgttt gttggctgtt 58980
tgtctatctt cttttgagaa ttgtctattc atgtccttag cccacttttt gataggatta 59040
tttgtttttt cttactgatt tgtttgagtt ccttgtagat tctggatatt agtcctttgt 59100
cagatggata gtttgcagat atttctccca ttctgtgggt tgtctgttta ctctgatgat 59160
tatttctttt gctgtgcaga agctttatag ttttaggtcc catctattta tctttttgt 59220
tgttgttgca tttgcttttg gtttcttggt catgaactct ttgcttaagc cagtgtctag 59280
aagagtttta ccaatgttat cttctataat ttttaaggtt ttgggtctta gatttaagtc 59340
tttgatccat cttgagtgga tttttgtata agttgagaga tgaggatcca gcttcattct 59400
tctacatgtg gcttgccaat tatcccaaca ccatttgttg aataggatgt cctttcccca 59460
ccttatgttt ttgtttgctt tgttgaagat cagttggctg taagtattta gctttatttc 59520
tggattttct attctgctcc attgatctac atgtctattt ttatagtagt accatgctgt 59580
tttcctaact atagtcttgt agtatagttt gaagttgggt aatctagtgc ctccagattt 59640
gttatttttt gcttagtctt gctttggctg tatgggctgt tgttttgttc catgtgaatt 59700
ttaagatttt ttttcttgtt ctttgaagaa tgatggtggc attttgatgg gagtcgcatt 59760
gaatttatag attgtttttg gcagtgtgct cattttcaca atattgattc tgccaatcca 59820
tgaataaggg atgtgttttc attagtttct gttgtctgtg atttctttca gcaatatttt 59880
gtagttttcc tgtagagatc ttccacctct ttggttaggt atattcctaa gcattttttt 59940
tttttgcagc tgttgtaaaa aggctcaagt tcttaatttg attctcagtt ttgttgctgt 60000
tggtgtatag cactggtact gatttgtgta cattgatttt gtatctggaa actttactga 60060
attaacttat cagatctagg agctttttgg atgagtcttt aggttttcta ggtatacaaa 60120
catatcatcg gcaaagagca acagtttgac ttcctcttta gcagtttgga tgctctttat 60180
ttctttctct tgtctgattg ctctggctag gatttccagt actatgttga atagaagtgg 60240

```
tgaaagcagg cattcttgtc ttattccagt tctcggggga aatgctttca aattttcccc  60300
cgttcaatat aatgttggct gtgggtttgt cataagtggc ttttattacc ttaaggtgtg  60360
tatcttatat gccagttttg ctgagggttt taatcataaa gcaatactga attttgtcaa  60420
atgctttttc tgcatctatt gagtttatca tatgattttt gtttttactc ctgcttatat  60480
ggtgtatcac atttattgac ttgcatatgt taaagcaacc ctgcatcccc ggtatgaaac  60540
ccacctgatc atggtggatt atctttttga tatgctgctg gattcattta gctagtattt  60600
tattgaggat ttttacatct ctgttcatca gggatattgg tctgtagttt tctttttttg  60660
ttatgtcctt ttctggtttt gatattaggg taatactggc ttcatagaat gatttaggga  60720
ggattccctc tgtctctatc ttttggaaca gtttcaatag aatttgtacc aatttttctt  60780
tgaatttctg atagcattca cctgtgaatc catctggtcc tagacttttt ttgtttcctg  60840
acatttttc tattattgtt tcactctcac tatgcattat tggtctgtta ataatttcta  60900
tttcttcctg ttttaatcta ggaggtttgt atatatgcag gaatttgtcc atctcttctt  60960
ggttttctag tttgtgtacg taaatgtgtt cacagtagtc ttgaataatc tttttattt  61020
ctgtggtatc agttgtagta tctcccattt catttctaat tgagcttgtt tagatctttt  61080
ttcttgtttt cttggttaat cttgccaatg gtctattgat tttgtttatc ttttcaaaga  61140
agcaggtttt tgtttcattt atcttttgta ttgtattttg tgtttcaatt ttatttattt  61200
atttatttat ttttattttt attttttgag atggagtctc actcttgtta cccaggctgg  61260
aatgcaacag tatgatcttg gctcactgca acatctgcct tccaggttca agtgattctc  61320
ttgcctcagc tgcccgagta gctgggacta caggtgcctg ccaccacacc tggctaattt  61380
ttgtattttt agtagagacg gggtttcacc atgttggcca ggcaggtctc aaactcctga  61440
cttatggtga tccgcctgcc ttggcctccc aaagtgctgc gattacaggt gtgagccacc  61500
acactaagac tcaattttat ttatttctat tctgatcttt gttatttctt ttcttctgct  61560
gggtttgggt ttgctttgtc ttgtttttcc agttcctaga ggtgtaagct cagattgtct  61620
atttgtgctc tttcagactt tttgatgtag atatttaatg ctatgaactt tgctcttaac  61680
atggcttttg ctgtatccca gaggttgtga taggttttgt cattattatt gttgaattca  61740
aatattttta aaattttcat ctttcttgat ttcattgttg acccaaagat cattcaggag  61800
cagattattc gatttccatg tatttgtata gttttgaggg tttcttttgg agttaatttt  61860
taattttatt ccactgtggt ctgagagaat acttgatata attttgattt tcttaaattt  61920
attgagactt gttcatatgg tctgtcttgg agaatattcc atgtgttgat gaaaaggatg  61980
tagttgttgg gtaggatttt ttgtaaatat ctgttaagtc catttgttct agggtatagt  62040
ttaagtccat gtttctttgt tgactttctg tcttgatgac ctgtctagtg ctgtcagtgg  62100
agtactgaag tcccccacta ttattgtgtt gctgtctatc tcatgtctta ggtctagtag  62160
tgattgcttt ataaatttgg gagcccaagt gttagatgca tatacactta agattgtaaa  62220
tttttcctgt tgaactaatt attttatcat tatataatgt ctctctttgt cttttttaat  62280
tgttgttgct ttaaaatctt ttttgtctga tataagaatt gctattcttt ctcactttga  62340
gtttccattt gcatggaata tctttttcca cccctttacc ttaagtttat gtgagtcctt  62400
acgtgttagg tgagtctctt gaagacagca gatacttggt tgatggattt ttatccattc  62460
tgccattctg tatcttttaa gtggagcatt taggccattt acattcaaca ttagtattga  62520
ggtatgaggt actgttctat tcatcatgat agttgttgcc tcaatacctt cttgttgttg  62580
```

ctgttgttaa ttgtgttatt attttatggg tcctgttaaa tttatgcttt aaggaggttc 62640
tattttgatg tattcaagtt actgtttcaa gatttagagc tccttttagc atttctcagt 62700
gctggcttgg tagtggcaaa ttcagcattt gtttgtctga aaaagacttt atctctcttt 62760
catttatgaa gcttagtttc actggataca aaattcttgg ctgataatta ttttgtttaa 62820
gaggctaaat atagggccca atctcttctg gctagcaggg tttatgctga gaaatctgct 62880
attaatctgc tatgttttct tttataggat acctgatgct tttgcctcac agctcttaag 62940
attctttcct tcatcttgac tttagacaac ctgatggctg tgtgcccagg tggtaatctt 63000
tttgcattga atttcccagg tgttctttgt gcttcttata tttggatatc tagatctcta 63060
gcaagactag gaagtttttc ttgattattc cctcaaataa gtccttaatg accccactat 63120
ataacatgaa atatctgtta ttggtactga ggtgctggcc acaaacaatt ctgtgtgtcc 63180
tgaaaactct tcagaatatt cgtcatcttt agcacttgtt atcttagtgt ttgggcttgg 63240
cttagagtga tacatctcat aacagggcaa cagaaagaac caggaaccaa gatttatata 63300
acataagtca gtaaaactag aggcaccaga ggtttacatt tacattaggt tacatttttct 63360 aacaggtagc aaagcacatg aatgaagttc agtggaaggc cttcctcagg aatccagtaa 63420
aaaccaaaca tacacacaca cacacggaca tccgtgaggc aggaagggat gtccactata 63480
gtacagacaa gcatcctgga aggccatcaa ggagtaggtg ggtttcagtt gcctcaggaa 63540
tgtggcatgg acccaaacta agtgagtaca gatacttgtc attgaggaga agattcaaaa 63600
tagcatccta ggtgtaaaaa ctgaggcacc tggggcaggg gaactaggtc tctggaatgt 63660
tggcttaaaa gcacccctct caggaaaggc ctcatatgcc atgcaggggg ttatatatgt 63720
gttgtgggac acagatggca aggagataat tctatgcacc aggctccact actaacaggt 63780
aaacagacca acattaacag agacttaggt aaaaaggtag gtgcccagtg gtcagttctc 63840
aggcacttcc aagatgcacc taacagaaat gtaacttggt gtctattgtg tcctaggtct 63900
aacaactgaa gagaagtgaa ttagtacctc ttgtggacag agaaacaggg gcagagaccc 63960
attacaaagc tgtctcagat aggcatttga agctgtttaa gtatgtagag gcttaagtca 64020
ggctggttct gaaatgtgag agagggttaa gcttcatggg aaatcagcag ggtagtttgc 64080
tattttttat tataaccaat ctcacaatag tttgggacat caaatatcaa attgttggga 64140
atatttatcc atattagtct ttttgccact aatatttaaa aatagtttac aatatacaac 64200
aaaaagttgt aaaatttcca tctccactta atcgatctta tgtaacccat acaatacatc 64260
aaatgtcctt tccccacttt atgtttttat ttgctttgtc aaagatcact tggctgttag 64320
catttgggtt tatttctagg ttctctattc tgttttattg gtctgtgtgc ctatttttat 64380
accagtgcca tgctgttttg gtgactatgg ccttatagta tagtttgaaa gcaggtaatg 64440
tgatgcctcc agatttttct ttttgcttaa tcttgctttg gctatgtggg ctctttttttg 64500 gttccatatg aattttagga ttgtttttttc tagttctgtg aagaatgatg gtggtatttt 64560
gatgggaatt gcatttaatt gtagatttct cttggcagta ttacccaggc ttttcttatt 64620
ttggcaccct gtgctgctgt ctccttttcc ttctttctgc ttctcttaac caactgttac 64680
ctacacttca atactttctg agggcaattc atcctccagt aagtctccct gaatcttctc 64740
ttccttccct ggcttattat atatccttcc tcttggttcc catagcacct atgcacactt 64800
ctgtcattgc acttgccaat ttgttttata atgatctgct catctgtctc ctcacttaga 64860
ctatgagctc actgagagca atggctgttg cattcacctt atatcctcaa caccattctg 64920
aaggcaagag aaagaatacc cagaggtgga gctgggaagc tggttgtcca agtagtgaat 64980

-continued

```
gactctagtt tgaattgaac tctatagcca gtgggcaatg tggatgtgtt gacagttttt  65040
taacagggga ctagtgaaaa cacattttgg gtttagaaaa aattgcaagt ctgatgacat  65100
acataggaga agagattaga gataggaatt tcacttcaga aatttaacca caagagcaag  65160
tgacagatca cggaagtctg aaccagacta taaatgtgag aatagagaaa aaagttaaca  65220
atttgggtgt gaaagggcga gggagagagg tgtgaagaat gactaagtgt ggatctgttt  65280
ttaaggattg aatggaaatt tgagcatttt agctaatcag gcctaatatt gagcaaagca  65340
aaactcttgc aaattgttat ttcaagtgtg ggctgagaaa atgaaaaaat ataaattctc  65400
acgttataac ctcttccgtg tgtctgattt gatagaatcc agccccattg cctccaaatt  65460
ccattgcatc ttagaccagc aaacacaagt gaattctact taaccccaga attctgtatg  65520
aaaatcttac tgcctttttt tttctaatca tgtgtcaaag tgtgggaaga acttttattt  65580
atgttttaat aaattgtcag tataaccatt tttacttgaa aatattataa tttttcaagt  65640
aaacaaattg tttctctaag ttgaaaattt tatgatggaa taaaagtatt tttcctcaaa  65700
acacatagaa attttacaac aatattttag agttaactaa atgtttcttt agtagtttag  65760
tcacttaaaa agtgatatga ttatgaaaat acttaaactt tgtcttttaa ctatttctaa  65820
taatgctatt ggtataattt catattttta tactgatctt ttctccaaac tttagtaaaa  65880
catacttctg taaacccctg cccacaaaac tgaagtccac atttacttct gaatgactga  65940
taagtttgta aaagtatgca tgaatttcgt tattaaatta aagtttttat tatattttat  66000
gcacaatggt ataaattatt aaattaattt tcaagcttat agaacattga taaagattgt  66060
cattagaaaa ccctgagttg attgttatac attacataac ctttcattgg tggattagtg  66120
aatatgttat agggtgacca tgaatccaaa gaatcaaagc tggctacagc aaacagaggg  66180
tcaaaaggat atggaactat gcatgatcca gcaaaacact caatatctgt tttcctggaa  66240
tgttaaaaga caaagaagaa aacttgggga acactagatg catatagttc tggttcttta  66300
agaataaaaa tatgggccgg gcccggtggc tcatgcctgt aatcccagca ctttgtggga  66360
ggccaaggcg ggtggatcac aaggttagga gttcaagacc agccaggcca acatagtgaa  66420
accctgtctc tactaaaaat acaaaaaaaa attacaaaaa aaatacaaaa aaaaaaatag  66480
ccaggtgtgg tgacaggcac ctgtattccc agctacttgg gaggctgagg caggagaatc  66540
acttgaaccc gggaggcaga ggttgcagtg agccaagata gtgccactgt gctccagcct  66600
gggtgacata gtgagactct gtctcaaaaa aaaaaaaaag aataaaaaca agaatggtca  66660
gagtcctagt accttgtcca gtgtagtgct gccttgagat tgcattgcaa tctgtctgag  66720
agatagtaaa agaaagtgat accttcctta gccctgtttc tctttagact atgctttccc  66780
ctctccaagt taatatctct cagtctaaag cctgggaaaa ggtgccaatt ttgtttttct  66840
ttcttcctca cacctcctag aagttacact gggacactat tacttttttc caggctttgg  66900
ccatgtgtat tgttttggag agtcaacttc cttttttctt tcattctgca aatagttttg  66960
agctgtcact ctgtactagg tgctataaaa cttacaggtg cattttacat gcctatttcc  67020
tataggccac gatttaacaa aatgttcata aatgagaatt aggagtgcat gtattgaatc  67080
accacacatt aactgaacag ctttcattgg ccagagacta tattgacagt ggagattcaa  67140
agataaacta gagaaatctc atgcttaaat aactttctat aataaattat ataagagaag  67200
taggttcagg gatcttggga gctcagaagc aggatgagtt aaacaaaagt tggattttgc  67260
ctttagcttg gtttcattat cctgaaggaa gagcctgaaa tatagtgtag ggtgcaagta  67320
```

gtatatgtgg gtggcaatct cgggaaacag gagcatgtga tgaataagga gaaaaagcca 67380
atataaaggt actgcattga gggcaatgag ggctctaatt ctctgcacct tctcaagcat 67440
tgtgcagatt ggttttctgg attatcagcc tgaaggacaa aacgaagaaa cagccattag 67500
ctcctgtctc ccattgtctg agagctgcca ctaggatatt aacttcctga aattctgcag 67560
aaatctcctc ttactttggc actggagatg cccatacgca gaaagcaaaa aggcacagca 67620
tatttaagga agctcataag aaacagtgca tccagaagtg gcgagaattg gaggaatgga 67680
catgagactc taagaaccag cgcctttgat gttccttttg atctgttatg tagctcttct 67740
tgtacacagg tgagcaaagg catgctggac aaatggattc acatgtgcta aagcatgggg 67800
caaaaaccac atattaattc aggaaaagac aagatgcgtg gccctctctg tctctgtcta 67860
agggtgaatt aaagagggga tatatgtaca gagtggcagg gcaggacttg agataagaag 67920
gctaggtggg tgctctcatg ctagtagcat tatagtacag gtgatgagaa gctcctgaag 67980
aatcatctta acatttgtat tttagagcaa cagtattgag ttctgactta gagacagcaa 68040
aactaaagac agaaagacta ttttgattat taatgatgta gatataagaa tatcgtcaat 68100
gtgaactaaa gcatgaagct acttatgata tatcattaaa aggatttaac tgattggaga 68160
caaacgagag ggatggggaa aagaattcat ttgtttttag ttgctctttt tttcctactt 68220
attcctttgt tccgagtgtg aataaacttt gtaaactttt atactaaaac attctgctca 68280
ttcatactta tttctttgat gaaacaagga aacccttgta tagttataaa cgtgtgaatc 68340
aatttaaata ttaggaaatt tttttaaata aagctagttt tctgaagggg aaaaacttgg 68400
ttcaattttt tgctggcaat ctgctttgtg atttttgaac atgatatcta catctagact 68460
catgttttgc tagctggaat ttttttcaa attaacgcta ccattattat atgctttact 68520
atttagcttt tgcagccttg gaaatctatg attaatacaa ataattctct atggcaattt 68580
taaaaataca tgtaaaagcc ttcaatctac attgctactg tgtcgtagca caaaaaaaga 68640
aaatgtgatc aaattttaat aaaatctaca atttattccc ttctaaatac agtcctagct 68700
caggagaaag gaagctattt gtatttttca gaatcaaatt tccctaaatg aatatagaga 68760
aagaattata actgaaatat tgttgaaaca gtggtcatct caaatctgaa ggtcattcca 68820
aaaaagtttc tgagttttca ttgcctcaat ctaaaagttg gcctttttgg taatagatga 68880
aagtaaaata attgaaaggg tctgttgcag ttttggaata tcttgaaaat atagtagagt 68940
gaagccttct tcccttaaat aaaagacaag ttgctgattg ttttctttct agccagataa 69000
gaataatgcc ttctttctct tgttagtctt aacacctcac ttgttactat gtgtcagaaa 69060
ggcgagacac cataaatgga gatactactg atggaggtca tctgacatgg ggctggtagg 69120
cagtgggaag actggtatgg acacaggtgg cttaggggtt ggggaatgat atggaactaa 69180
ggaaatgata attagcagaa cccagtgtgc atgtgtgtgc attcgtgtgt ccgtgtatgt 69240
gtgtactgta gcacaatgca agaaagaaaa aacaaggcag acttttcata atttcaggga 69300
taaataaatc ctttatcact tcatgtagaa tattggctac ttggaggtat atctaaacgt 69360
aaatatataa ctatataact acatgctaat taaaaacata caaagaagaa gtgcctaaag 69420
aattacaaca gaaagtggca tagtgattat tagagttaat ataatataaa taaggccagg 69480
catggtggct catgcctata atcccagcac ttttggaggt caagttgcag ggatcacttg 69540
aggacagggg atagagacaa gcctagccaa catggtgaaa cccatctcta ctaaaaatac 69600
agaaattagc tgggtgtggt gatgggcgct ggtaatccca gctactcaag aaactgaagc 69660
aggagaattg cttgaacccg gaagctgggg ctgcagtgag ccaagatcgc gcactgcact 69720
ccagactggg tgacagagaa agacccggtc tcaaaaaatt aaaaaatagt ataaataata 69780
tttcaaaaca caagtctgtt aagataaaag gtacagagga atggtgagat gacttttta 69840
tttgtgtgat aagggactgt tttctgtgat tgtgagaaag accaggagtt aagaaaaagt 69900
ggccatcaat aaatcagcca cttatgggga agaaccataa accactctca gatgaaatac 69960
aaatgcagtc attatttaat attattggaa tatttgtatt agtttttggt atgtgctgct 70020
agtgctggta cattttagta gtcaattaat attttgttaa tcttaatttc taactaaatt 70080
ccagagtgaa atggaaataa taatgaaaaa attttattta caaaacagat tttgtttttt 70140
tctgttaaga atgatacaca gttgtccttc agtagccata ggggattggt ttcaggacct 70200
cccttgggta ctaaaatctg cagatgccta agcccctgtt ataaaatggc ttagtatttg 70260
tatataacct atgcacatcc tctcatatac tttcaatcag gggtccccaa ccccagggcc 70320
atgaccagta ctggtccata gcctgttagg ctgttcgata ccaggctgca cagcaagagc 70380
tgagctcctc ctcctgtcag ctcagtggtg gcattagatt gccataggag cacgaaccct 70440
attgtgaact gcacatgtga gggatctagg ttgtgcgctc cttatgagaa tctaatgata 70500
aatgtaatgt gcttgaatca tcccaaaacc attccccttc ccctcaccat ccctgtccgt 70560
ggaaacattt cttccagaaa accagtccct ggtgccagaa aggttgggga ctgctgcttt 70620
aaataatctc tagattactg ataatgccca atacaatgta aattctatgt aaatagtttt 70680
tatactatat tgtttagaga ataatgaaaa gaaaaagtct acatgttcag tttaagtgtt 70740
gataagtgtg tagagaaaag ggaacccttg tacattgttg gtggaaatat agattggtgc 70800
agtcattatg gacaatagta cggaggttcc taaagaaatt aaaattagaa ttacctaaga 70860
cccagcaatc cctcctctgg atgtacccaa aggaaataaa atcatcacct cataaagata 70920
tctgcactgc tatattcatt gcagcattat ttacagtagc caagatatgg aaaccaccta 70980
ggtatgtgtt ggtgcatgaa tggataaaag aaactgtggt atatgtatat acaatggaat 71040
attattcagc cttaaaaaag gagaagaccc tgtcatttgc cacaacatgc atggacctgg 71100
aggatattaa gctgtgggaa ataagtccaa cacacatcca cacacaaaat tgcataatct 71160
cacttatatg tggaatctaa aaagaaaaag ttcaaatata aagttagaat aaaacagtgg 71220
ttaccggccg gatgtggtag ctcacgcctg taatcctagc cctttgggaa gccgaggtgg 71280
gtgaatcacc tgaggtcagg agttcaagac cagcctgacc aacatggtga aatcctgttt 71340
ctactaaaag tacaaaaatt agccgggcat agtggcaggt gcctgtaatc ccagctactc 71400
aggcagttga gaaaggagaa tcacttgaac tcaggaggca taggttgcag tgagccgaga 71460
tggcgccact tcactccagc ctgggcaaaa gagcaaaact ctgtctcaaa ataaaaaaac 71520
aaaaaacaca gtccacacac tggttaccat gagtgaggtg gcagggagga gattgggaga 71580
tgtagatcta aggatacaaa gtagcagata tgtaggagga actaaaaagc tgacatgcag 71640
gatgacaact atagttagta atagtgtatt gtattcagga tttttgctaa ttgagtagat 71700
tatagctgct cttgccacag gggaaaaagt gggtaactac gtgagataga caatggatgt 71760
gttaattttt gtcactataa taaccttttc accatataca ttcatcttat aacagcatgt 71820
tgtttactgt aaatatatac aataaaattt atttttaaat atctgagtat gatttgatga 71880
tttgtgaaaa tagagtgaat tataataatt ttaaatgtaa gttaatgtta ttagaaaaga 71940
aacagaaaga acataccaca cagaaagtct gtctgaagga tctttgtttt ctccaccaat 72000
acaagtgttc attgattcag aggtggatta tgagatatga ccataaaaca aaaatttcaa 72060

-continued

```
gggaaatata ttttattcaa tgaaaaattc tcaacacaac tgttatatgc cagtaaacac  72120
tatatctttt aaataacagg tcatatctat tatatttaaa attcaaggag agactacatt  72180
agagatgcta ttagatcaac ttctaatttc aaagatttct aagatatgga acagttactc  72240
cttatacaaa ttaaaaaagc aaatgctgaa gaaattcagc tacatggata caccatgagg  72300
tggaaagatg ctccataact cttagttaaa ctgcactaat tacacataaa aggaaaatgt  72360
ttcatttcac tgtaatttgg aaaccaaaga aagaaaagac tgaattttta catactgtta  72420
aagagattgc gtatctgttc taagtttaag acagaggcaa aatgtatttt attcatttgt  72480
cctgcaccgt ttagaaataa aattcaactt ccttttaatt tttttaaga ataaaaaact  72540
cagtctaagg aaagtcttaa agttttcatt ttaagtgatc cactgttcta gaagtttaat  72600
attttgttta aaatgtttat gttctgtatt ccaccaagtc tagttttaaa acaaaacaaa  72660
caacaacaaa atacttctct aacttggagt ttaaggtgaa agaaaccaat tacgtggttt  72720
ggaaatgtca cacttttcat ctcttttta aaaaaatttt taattcagga cagaaattgt  72780
atggatttag tgtaagtctt gggatctcac aagtgtcagt atttcactct cctccatatc  72840
ttgatagcaa taacttgaaa taggatctca gtagctcaag caatactggg ctctgagagt  72900
tggttaaaaa ttatttggct gagcgcctgt tgctgaggga agaactaatc tcgagcatat  72960
ttttggagcc aaataccaaa ttgtttgtgc ttagcaacac agcaccaggc ttgcccttca  73020
gaatgattct agaccaaatg ccagaaatgc tctggttctg actacagagt tctattcaca  73080
aatgacagga ggcaagaggt cctcctcact ttcagaagaa aggtcctttg ctttcttagt  73140
caatggtagg aaaaccattg tggttttcat tgcattacat aatttttaag gtgattactt  73200
caataagaag tgctctgtgt atatgtgtgt ttatagacgc attttttaaa cactggagaa  73260
tttctgaaag tagtacaaac cttgtaatgt caagtagatg tgggaaaaag ggagtttaca  73320
acattctctc ctgacattgc tctcctttgg catctgcatt tttaaaatgt taaaaatgtt  73380
taaaaacgtg tgcttaacac ttaatttggt gatagttgct gttaccaagg caactctgta  73440
actccaccca gataaaaata aatcttgaag atgagtttct gtgtctctga gcaaatattt  73500
ttgtgaatag tagaagcaga gaaagttaaa gatacctgag cttttgatct ttactagttt  73560
tatagatatg tttatagtta tacattttta ttcatacatt ttagataaat aactttgtaa  73620
agcaattgat tcttcttgta aaaatcaagt atattcttaa tagactgata aactttcttt  73680
ttttgagaca gagtcttgct ctattgccca ggctggaata cagtgccatg atcttggctc  73740
actgcaacct acctctgcct cctgggttca agcaattctc ctgcctcagc ctcttgagta  73800
gctgagatta caggtgcatg gtaccacacc ccactaattt ttgtattctt agtagagatg  73860
gggttttgcc attttggcca ggctctgaga aactttttaa ggtctctttt gcagccagct  73920
atttgtctac cttatttcat tcttaatctc actagccaat attttttctg tttaagtgct  73980
ttcagcaaat attaaatgct tgtgccttca gtcttatcct gtggaaacac tggtaatgac  74040
aaaaacacat atttcaacct aatatacaat agaaacagaa tgccagttat tcatggagga  74100
gaagaataga cttctgtatt taaaataaca ttttgctctg tgttttaaaa tcattcttcc  74160
ttcatcaatt gtaagcatct tgactataat ttatacacct aaagataaat aattcagtag  74220
caatgataac tgaaaacagg acacatacaa tgaactagct aaattaccat acattctcat  74280
ccatttcaaa aatagctctg tactttttc agattttgtt agaagaatat tcaatacaaa  74340
tttttattca atgaacactt cagatgtcaa gattgttacc cacatggaca acagtaacct  74400
aggtaaagat tctgcagcca ggcgtggtgg ctcacacctg taatcccagc actttgggag  74460
```

gctgaggcgg gcagatcatg aggtcaggag atcgagacta tcctggctaa catggtgaaa 74520
ccccatctct actaaaaata caaaaaatta gccaggtgtg gtgtcatgtg cttgtagtcc 74580
cagctgctcg ggaggctaag gcaggagaat cgcttgaacc cgggaggtgg aggttgcggt 74640
gagccgagat tgcaccactg cactccagcc tgggtgacag agcgagactc tgtctcaaaa 74700
aaaaaaaaaa aaaattttat acctgggctc tgtgctcacc agcagaaggg gtaacatggc 74760
ttcttaggac aaccttactt gaccatttac ttctttgaca ctaggggtat tcttagatca 74820
gcaggtcctt ccctccactt atgcacatga ggctcacaga gagtctggga ggcagggaat 74880
ttatgattgg aaacagtata ctttttatct aagaaattat taatgtcact gcattcaagt 74940
gattaacacc atcaatatct tcaagactaa ggggattaca tgatgtgtaa aattagaaaa 75000
ctgtcatcta ctagtggcta ggcactttaa ttatattaag catgcaacaa gagaactctt 75060
caaatgaatc catctctcct ctgtattatt tccaaccctt ggatccccat ctgtttctgc 75120
agacaacagc tatgctgctg aatgtcttaa tggtttgctg ccccaactag cttcaagata 75180
ctgcaggtca agcatagcat cttactcttc cctgcatctc cagcacctct cagaatgttg 75240
gtcacataga agatgtttgc tgaggagttg aataagaata tgtacaaggg acacaattag 75300
cattgtttaa aaaagatgta acaagatagg gtaaaggaaa gctttggagg ataaatcttt 75360
agaacaatca ataatatctt ctcctctgtt ggttagttgc ccttcaatct cagccactga 75420
atcaaataca acataattac tattctgata tgttcttgaa tcgaatatcc aataataaga 75480
tattcggatg catagccatg tctaatatca aagcccatgc ttttcgctat tattgtactc 75540
catacattag cttccaaatt tatttgcaat ccaaatatta aaagcaagtc ataagcttag 75600
tatcgccaat gtgatactaa gtatccactt actaaacttt attttcaaaa tgtggtttta 75660
tctcagttta atgaacacgg catgttttaa tttacacttt catattatat agtaagggcg 75720
tggttacaga tatgttaatt tcctgtgctg cttcacaatg atggaacata atagcaaatg 75780
aaactgttaa tttgcagata cccataggcc tttggtgtct gaatagaaat aaacacacct 75840
acaactgaga gaggaagcat gtgaagcatt ccagtgaaca gaggccattt attcagtcac 75900
agacacagga gaaaaacaac aattaaaaaa aaatctctga tgaaaagttc ataaaaagtt 75960
cactcagttt aagcatatgt cctataacta cttaaaatag agttcttctt aaatatcatt 76020
ctttgctgtt tttagatttc ttctgcctgt atcaaattaa tagaacacag catactttta 76080
atttgctctg gtttcttagt ggggcattta ttaaacacat taaaacaata gtctcagggt 76140
tttactgctg atgttaaagt tctgctttcc tacttaccaa ctgtgtcatc ttaaggcaca 76200
tactttgcct ctctctcaaa tctcccaaat ggagaatgat aagaatacgt acctcaatta 76260
aagaagctat aacaagtaga atgtttggaa aagtgccggg tacaccataa gcccactatg 76320
agtattggat tgtattacct ctgaaagctg cagaatggaa ttctcaaagt tatatgtccc 76380
taaaatcctc ttaagtgaca gaaatggaga aattagcagt ctgtctaaga gagcttttct 76440
agagtctggg catatgtttt taggacaaga cagttcagct tcagcttaaa atgagagagc 76500
acgtctgtgt ccttactcct gggtgccagg tttcttgtcc ccatcttaag acaaataatt 76560
ttggtggaga agaggcagtc tctttgattt cgctctaaaa accttttctg gaggaggtag 76620
acactctcca cccccgtttt gagactcatg cagctgagga tgactggctg agtacaagca 76680
attgttcctt ctaagcagtt tcaattctta taacttgtgg agatattctt aagtccaggg 76740
gattttgtgt atggtggatt tttattacaa agtcctgtac ttcataggaa caaaataatt 76800
caaagtcagg aaccagatca aagccacaac tcagatatgg caccttgaga agttcatttg 76860
tatttcactt gcataaaaac cctcaccact gctatctgat tttcacaaat cattcaacag 76920
ctatccatga agcacccact gtgtgtctgg tctctgtgtc agtccctggc ttcatgtgtc 76980
tttccttctg taccctgact ccccaactca tgaacacatg aagtaaaaaa atgaaaatct 77040
ttttctgacc tctcttcaaa atcacttttt tcaaaacaaa cacctctcac ctgctcatcc 77100
tccagccagt aaatcacagg ggcctagaaa tgtcacttac aaatattttc tgattctgtc 77160
cctcccttca agcttgccaa cattatcaca gtttagggcc tgctcatctt tcccccaatc 77220
tccaattaga tctctccaca atgcaattct gcacattccc tgttacaacc cttcaattat 77280
ttcccagccc atccaaaata aaatctaagc ctcttactaa cacattcagg aactctgtgg 77340
cctacggttt tctacagact aattttccag cagttgactt ccagtgcaag tgaaaaccta 77400
gtgtcatgcc tgcatgatag ataaatttga agctgaagag cccaaatgta tagaccatgc 77460
catgaaaggt ttatagtcat gacacagtgg ccctatagta cagtgcttga agctggctct 77520
ctactgtcag acagaccact tgccagccat gagacctggg gcaaaatgcc ttaattttta 77580
tgtgcctcaa gttctcatgt gagatgagaa taaaaattac ccctatttca taagatttga 77640
taaagtgttt agcataatac ctcataacaa ttgcaattca gtggtggtta ttattataaa 77700
gaaaagatga ttaactttat cttaatgttt aacttgttct gatagttatt gatctatagc 77760
tttgatatgg aggtttgaga atgacctgga aagaattggc cacaatgatt gaagatagtg 77820
atacaagaat aaaagatgac tgcaaaatgt aaacctgcaa taacagaaag aatgaagtca 77880
ctggtctcat gggaactgat atgggagaaa aaaacagatc aaaaggctat tcatgttttg 77940
ggcctctttg tcaaaatgga aatgagaaac tggggaataa aaattaaagc aattctagca 78000
tctggtttta acataattct tatccctaaa aagaatctat aagaaactcc caaaatgaca 78060
ggcagccgtg ggtagcattg catttcaagt aatcttttaa ttgttaaaat ttaagtttcc 78120
aacatgaaca taaaattttc aacctaaaag aaatgagttc caaatctgag acaagtgaaa 78180
aaggataaag cctactaggg ggtaaattcc atctctttag agatctagta cccaatttag 78240
caatgtccaa tcaagccttt aactactaca tttgaacacc tcatcatttc aaaatgttac 78300
ttaatgatgc caattaactg tacaatgtct ctgcatagca catagcccta aaatgatttg 78360
tgcaatgtta ctgtcagtaa aactgaacta cagggaatgc tcatattcta tgtcattata 78420
tacagaaatg caatatcaat aaagtgatat ctgttggtat tagaaaaaag tgaaaatttt 78480
catatctttc tattttcttt tttcctcaat gggatgctct tgttaaagat agctctgcat 78540
agtaaggttt gtataaacat tatttagcta aagttaaaag gggtaacata ctggttctag 78600
cacagatatt aaaacaaatt agtttgtagg tagggcagca atcaattata ttactaacca 78660
tagctttggt ccttttatcc tttcccattt gattttacac agtgggatgt taaaggttga 78720
atgtctttgg tatctataaa cttaattgaa agctgttatt tgtttgttta agtctgttga 78780
tttttataat cataatttta ctcctataga tttcttgtag gagtactata tgaatttatg 78840
ttgcactgaa ttttgttatg ttatacaaat taataggctt ttatttatgg aaagctacta 78900
ttgatctgtc atttcttaaa aaattactaa aaagtgttaa aactttaaat gttggagagt 78960
ttatatttta aaagttacat gctagaaaaa catgatgtct gagtatatta gaagttatag 79020
ataattcatc tgtcaactat aaaactctcc aacactgcct ttctttaatg aataatatga 79080
aatttagcag tgaaaatgtg acaatgtaca atcctaaata aatcaacaaa tttagagatg 79140
tacctctaaa accattgtaa attcaacagt gtaattttcc attggacttt cacttattca 79200
ttcattaaac aaatgtttgt gagtgcctgc aatgtatgag acattgtact gaagctaggc 79260
agtgtgagtt atcatatggg attatccttt aaatacttct gagggcaaaa aaaaaaaaaa 79320
aaagaagaga aaaggtgtga ggaaagataa agggttaatt cattaaaaaa taacacttga 79380
ggactgtttt ctttgcaagg cataaagtta tcaccctttc aaacagtaga tatttcacat 79440
ttaggatgcg agactccagt tccaacaaag ctcattgcac agctgctacc ctgattaaac 79500
tgctacatga actctgagca atgtagcatg gtagccgcat gcttctgctt gcatgatggt 79560
taattccttc cattctcatt agtgattttc tgagctttga aattctgatg gtacctagga 79620
tataaagcat atttatctaa ctgaaaaaca gataattaga tgtaacataa aatatgaatg 79680
gctttgtcac tttattgtag cagagaatga atgtgggata aattaaagct gatgctagaa 79740
catatgccta ttttttagct ggaaaatttc aagatttatg tactttgggc ttgagaaaga 79800
aatggagttt atttttatg cactgacatc tctttttttt tttttttgga agagctctct 79860
taggaatgaa tggtatgtaa atacagtagg aatgtaatta tagattttcc tgacccagtt 79920
cctaaataat agatatcatt tcagaagtgc cccaatacct gaccttttgc tccaagccat 79980
atcaaagcac acatctagtc tacttttcac tctcattcct agccactatg acaatactat 80040
tcagataaaa cttctagtcc tctacttatg tgactcatac caacttgacc ttacgatagt 80100
gactgggggt gcatatctag gttcatgctg tttgtccatt attatggttt tgtgagaaaa 80160
ggcaaaattt ctaggtaaag tgttatgagg acgaataatc caccaggcaa ccaactgacc 80220
ctttcatttg ccatcttgtc acttcaaaca gctctccaga acctgcagcc agcacagacc 80280
aaagtcaggt ttgtctcctc ttctgttgat gaacaaaggt tgattccata tcgtggctat 80340
tgtgaatagt ggcagtaaac atggcagtat tgtatgaaaa tatcacagat agcccttaaa 80400
tatgtgcaac tatgatgatc tatcaaaatt aaaaattaaa atttattttt aaaagttcag 80460
ttagaaagct tgtagttcct ggcaaactac tacctttctc ggcaaaagaa tttgatatct 80520
cttaaatatt ttctgcctaa tgctgataga ttgtatttac atattccatt aatgcaataa 80580
ataaaattac accaaaacat cagcattatt tatttccagg ggcatctctc aaaataaatt 80640
cctccaaaat tcacaaaacc aaaaccaatg tgaaattgta ctcagggatg caaatgtagc 80700
ccagtgaagc atttgcccac ttgtttggta ttattgaagc acaattagaa aaatgtgcaa 80760
tgtatgccca aaaattctat aataagggcc aggcgcggtg gctcacacct gtaatctcag 80820
cattttggga ggccaaggtg ggcaaatcat gaggtcagga gatcgagacc atcctagcta 80880
acaccatgaa acccagtctt tactaaaaat acaaaaaatt ggcccagacg tggtggcggg 80940
atcctgtagt cccagctact cgggaggctg aggcaggaga atggcatgaa cccaggaggc 81000
agagtttgca ctgagcctac tctccagcct gaacgacaga gcgagacccc atctcaaaaa 81060
aaaaaaccat aataagaact ttttaatata ctatattata atgtaaaaag actagatgtc 81120
aaacaaatta ggtgatggga aggaattgag ggagaatttt agactaagca attgagcagc 81180
acctgttttt caccacaaat ctgttacatg tattgctcaa ttgtgctgaa tccatattgg 81240
gtcctggtgg ctatgtaata gtctctttct tggataaatg tttgtcctct cttatggttt 81300
actaatggtg tacagaacag cattgaatag tggttatttc ctatgacttc ctagatatct 81360
ctctcataat cctgaatgtt ttaaagatca ttcttagata gagtacagct agacacgaac 81420
catagtggaa atcaggtaga caaaatttaa aaggagtctt aattgaaggt cattttattg 81480
tcctcagtat taatcttact taaaacaaac ctgtcactga gcagaactca aaacaccaga 81540

-continued gcccttttgcc aaatgtgatt ttttacaaca ggagcgctgg cagttgagag gagtattctg 81600
tcacacttga gagaattcga gtccctgaag atttatatga atgcttagct attatcgaac 81660
catctcttca cagatgactt agtaaatgtc tgcctttgca tcagataatg gcttacaagt 81720
taatctcctc ttgctccctg ttacacacat atacaccttc ttcctaaaca gctcataagg 81780
tgaaagaaag actcagattt ctgactatgt aattgataat atcacacgga ctgcctgctc 81840
atcatctgct agtcacattg gcagagttga cagttttgga gacactgaag acagtgcata 81900
tattaggaaa taagcagttt cctgatataa attttcttgt agtttataaa ttacatagca 81960
tttattattc cctcatattt tataacattt aataatagaa ctgacacata tattcatttt 82020
aaactcaatt gtgtataata actatcatag caacccttca gtgcctaaat atcaaatctt 82080
ccattcctcc catgaacatc ttgaatatat aggtactgtg gttagctcca acaagctttt 82140
ggttagaatt cattgcactg atacatagac attgttttaa aggcaatttc aaatcaaagc 82200
tgtcagctgt gaatcaagca caccttaaaa agtgacacat ttgtcactag attccagcct 82260
ctcaaattac tgacacgcat cctttttatg taaagatgac attgttcttt cctgatatat 82320
tgcattcctc atgaatttct tatagtcata gaatttttat aaaccatttc agaatcgctg 82380
aaataaacat caatattttt aactttttca ttctgtcaaa aatattgtat gcagagatat 82440
tgctgtaagt gtgtatacct gtgcttaaga gactagggct gaagagaagt aatcaaccga 82500
accactggtg taaatgtgcg tcacattttt agtgactaga aattgaaata attccaacaa 82560
atttatgtgc tttgggcttg agaattcaga ctgccttagg ctaagataaa aatcttttcc 82620
tggtactata taccttcttt tattgaatga ctacctggct ctttctatta tatatgcaga 82680
ttttgtacct ctggtcatct ttgtaaatgg tgcctaaaag atatttgaag aataagtgac 82740
cagcaataag aacaaatgtc tatacaaaag caccctttag ttggatgtaa ttcactactt 82800
tgagttgtta ataacctcta aggatgacag tagctattag ttgaataaac cattatgtct 82860
attattagaa cactagatag tttataagtc caaacaatgc ataaaatacc tatctcatgt 82920
taccattgtt taggttacca gataattgtt ctgtccaatt attccactta attttttgct 82980
tgcccattag ctaaatggca agataaaatt tgtcaaacgg gggggaatgt attgaaaatg 83040
ctagacaact acacttaaaa tgaaaacagg ccaggcgcgg tggctcaggc ctgtaatccc 83100
agcactttgg gaggccaagg cgggtggatc acctgaggtc gggagttcaa gaccagcttg 83160
accaacatgg agaaactcca tctctactaa aaatacaaaa ttagccgggc atggtggcac 83220
atacctgtaa tcccaactac tggggaggct gaggcagaag aatcgtttga acccaggagg 83280
cggtggttgc agtgagccga gattgtgcca ctgtattcta gcctaggcaa catgagcgaa 83340
actccatctc aaaaaaaaaa aaaaaaagaa agaaaagaaa acaaatgcat aatttgcaaa 83400
tattattttt atattgtatg ttatctaggg cttctaaatg cattcttctt ataagcctag 83460
gtttgcaata acattcattt agaattgagt aattttaaat ataatatttt ataaaataaa 83520
atataataat ttctcttaat tctttgaaaa tattaaatta aaagggggtt gcaaactctg 83580
cattccacat ttccatccca acatttaatt ttagcaattt tgtagtctgc ctaaaatgca 83640
atccatcatt tactgtttag aaaataggga atgtacacaa aggcctttca gctttccctg 83700
aactccataa aaatcttttt gcttctttac tgcccccctt tgtcaggagt tctgaggaac 83760
tgttttttat cttaagtctc acaaagcatt taggagaata tttaaactta aattctttta 83820
aaacttatgt tcaggacaaa gtaacattgt atgcattggt gtcatatgta tttaaatttt 83880
gaaattttta atactggcaa aatgaggttt caattttaat ataaattatt taacaatctt 83940

-continued

```
aaatcattaa atatattact taatatattt aatatatcta aacagtcaca attttcccat  84000
actaataatc ataaaaaatc ttacccaatg gtcatataga tatacttaat ggagttttgg  84060
gggggtattt ttgtatatta aaaaattcat atatttgcct tacttagaag aactgattaa  84120
atgaaagtat aatattaaca aacatattgt tattttatat ttgcatttgt gataattata  84180
tttgaaacgt tcaagatttt ccaatgaatt tcttttgcat ttgcgtattt gtgccttttt  84240
attataaaaa taggtggctt tttagttcca ctgcataagt ttcaacatag gtctacaaat  84300
agtgcatctt tttgaagtta atcattataa tcacaaattg aagttgcctg agctccaatt  84360
ggagtctaaa tggatgactg aatcttatta ttcgaaaccc actgttgcta cacaatatgg  84420
ccacacaaga gagtacacaa gacccgtctg attcagcctc agtgccataa atattttaat  84480
ggtttcgttg gaatctggaa atggagctca ccacaggaga tgcttcttcc tttgactctc  84540
attattattt cctttacaaa ttaattaata aaaacttaga tgctaaatta gcacttgatg  84600
aaaacttata tagccttgac attttgattc tgtgagtgaa taaaaatact tggagaaata  84660
aaaatcctaa tcatgttcag gaatacccac aaggtaacaa gtacattttt aaactttaaa  84720
aacatttatt attcatgata aaacatgttg tgtgatttaa atataaattt ttattatttg  84780
ctttaactta tttccggatt aaaaagtaaa tgtttaccta gctgttctaa atggtaatcc  84840
tcatgattaa aacagcaatt tgtcatattt cagttacaaa tgatctttta ttattagtta  84900
tagaacataa gtttcttcat tgactgaggc gatgtttcaa gtagataaat ctgttaaaaa  84960
aattgtggtc atattctgtt aaattctcat accaggcaat ttgtttgata ttcaggaaaa  85020
acctagccac tgaccaaaaa ctctacctgc cttctcagtt gtatcctctt ggacttaaag  85080
gggactggga aagttataag atggttcatg atagtccatc aacatcccaa gaacaaaaac  85140
agatgttgta ctgacagcat catatgatca tatgcatgta agagcacatt catattgcca  85200
aatcagttgg aatttttcac ggttgaaagt taaatgaaat gcttagatgt atgagtcatc  85260
ggagttaaag acaattacag ccagatttat ggctgtgcta aaataaagct agttagaaaa  85320
cagaccaaat tccatgacga taccaagtct gactaatgat tcaccttaaa tttcggagca  85380
acatttatcc tcacttgttt gtttatttga caatgtgccc ttatccatta agtaactagg  85440
aggaagggaa aagcactacg tgggtgagtg acaagacact gacactgatt tgtgactttg  85500
gataattcct ggatgctgtt atctgttttg gcatagagat ggatctgtaa ctgctaataa  85560
ttgccgactg tgaccatccc agaggccatt tacttaaccc aggtatttca gacctgacag  85620
cccgaggata aacacgattt ccctccatca ctaacttcat ctgcagggcc taagcctcct  85680
tcacagtctc tccagtgatt tattggcatc tccaagggta tctcacatgt gctgaagaac  85740
aaatctgctc actttcatct gcttggtttt cccttttgaa atctgctgct ttaaaattac  85800
taagggagga atcatgcctg ctgctaccct tgccagtgac cttgcagttt gtgccctgat  85860
tgttccaatt accacaatca aaacagaagc gtttgcagtt actgcagtgc tctctctgtg  85920
gatgtcaggt ctgactcaga gagccaggct ggggaacagc catttccact cttgtacctc  85980
tgcaaaagga cttccatgtt ccgtaaacag actcccacct ctcattttcc ccccaagcaa  86040
agcatcataa attagagagc atgtaacggg aaagaaaatc cattagccat ttgggttcag  86100
tcagacaagc cagctcatgg aaagtttata caggaaggtc acatttcaat tgagatcagg  86160
agggtgaaag ggtccagctg tgtgatgaga gagagaatgt tcgggaatgt ggaacagagg  86220
tatccaaggc agaacaaact cgtatatgaa ggctttaagg gtgtgcaaat ctagcatatt  86280
```

ttatgacata aaagagtcct gattagctag aatatgatga atgtgagaag aggtgaaggc 86340
tggagatagg aaaaattatt ccagatctta taagctatag taagaaattt gcatattata 86400
tatagacttg tgggaagcca ttggattttg taagaaggag attaacatta tcttatttat 86460
gttatttgtg atttataacc ccaaatgtgc cagatacaaa caaaccaaaa ataataataa 86520
taataataag aagaagaaca acaacagcaa tggaactgtg gtgatggttt tggtcacaaa 86580
atgcatatat atctattttt cacaatgcaa aaatatttca ttatttcaaa ttttaacata 86640
aatgtgggta tgcatgagct tacaaatctt gaagtttatt ggggaatatt ggtgagcatg 86700
gtttttattg catggtcaca acttactaat gggaaacatc tgaataccta ttgagttaat 86760
gcatgcacat ttttattttc ctggaatact gagaaaaagg ttgctacata atgtcttgat 86820
agcttctaag tcatggctca aaagtgaatg tggaatctgc taatcggaat ggactcagat 86880
tcagccaagt tctcaaaaac atttgctttc atagatgtct tcaagaaaca aggagtcttg 86940
aatttaaatt gtgaagtgtc tatcttagaa tagagagatt taaaatctga ctgtattttg 87000
tttaaaaaag cctatataac tgtattatat aaaattattt atactacagt taaaaaaaga 87060
atcccatcct atttgtgcct aaataagtgc ctgcttgtag catgaaaact atttgttgag 87120
ggtccttaga tcctcagagc atgctgtgaa agtaggtaca attgttcttt ctatataagc 87180
ctcttaagat aacagataat tgccagaaat acagcacaca gtacaaaatt accttgtttt 87240
acttttgcca caaaaaacaa tttcttttgg ctttgagcaa taaagtccaa tgattttttt 87300
cctttcaaaa tatcttcctc cctctccata agttttatat ttattcacga aggaatattc 87360
caatatcgga tgtttttgtc tgtgtctctt cctggaacaa atgttaatta atctctttgg 87420
gtttgtatgt caagtggagg ggtggggatt ggggacaggt gatagttgtc tagggagtta 87480
acttcatctc tataggagag tggatagacg ctgtatacga aaagctcttg aaaagggaaa 87540
tacagcagcc acttcctcag ggcttccatg gtggtcagac tccttgattg ctttagatta 87600
actctggctt ttgtccttcg gaggccacca gattgggtgg atagacattg tccttgctgt 87660
tcttttgacc tacctacttg tactttaggg gaaaaaaatg cctgtaatag gttaaatgct 87720
ttctcaaaga tcaccaaagt atataacaca tggcaaatag acagagaaat gagacagtat 87780
aatcagtata atttataaaa gtaccttaca gcaggatccc atgggatatg ggtttttttt 87840
aaaaaaaatc tacctaatct tttcattgaa ctcctattca ggattcatta tattgaatat 87900
ggctcagaga cctggaaaat tgtttccacc tttttaattt attcaccatc atttatggaa 87960
gttttcaagg acgtttactt acctacctca gttaacagat tgtactactt gggaagtcta 88020
taaatatgag cttaaagcat tttctgagtt ttaaaataat ttagattgtg tagaatgtta 88080
aaactaaaag aggaaaaaat tattcagttc ctcagttgaa cctagcaatt tatcttttca 88140
cagtgtgctc aagtatagtt tttgaaaagt aaagaagatg gtttttatac aaacataaac 88200
acatttcaaa gattttattc aactaattaa ttagtagtgg agccaataag ctggtaagac 88260
tggtttaaag gaatatctga ggaataaaga tttatagaaa cagtcaaaga aattctaaag 88320
agaattgact aatagatata aatctagtaa atatttgatt aataatagca gtaacctatg 88380
gaattatgtt ttctactgag cataaatgag catgaatctc tttgggtttg tatgtcaagt 88440
ggaagggtgg ggattgggga caagtgatag ttgtcaaggg agttaacttc atctctatag 88500
gagagtggat agatgctgta taagaaaagc tcttgaaaag ggaaataaag cagccactgc 88560
acatctgcac atataacctg tagatctggg ggctctaata aaaaagttaa tggcaatgtc 88620
aaaatctggt gttttatctt agataacttc atagtcattg attgagcccc ttaaaaataa 88680

-continued catttaaagg acatgtagtc attctgtttc tttattgcca agttttcagc aatttttctc 88740
atgagaatga gtgctaagaa acttttggtg gagcgtggtg gctcaagcct gcagtcttgc 88800
actttgggac gccaaggctg gccaattact tgagatcagt agtttgagac caccctggcc 88860
aacatggtga aaccttgtct ctactaaaaa tacaaaaaaa aaaaaaagtg ggatgtggtg 88920
gcatgcgcct gtaatcctgg ctactctgga ggctgaggca cgagagtcac ttgaacccgg 88980
gaggcagagg ttgcagtgag ccgagatcct gccactgcac tccagcctgg gctacagagg 89040
gagactccat ctcaaacaaa caaacaaaca aaaaagaaac ttttaaaata taacaataga 89100
gacattacat aggcccacaa aaccacctcc aaaaaagcat tctatcacct gcaagaaagc 89160
atatatatat atctgctttt gtgtatatat atatatatat atatatctgc ttttgtgtat 89220
atatatatac acacacacac acacatatgt gtgatatcag catgtgtatt tacacatata 89280
ttttgtgcat gtatattttt aactaaaaat gtgctaggag ttagatatga actgattttg 89340
gaggaggtga tatgctgtag agagagagaa tgggagaata gcagtattat aatctctctc 89400
cattgtattc agtttttttc tttgtctgaa tttttaatag aagtcagcca gaagatgtta 89460
gtttctggga aatgtgttga gatttacagt caaatccaga gagaactaga ggcttatgag 89520
taaataagta aaggttatgc agagaaagta ttctttttcc tgtgtaaact tgaatattgg 89580
ccaggcgcgg tggacacctg taatccagca ctttgggagg ccaaggcggg tggatcgact 89640
gaggtcagga gttcatgacc agcctgtcca acatggtgaa acccattctc taccaaaaat 89700
acaaaaatta gtgggtgtgg tggcaggatc ctgtaatccc agctactacg gaggctgagg 89760
caggagaatt gctttaacct aggaggcgga ggttgcagtg agctgagaca gcgccattgc 89820
actatagcta cggcgataag agtgagactt catctaaaaa aaaaaaagaa aagaaaacct 89880
tgaatatttc ttgtacttgt gttcaaatca tacagttatg aaagtttacc cctagctgtt 89940
acacttaaaa tgtacttctg aaatatacag agagatgata cagactatta atgagttcca 90000
ctaaactttt aatggtttag aaaatacaaa tattttctta tttttctgga attccagcca 90060
ttaatgtaaa acattggttt caacataaat aacacactgg catgcacata tgcctaagca 90120
tgggccccca cacatacaga cattctgaaa gaccactttt taaaaatatt cagtaccgta 90180
tattgtgcat tccttcttta tccacatact taagctgctg caagcatccc attgataaca 90240
ccagtaataa aagatgggac catcagtaat gagatttgaa agccccttt gcaagaaagt 90300 aaggactaga aggtggaaat cactctgtct tagagtcata tggattgggg ctttgctaga 90360
agtgtgtgct ctcagggaaa gctgcctttt tattttctcc agagaaaagc ctttttgtca 90420
gtaaaagaag atgtatcatc caatgcatat gtaaaattct aaacagcaga taaaacaaca 90480
ttcactatta atctctgcaa aagaagatat attgaaaaaa tcctcaagtg tccctctttg 90540
ggtttctttg ttatatatta aagcagttat ctttagatgc atgagaatca cctgaagacc 90600
ttatttttaa aattcagatt cctgtcagtt cactcccaaa gattccgatt cagtagttaa 90660
gagacaaagc ctaggaatgt gaatttacaa tcaacacctc aggtgatagc catgcatgtt 90720
cttaatgctc tactactatc tatgcataaa aggaagataa agttttaaaa acttgaaatg 90780
tggtataaca gtttagtatt gaataatata catttttact tattgtaaca aattatgata 90840
tctacttggg gcaacagtat cttttatttt ggatctgaat cctaattttg gctaggtatc 90900
actgagggat tcttagtcta aaacaattaa atggagttag tggtttttt tagtaactct 90960 tgattttctg ttttttcca ttggcatctt acaaaattta ttcattcatt tttccctttt 91020

-continued

```
tcacttggca ttatttgtta gacagtggac aaaagaacta tagaaagtag agaagcatgt  91080
gatgttgtcc tgctcttaga ttctcgcaac tcaggagagg acattcgctt acaccaatca  91140
tctcaaaaca tggcagttta tgctgaactc agtccaatgg gagagcattt gactgagcac  91200
atagggagag aagttagctc tgttgaagga taatcaacga agaattctta ggaaaggtac  91260
agtcattcat tgaatatttg ctcggcactt actaggtgca tatgtgcact aagatctaag  91320
gatgggctga tgaagaaccc aggtcccttt tcttctagtg gacatgcaga ctggcctaaa  91380
aaaaaaaagg taactggaaa atggataagg aaactgagtc actcggttta tttattatca  91440
ctcggtttat ttgcttttgt ttgtattttc attttgacac agcacagtgt catcttaacg  91500
catcctccaa agtgaaggat ggggtggata acactttagt tggcatttct gtagccagga  91560
gccaggatct ttctcccata attgcattaa cctgggaagg caccctctag gtagatttgt  91620
atagcaccct ggttaatcaa ttatcagttt acttcttgtc tcactaagct ttaacacctt  91680
acatttatga agcagtgtaa atataacttt agcatcttga tcacagcaag cacctgattt  91740
gtattttttt attagctcaa gtgaaatcag atcagagaag tacattacag gtcataaaat  91800
atgtgcaaat ttcataatga cctcctttta aaatgtgcaa aaataagatt gttaaggcac  91860
attccagagc cttggggggt gtgtgtgtgt gtgtgtgtgt gtgtgtgtgc gtgtgtgtgt  91920
gtgcttgtct tttgagaata tctgtatatc agaaaatttg gctgagaagc aatcttcttc  91980
ttagtggttc tttttctctt ttgaaaataa agtactaaaa atacttaaag atgcagaaca  92040
gcaacctgtt cccagtgaga ctctcgttta attaatgtgg tgatctatat agagaaaagg  92100
gacaattgca aaagtccctc aataattatc taaccacagt ctttaggtaa ttacagcaga  92160
aagattttca agacacaaaa caccctggaa aatttgacct cttattttga ttcaggcctt  92220
tcatttctta aatattttct ttaatgttga tgtttatgct tgacaaggtc agcctaatgc  92280
cagatgaatc cctggaactc aaaacattgc tgaattcaca gttgaaggat tttaatataa  92340
tataccagct tttaaaaatc ctacagtgag aataacagga ctgaataaaa aaattaagaa  92400
atgctcaggt agaaataaat agagaaattt agaaaaaaaa taaaacgtat tcaaaataag  92460
tattaagcat tggcaaagaa aaaatagtag cagacaatta catgttccat ttgtaaagat  92520
gattattaat tagtggtctt gcaaaacatt ggagaaaatt tgctgaacca tcacattcat  92580
aaatattaaa accacccatt agtgaaaatc tttttactaa acttcacaac tgatagtcaa  92640
ataatgttca gtttttctcc attgcaataa aaaataaagg cttttgcctt cagatcagtc  92700
tctgggcctt attaattcag tcagccagaa gccacatgga aatattttgt tttgttaaaa  92760
gccagcttgc cctcatgatc ttttaaaatc ttttaaaaat cttccatcag ccctctccct  92820
gacttgaatt atggcagtgc tttctaaact ggtaaactca atctccttgg tgtgcctcaa  92880
gatagagtac ataaaccctc cttagaaatt gagctctcaa ttctaaattg cactctccat  92940
gagagcaagc aagaatgctt tgctttgtat taagtggtca caatattaaa tataaccata  93000
gacagcactg tatttttctaa acaccttatt ttcttttaat gactgacata aattagatca  93060
taagtataca aatgcatatc tgttgtattt ttcagcacca tgtgtttttt tttctttttt  93120
ctgagttatt ttcctgcttt cggcagcctt ttctctcagg tgccttgtga tccacagtgg  93180
tgtgtgttca cactaaccaa agcaatagtc ttacctgcca gaaatagctg tgacatttaa  93240
agagaggtcc aggggaaggc acagtgctta acatccaagt ctgaagagct aatagtgaaa  93300
ttggggcatc agctacagag agatttaggg gaagtaacag gcaggttaaa tattttatgg  93360
aaatgatttc tgttctgtat atgattgcaa ttaacacatg tcaatctgtt tcattaattt  93420
```

```
gttaactcat ctattatgct atgccatgaa gaaaataaaa ttggagttct ttattttttt  93480
gagatggagt ctcactctct tgcccaggct ggagtgcagt ggcaggatct cagctcactg  93540
caatctccac cacccaggtt caagcgattc ttctgcctca gccacctgag taactgggac  93600
tacaggtgcg tgcaaccatg cctggctaat ttttgtattt ttagtagaga tggggtttca  93660
ccatgtgggc caggctggtc ccaaactcct gacctcaagt gatccgcctg tcttggcctc  93720
ccaaggtgct gggattacag gcgtgagcca ccgcgccccg ccacaaaact gaagttctaa  93780
gcttcagttt agatgctcac taaatgcttg ttttgcaata cctgactgta actggcagga  93840
atatgttttg aaagtcctca ttttccaggt atgcagatga aatatagggg cattatctac  93900
tatgtcaaat tataatgatt tatcagtggc acatgaaagt cgcctcacat ttcttaatca  93960
gtgatatacc attatgtcat gccacctttt aatgtaatat gtttacatct ttctttagat  94020
gtaagcattc atttagttca tcacggtggc tttcacactt actccaagaa cgctatgagt  94080
tcctttgatg tgctcaagtc tcctgcccca gggagaaagg gagtggtgag caggaatcgc  94140
tttaatctat ttacacagat attttctttt ccatttattt taaaggaatt tttttaact   94200
taatgagtat gcagtgacgg tggtgatgat gatgatacta aggtttaaat gattagatag  94260
tcaaatctgg gctggaattg taatactgtt ttgactttta atcttagaga agctccagtc  94320
tgcttatttt ctgggcataa acacatgaga acaataacac agttctgtta tctgaatgtt  94380
gttatatttt gtttgaaaca ttcagtgact ttcaaatatt gtatttgcct aagaaaattc  94440
aacagagtca gacattctct tccaggttaa atttggtgag tctgctagga aaataaattt  94500
tgtgcactgg tcattctgat ctagtggacg ttctaataaa agcacctttg tgctgcctac  94560
gtcttcactt taaagataag atacctgggt actcgacacc aaattatagt ttgagatctc  94620
aaaaatggga tagggaaacc acagctcaaa aacaaaaata ctagcactgg aaaagataga  94680
actagtgaag atgaatcatt ctctagactt taaattcaga gatatcaaaa ttaagaaaaa  94740
gtaggaggaa taaaaaaaga gggtaagcaa aacaatataa gtttgtatag caagagggta  94800
taaagcaaat acaatatttt tcagaaaaat taaataaaaa tagatttaca taacattgtt  94860
tttaatctca aagatcaaat ttcaattttc atctcatttt aaaacccata tgcacagtct  94920
cctttatata catcagttgg gtgtcaaagt gactttttttc ttgtttccaa atacagttat  94980
ttttaaaatt taattgtatg atttaggaat ttgaaagcaa gccagtttgc acacacatat  95040
gttattatat gtgtgcttta gacttggttt ttagttaatg taacatgaca gggccacctg  95100
agttatttgt ttacaaacta gctggaaagc caccctggag gagaaacctg gcaacaaaat  95160
ggtctgcagc tttgttattg ttatctatag gattggatgc cattattgct gtaaaatagt  95220
tcacaagaac tcagtctatg ggaaagactc aaaaattctt tgcctgttaa agaaaaatca  95280
ggatattgga ctggttagtt taactaaaaa gtgatgatac tcagattctg cttggattca  95340
ctgcttctca gcagttgttt tgtttctttc taattgatat tttatttttc agagaaccca  95400
ttataaaact cttcttcttc ccttaaaatc acaaccacac aacagcaatt aaaacatgct  95460
ttgacgtaag actgatatgg ttttaaaccc agcttgacta tcgaattttt tactttaggc  95520
aaaacacctc tgacatttat gtcttatcgt cagtaaaaag gggtgattaa cagttttaca  95580
agattattca ataaataaat ataaattcct ccttttcctt cctttccttt cttcatcttc  95640
agcatctgca tgccataagc tcattttagt tctctggact catgttaaca tgtcccacct  95700
ttcccaaatt aaacatcatc tctgttattg gctccattct tttcctctca tttgagacaa  95760
```

-continued ttctttatca accaacaccc tctctgctct gtattgtgaa actctgctcc tactacatta 95820
acagtctctt ggtttcttta aaaagaagac aaaacaatta aagaacagaa gcaaaaaatc 95880
tactcaaatc cccaattgtt accctcaaaa ttaattgtcc cacccctagc tttctcattg 95940
cacaactctt tgtcaaaatg ttttctacca tcacagcctt caatgatctt tctggttcct 96000
ttatctcctg aagtctgact tctacctcca tctttttctg gactattcaa cacactttga 96060
gaaaaaacat actttgtta aacaggtatg catccctgaa gcataaaata catagtactg 96120
aaagtgcaca tgtgtggttc ttcccatttt ttttacagca cttgaaactg acaagtagta 96180
gtaccaatta cttagtaaaa gaccttttc atttcatttc tgaaatattg ttattttcct 96240
ttttcatctt ccatctctga ctacacctcc aattttacct ctttgctgcc ttccttccta 96300
agaaagttct tcatgcaatg ccatcttgtt tttcttcact tgcctctttt tctcacttta 96360
attttatgaa ctctgatgac ttacctctgt agtgtaacta ctcaaaatat gtatttctga 96420
agtctcaact ccaatctcat attttcaact tatatttatg gaggcatctc agactcaacc 96480
tacctaaaaa atggcttatc tgccctaaaa tctactttgt tcttttttc tctactgcta 96540 ataattatct tcctagttgg tcaagctcaa aacctaatca tttttactcc ttgtccctgt 96600
gtcagctgtc cacattcaag cagcgtatca tttctgcaca tttttcaagc aagtcagtaa 96660
ctgccttttg tttgggactg tcttttcata tagtgaacag ccttggaaga tagaaatcat 96720
ttctccttct aaaacaaaag gcaggtgtgc ttgcagcctt ggatagaggt agtgcctctt 96780
tctaaagcaa agggacatct ttactggcca ttataaaata tccatgtttc ctgagctctg 96840
cgttcctctt ttctaatgca acccactgag catgtaggtg tcacctgagc ttttctgtgg 96900
gaattgcggc ttgaggaatc agtgcaagaa aatcatgata ctcttgctaa tgctattaat 96960
gtgagtagta aagttaattg tctctgaccc agcactattg tgtctttgcc cagcactcaa 97020
aagactggca ggcttgcaag taggacaaaa tgttagattt ttcacagttc ttctgcttat 97080
aagtacttgt taaaaccaat taaaacacaa cttgtagttt gcacctataa ttttgtagca 97140
tttgcttctt atctatgtca ctaggatgtg cttagtgaca gacccatcta tcatctatta 97200
ctcaagtttt tggctgtatt cctaggcaac agagagaagg ggaacaaaca agaggacctg 97260
tgcacagttt gagaaaggca aaacaccgag cttaattgca gacttgaatg tagctagcaa 97320
acgaagtaag gcaaaaggtt cctttttttt ttttttagat ggagtctcac tctgtcgcca 97380
gtctggagtg cagtggtgct gtctcggctc actgcaacct ccgcctcctg ggttccagcg 97440
attcttctgc ctcagcctcc cgagtagctg ggactacagg catgtgccac catgcccagc 97500
taacttttgt atttttagta gagacggagt ttcaccacgt tggccaggat ggtctcaatc 97560
tcttgacctt gtgatccgcc cattcggcct cccaaagtgc tgagattata ggtgtgagcc 97620
tccgttcccg gccaaaagtt tccatttttt aaatagttgg gtttttagtt tcgattcttt 97680
ccaaaaaaag gttttcttaa aaaaataaaa ttagcaataa gatgaaatat aacaacaata 97740
taatcttatt aagacaatat atgatataca tttatcaaaa tacttatatt ttcaaaagtg 97800
cttaaaataa tctagcacat agtagatgct cagtaaatat ttgatattat gactgtgcat 97860
gggtcattat aggctacttt atgtatatca tttcatttag tacaacatca ctctgaaaaa 97920
tgttttattg ttaccgtttt tcagttgaaa catttacgtt gctcaagatc tcactggtac 97980
catctactat taggtcagtc tgccaccaaa tctcatgctc ttaaatgccc tttttctcct 98040
gagcttccaa caaatagtgt actgtatata attgttgaag ggaggggact gtgagacaaa 98100
atatttagag tgaatgtgta gccacaattt cagttcctca acaaagtgat aaaattagga 98160
atcatcctca atatatattc ttccaacaca cacacacaca tacacacaca cacacacaca 98220
aataccacaa gcccacttga atgcacccca cctacacatt gcaaccatag agacaattgc 98280
agcattaaat acagaatatt ctgtgtgttg tttgtttgtt ctccctttgc tacaaaaatc 98340
agaatttcta ctcaataaac agcaaaggga gatacaaatg aaccaaatta aagaaggaaa 98400
aaatgttgaa aaaattatat acagaactat gtattgattt attgagagtt cagtaatgta 98460
atccagaaat aatggatgcc ttaaaagtaa ttaaaagaat gcaaataaac atttagtgcc 98520
aattaaagaa aaagaaatac aacattagac aaaataaaag atattcattt gatgcaatga 98580
ggaaataatc ttttattcct ctttaaattc tctgtggaat aaggcatggt tataaataaa 98640
taaacatctg ccccatggac ttaatggatc gttatatttt attgcgataa tcataatgaa 98700
attgttggga gggattagta tctctagtgt aatgctaaga aagataaagc ctgtgcccag 98760
gcaaaagctt tcttggttgg tcaaaaggtt tgaagacatt tcaaactatt ctaaaacaaa 98820
caaacaagca aacaaacaaa aaacatacaa tgtctttgcc acatatttag gaaacaaaat 98880
gaacaattta tttctgacaa cctcatagtc tttgttctgt cagaacaata atggaaaggt 98940
ctaaaccaga aaatgctatg cattgaattt ataataaact attttttcct gtaacaaaaa 99000
attgataaac ttgatatttg cagatttaat gattatgtgt ttaaaaaaaa tctggttttt 99060
gcccttgcaa aaaatcatat atatacacat agatatgtat gtgtgtgtgt gcatagtata 99120
tatatatgta tatacatata tatacacaca tttatatata taaacatttc ctttaacctc 99180
ctattttatt ccaataaaaa tattggtatt agagatagtt ctgatatttc atcatgaata 99240
gttaacattg catttggaaa ggattaattt ttttgaaacg taattttacc ttaataagta 99300
gcccagcgta atattttagt aattacacag attttttttt caagacattt gacaactaat 99360
attgcataat agttaagagt gtgggctttg gagccagact tcctatctct gttcattcac 99420
tgataaaatg gagacagtag taacttcctc aaagagttgt tttttaagat caaataatgc 99480
atataaaact cttgaaatgg taccaaatac agagtaagca ccaaataaac attaactgtt 99540
attgttattc catgtccgaa taacacagaa aagtaagaat tttaatattt catttgaatg 99600
accttttaag gatacaccta gcccattatc tttcttgata atcttgtaag atgattcctt 99660
ttttatctcc gatctgttga ggcatggata gaggttttca gagaaaacat tttctaggta 99720
actgaaagaa agtagcaaca acaaactgtg acaaaactta acaatgagag aatttacaag 99780
atagaataat tgcaactcct tttgaaatca accactatgg tcctctggct gggatagcta 99840
agcaaagata ttccagcctg aaggttgaga tctacttgaa gagttttcta tccagattgt 99900
gagggcccct caaacttcac ttagtatctg tttctattag tatggaaact tctggaacct 99960
tgtggtatca cattcacttg actactttat tcctgctcta gctatcttaa agcctttctt 100020
aatcttttat cttttagaga agatacttct aggttttaaa tccaccgatc ttgaagctat 100080
tgccttcact ctctgcttca gagcccatcc ttttgtatat gagtagtttg ttttgcctaa 100140
agtactttct cccagtcaga ttttaagtcc agtttctcat ctgtttttga gagcaaactc 100200
ctgggccttg gctcactaac atcttgacag catatttctt ctttcctatg ggcttttcag 100260
cattccctgg gtttttctaa aatatgaaag cagactcttt atctcttact ttgtcaaagc 100320
ctaccctccc cactgatttc tcacccagtt gctagtttta agacctgcct ctggccgggc 100380
gcagtggctc acgcctgtaa tcccagcact ttgggaggcc aaggtaggtg gatcacgagg 100440
tcaggagatc gagaccatcc tggctaacac agtgaaaccc tgtctctact aaaattacaa 100500

-continued aaaaattagc caggcgtggt ggtgagcgcc tgtagtccca gctactcggg aggctgaagc 100560
aggagaatgg cgtgatcccg tgaggcagag cttgcagtga gctgagatcg cgccactgca 100620
ctccagcctg ggcgacagag cgagactctg tctcaaaaaa aaaaaaaaaa aaaaaaaaaa 100680
aaaaagacct gcctccaaat atcattgtat ttgcaaacat gaaatgactt attgattctg 100740
agctcagcac aagagcaaac ctttctcagc ttgacccatc ttcacatcgt taatgtctta 100800
ttcagtcact acccaagggg ctgaccttca agattctaat ccatgaaagc ttaaaatagt 100860
aaacaaattt gaatatagtt taacatacat aataaatttt atttctagaa gaggaggatc 100920
agcccttaga catgaaaagt aaaaatagtt tattcccaga tttccctttg tgcattagta 100980
tattcaaccg agtctatcca agtaacagga caaaaaaagc tggcagttgt tgctgcgctg 101040
tgaagtctta ttaggtgagt cagctaatta tatggcacta ccataaatac agcaggcact 101100
gccctgcttg ttaggcttgc caaggaaaat aaggatttaa agcagcatac tacctctttg 101160
ctatataatg acattttctt cttaaaaatg attttgcacc aattcctgat ttatccacca 101220
attatttttt aatttatggt tgaatgtatt taaacctgaa ttcagagata aaactagtaa 101280
atagctcccc aaaataaccc caaatatatt taatatatta gctttactct ctcctccact 101340
gccaaacctt taaaaactga aataaattgt ttttatttca tcttttctct ttttctctct 101400
ctctaaggtg attgccaaga ctaaagaaac agctagaagg gcaaaagaca agaaaatcag 101460
taagatagta acagattatc caaagtagag cacggctcag gtgcagtggc tcatgcctgt 101520
aatcccagca ctttcggagg ctgacgcagg aggatcactt gagtccagga gtttgagacc 101580
agcctgggca acataatgaa acttcatctc tataaaaaaa aaaaatttaa atagccgagc 101640
atggtggtgt aagcctatag tcccagctat ttgggaggct gaggctggag gatcacttgg 101700
gcccaggagt tggagactac agtgagctat gattgtatca ctgcattaca gcctgggcaa 101760
tagggcaaga ccctgcctct aaacaaaaga taaacaaagt agagcataaa tggcttctaa 101820
atatatgtta tttatgtgta agactgggtt ctctaaaggt atcatttaat taaaatagat 101880
ttgcattctc aatctgtagg tatggattat gtataatgta tttaagatat gacttacagc 101940
gttcaccaat gtgactattc ccaagtgatc cagatggctg atgacatagt aatttgtaca 102000
tttgctgaga cctgatctga gtaggtatgt aacataactg agggagagca agtccatttg 102060
ccgaaagaaa gcctagcata tgacccagga gccacatctt cactcagcct tgttgctagg 102120
tttggcttag catatataat agcatagcat gtataattta tgacaaaaaa ttatactttg 102180
cactttttaa ttagaacatt caaaatgatc tcaggaagtg gcaccagaga tcatcagtgg 102240
tctactgtac ttcgtgtgta tgtgtctgtg agtatgtatg tgtttgtgtg tgttcccaca 102300
ttctaaggca tgtcttttac aggttagtag aaaatgttga tagaaaatta tagatttcaa 102360
catctaaaac acagtaggtc actacattgt taaaacttgg aattttttat cttgttgtaa 102420
agtcaggcca accaaaccta aaatactgct acattgaaat agtgcaaaat attcaaaata 102480
ctatagttat agatttggta gtaggactgt accagacctg tcactctata caagacttat 102540
gccttgccct ttcacttacc tgttcccttt tacatctatc ttactagatg taatgctata 102600
aattatattt ctaatatatt ataatttatc atgtattata atgtatcaaa tattacaaat 102660
tatgttgcaa ctccccttac ctttcgtctg catattgcct cagaaagaac agatggatcc 102720
aacagacttc aaccacaggc ccttagtgac aaatagctct taatgctggg cttgccactt 102780
tgatgcattt ctaaagttat agaatgttaa atgcaccaag tcctttggtc attttatttc 102840
taccttagat ctaagccata actatacttt cccaaaaatt aaagtttgaa ttttaactta 102900
accatatata attggaaaag gaggttgggt tcgttaagtg taattttatc atgctttatt 102960
atcctttggg cattggatac agcagaacat gccaatttct atggcttctc atgtgacaga 103020
atatacttac taggatgcaa ttaaatactc ctcagagtat gtaaacaata aatgtaatca 103080
ttacattatt tttatattgt tctttcttat gcataatagt aagactgaaa atatagtgtt 103140
atttctgaaa tatgcatatt gttttgcttt tgatgattaa ataacattgt ccaaagtttt 103200 aggtttttttg aaatcttata ttttttaaca aaatatctag cctttccaaa acaagacctc 103260
aataattcgt ttaagaccca gagttgttcc tctccacata gatctcttaa aaaggcagag 103320
gatttatgac ctcaagagaa atcagagtat ccaaagtttg ctttaattca atgttttaaa 103380
aataaaattc cttagatttt atcaaaaatt gagattagtt tgattttgaa tcagatgccc 103440
tttgctcccc accccaaaat ggcattatga gcagactagg aattgataat agaaaattga 103500
acatatgaaa tatatcttta ccttgctttt taacaaggta ttcatgtcta tcgccttcat 103560
ttttaagtgc atcaataaaa tacatggtaa ttctcttagt gaaatatact atctacacta 103620
tgtacacact cccctgtctg aggtagagaa gtagagaata ttcacatttt tgaaacgtct 103680
atgctatttt tatttaaata cgagttctgg gcttgatttc attttggaac acgggtgtgt 103740
gcttaagttg aaccttttttt tcctcttaag tcaaagttct tttttagttt cttcttttat 103800
ctttttggct actatctctc tccttcatcc tcctggtgtg agttgttgag tgaaggtatt 103860
aattccatta tttgaggcta agtgacattg ttcaataatg cagcaaaaca atggttctac 103920
ccaaaatatc ttcaagtgta aaagcagtgg gcaaaagaga aagtgcgctt ctgctgcttt 103980
gaatgtttaa ggctgtgaaa gttgatcaca caaattgggt cattcttgtt atacccaact 104040
aaaacaatca agaagcctgg gaggaaaagc attcaagaaa catcacattg ctccaaaagt 104100
gtaattttct acaagtccgc atgctgaggc tgcctgttgt aacctgggac caatttttc 104160 tgtaactgct gaaaaaactt gctgcagctc taggactaat tttgcccacc actgtcactc 104220
accaattgaa gcttactagc tccccagaac ctttctagtg ccaatgaact ttctcaaaga 104280
gcagcgtgta tcatttctct ttttcagaac acctccaacc tcctctttgt tctttgggta 104340
taccaaagac caaccagcct tgaatttcaa tttttcttcc cacataaaag ttttaattta 104400
gaaatgtatc tctacatttc taactttgac aaagcataga taccagataa ttgatgaaac 104460
cttgctattt taacgatcac catggattac ttcccagtgt cttcagataa ccctcaacat 104520
ttgccaacat ttgatggact tcaaaatgag catatctttt ttaaaaaaaa ttattcacac 104580
tgacagcaag tacattggta tactctatat taaattatac cacagggttt acaaacaatt 104640
ggtgatgtcg ggcagtggtt tccaaggaac atacttaaca agacactcac aaggccctac 104700
aaacctgcat ttttaacaag ggccctagat gattctagaa gagtgtggtt tggaaagcaa 104760
tttttgcctt tattatgtgt cattttaaat atatttaaaa ttaaagttat aagtcataga 104820
attgaataaa gataatttcc ttacagaaag tattactagg tatctaaata caatatggtt 104880
caaaacagga aatttaaaaa gattatgtaa attctgtagt tgtattccta aagacagtag 104940
ctgaaatttt ttcctacttc tccttgtatc acttcccttt tccttcactt tcacttccct 105000
ggaattgtac ttcccaataa gctattagca gtgaaggaag cttcgtctca tgatctgttt 105060
tatagagcac ttcagctggg acgagtacga aatgataatc agttatatca gctattcaac 105120
cctacaggtt tatttaaaaa gaacttgaat aagcttttta gggagaaaga ggtcagtctc 105180
agccatttct gtttcctaat atagctttta agtctttcct tattagcaat gagggtcatt 105240
ccattgtaat tttttgataa ccatttttct ttctgtgtgt caaatgcaga tataagatac 105300
tgaactgagt ctatttcact gttcgtaaaa caatcccatt tgaaaaaaaa aagtctacag 105360
ctattccagg gatagggcct agtagagaga gaataaaagg tattttctta ctatgtctct 105420
atatcctacc ctgtaggttc tcttattaag catacaggca tataccaaaa tccagacgtt 105480
tttctcattt attttattgc cctaacatat tctgggttaa tataatatca taatgaaaat 105540
ttgagaaaaa attgattttt tcaaaagtgt ttaacatttg ttatattggt agtttttttt 105600
cttgtttgtg gtaaaaataa atagaaggtg cacttcacac cttcaagtat gattatattt 105660
tgaaaacaag tcatgaatac tcataaaatg caaattttaa tgttcttttt ttgttacagc 105720
caaactatat taggcacagt tgtaaattgg agttgaaatt taatatttct ttatagataa 105780
caatgttttt agaaataggt ttatgaaaca gtaaatatac aggtataggg ataaaattgt 105840
gtctgatggt catatgaagt gtttgttgtt atattctcct tggaatagct gccaaatatt 105900
ttagtatgct taaaatctac gaatgtgata gagtcaacaa atttagatca catattcaga 105960
aaaacatagt tagagaacta actattgaaa tgagcataca gcagtcttcc tttatctaca 106020
gggatacatt ctgaaacccc cactaggaca cctgaaattg cggatagtag caaaccctac 106080
atatactgtt ttttccaatg cttatgtacc tatgaaaaag tttaatttat aaactaggca 106140
cagtaagaga ttaacaacaa taactaataa caaaagagaa caattataat aatatactgt 106200
aataaaagtt atgtgggtat ggtctcgctt tctctttccc tctctctctg tctctaaata 106260
tcttagtatt ttggggttgc aattggtggt gggcaactga aaccatggaa aacaaaacca 106320
cggataaaag gagactactg tatatacttt ttaaaactga tgaaatatta aactcatgtt 106380
tcttctatat cccacccatt tcccccaccc aaacctagat agatatctta tttgatctgt 106440
aaacatttaa ttaatttgta aaagttaaga actttttgaa gtaaaactgc aatatatcat 106500
cacacctaaa gaaataaaca ataattctta aatatcaagt cagtgttcaa atttccccaa 106560
ctacctcata tgtgttttcc atttgcttat gtagggttcc caatgagaat gaaataaagt 106620
tcttaggttg caattggcta atgctctctc acttctactt taagcggcag gttcccacta 106680
acttcttttt agttgcaatt tacttattga aattagacgt attctttgtc ttgtgtagtt 106740
tctcacagtg caaaatttgc tgattgtagc cactgttgta agcaatgaac atgtttttca 106800
ccaccttata tttgctgtaa gttgtcagtg atagttaaat gttaatcaaa ttcaaattcg 106860
gatcacgtag ggcttttctt tttttgtttt ctttttctat ttatatattt atttatttat 106920
tttgagacgg agtctcactc cgtcaccagg ctggagtgca atggtgtgat ctgggctcac 106980
tgcaatctcc acctcccggg ttcaagtgat tcccctggct cagtctcccg agtagctggg 107040
actataggag aaccaccacg cccggctaac tttttgtatt tttagtagaga tggggtttca 107100
ccatgttggc caggatgcta tagatctcct gacctcaccg atcatgtagg acttcaattg 107160
tcgaacaaac gaacctttaa tagcagttac accattagga tgacctgatc caacatcgag 107220
gtcgtaaacc ctattgtcga tttggactct agaataggat tgtgctgtca tccctagtgt 107280
agcttgttcc cacttgatga agttattgga tcagtgaaca atagcccact taaactagta 107340
cagtcttagt ttaagatggt gatgtgtatg tacttccatc agagggcaca taatacagta 107400
aatcctcact taacttcatc aatagtttct ggaaactgtg acttgaagca aaacaacata 107460
taacaaaacc agttttacca ttggctaatt gatataagca agaattaagt cctatggcaa 107520
atttctggac acaaaaacac catcaaactc ctaaataaag ataaatcact tctgacatta 107580
aacattgaaa ttaatgtgag ctatatatac gtttaagaaa gattaataca aacaagtcaa 107640
ataacttacc taattatttc ggtggaggcc gcaggtggtt ggagcctatc ctggcagctc 107700
agggagcaat atgggaaccc accccggaca ggacgctgtt ccattactgc agggtgctct 107760
tgtacacacc cactcaccca ggctggaacc atgcagacac acacactcac ctaacctaca 107820
catctgtgta catccttcaa agttcagcca aataacatat aaacaaatcc agtaatatcc 107880
atcagtctta gttccgtcat aacaactcct ttttgatcat caaacaacaa acagggtagg 107940
tctgccatat ttacttgtct ggtccatatc aaaattttct aacaaattat attagaaaat 108000
caaatctctg tcagtttcaa aatcatggaa aaaaatttgc cttatttccc ttatacttgg 108060
atatcctaac agtaatctaa atattaatga gaaagttaat gatgtcgttt ccttctccct 108120
gttgtaaaga aggttttgct gtcccgtttg atcactaaga ctaattgaca ctcagaaaaa 108180
gcataggaaa cttctcagca tcacaaaagc tctgtcatct agagaagcta ggacttgagc 108240
tcaagtcctg tgacatggaa ggccttgtgc ctagccatcc tgcagcagag gcgtatctac 108300
caagaagtga aacactacga aaacagtatg tttactccac attttaaagt gaggtagttt 108360
ggggtggttc atattttatt taatttatat attatttgga tttttttag tttataaaaa 108420
gggcattggc aagggcagaa tgatctgtaa gcttctctgc ccacctacca taagcatgat 108480
ctttagtgtg accttttctt actgttagcc attttcttat acttctgcgt ccctgtcagt 108540
cacttccatg tgaagacatg gggaagcttt tttacatcag acatgttgtt gaaaatcagc 108600
cgcgttggct gagggattat ttgatctctt tctccaagtc cctttaggct cacattgcct 108660
ctctgttctt tgaattttca cttaccttta tcttcttata attactttgc tgaaataaat 108720
gcaaagcaac aaaaggtatt tagtgaagaa taccaacaaa gccatgacca tttcaggctg 108780
agttttgtag tattctttgt ctaggaagag atacctagaa aaattttctg accatgtatt 108840
tgattatttt ccttcaatat gtatagtctc agtcttcaaa tttcagaaaa gaatttgttt 108900
cttcattgtc atttaaaatt aatgtgttaa atatgtatgc ttttacatta taagtggtta 108960
taaaagttaa acacttagaa aaaaagtcaa aataacatac atactatcca acaaaataac 109020
tttcatattt tattgtgttt tcttccaaac tttttacctt tgcgtctgaa ttctgtgtag 109080
gttgtatcta taatatagac aacactttat agcctgctaa atattatacc ataaataggt 109140
agttgttaca taattctcag gtaatagtaa tacaggtctt tatcataatc tactgagtag 109200
ttgaatgata atttttttta agacaaggtc tccctctgtc acccaggcta gaatgcagtg 109260
gcatgcacat ggctcactgt agcctctacc tcccaggctc aagtgatcct cctgcctcag 109320
cctcccaagt ggctgggact gtaggcatgt gccaccatgc ccagctattt atttgtattt 109380
ttagtagaga tggggtttca ttgtaacagc ccaggctggt cttgaactcc tggactcaaa 109440
tgatccacct gcctcagcct cccaaagtgc tgaaatcaca ggagtgaacc actgcaccca 109500
gcaataattt tttaactctt cattattcat tgaacattta gttaacaatt ctaaaaattt 109560
tgtttcctgc tgtcattgat cttgtgaaaa atatctttgg actatagctg tggattattt 109620
cctaaatagt aaattacttg agcaaaaagt ttacatactt tgagggttga taacccatgt 109680
tgccgcaatg tttccccgga ggcattgtgg agtttagaat gccagtagta atattaaggt 109740
gtgccatttt caagatccgt ggccaacatc cctatatgta agatttttcc aaaacatggt 109800
tctgattttt aaaagtgaaa aatgctactt catcatgttc tttttgtgct tcttacttta 109860
aatattagaa tgaagaagga gccccacagg aaggaattct ggaagatatg cctgtggatc 109920
ctgacaatga ggcttatgaa atgccttctg aggtaggagt ccaagctgaa tctttctaac 109980

-continued aagacagtac caaaaacctg tcattgtcac atttctcttt cattagtgct tagtgagaat 110040
catttgctct ctacatgctc attacgtgga caacttgcaa gttaagaata gtttttacat 110100
ttttaaaggg tccttaaaaa aaaagaggag gaggaagatg aagaagagga agaaaggatg 110160
taaaagaaat catatgtagt ccacatagct taatatactt actacttgac cctttacagg 110220
aaaagtttac taacccctgc attagagaat atatttttag aaactttaca ttctaaaata 110280
aatttctaaa tggaaagtta gggaaatcaa tggaatgcca aaggaaggtt attatttttt 110340
gccatacatg tccaatggga tgacgcatag taaaataaaa gttacccaca caagttatag 110400
aataaaaaga taaatgcatg atttgcgaca attgatatat tccagtataa tgttttaaac 110460
aacacaatat gattgttaat tttattttga ttgaaaatga aagtatcttt aatagaaaat 110520
gtatcaaaag ggaaattaga aaatactgtt agatgaataa aactggccca agaagaaaca 110580
gtaaatctga atagatttgt aacacagcga atagattaaa ttagtaataa aaaaaaaaac 110640
ctacctgcaa agaaaatccc aggccgagat ggcatcactg gtaaattcta ccaaacattt 110700
aaagaggaat taatactaat tagttaacac caattaatat ctcttacaaa acagaagagg 110760
agacatttcc caactaattt tgtgagacca atattaccct gataatcaaa accaaatgaa 110820
gatatcacaa gaaaagaaac tatataatgg ctccattaaa aattgagttc aagtatgttg 110880
tagtttggtt atgtattatt cctcacggca ttattaaaag gcatgtcgag gatgggcaca 110940
gcagttcaca cctgtaatcc cgcactttgt gagccaaagt ggccaggtta cttgaggcca 111000
ggagttggag accagtctgg ccaacatggt gaaaccccat ctctactaaa aatacaaaaa 111060
ttagccgggc atggtggtac acgcctatgg ttccagctac ttgggaggct gaggcatgag 111120
agtcacttga acccaggagg cagaggttgc agtgagctga gatggcaccc ctgcactcca 111180
atcttggtaa cagagcaaga ctgtctcaca cagacacacg aaaggcatat tgataataat 111240
tcaacttata gaaattgaga ttaaattgtt tgtttgccta ataagaattt ccaatatttt 111300
ggggtctttt atgcaagaca cagtactaaa cacaatggaa aactatagag taattgacat 111360
taccaggaca taaggagttt acagtctggt aggtttgatg aaaaaaaata gaaattcatt 111420
cattcatttc ttcattatga ttcctttaac aaacataatt gattgtcttc gatgtaccag 111480
gcatcacagg agcaaaaata tataagacat actaaaaagt aaaacatttt aaagatctgt 111540
ttcaatcaat caggagaagt tttattgagg aggtaatgtt gatctgggtg ggaaaaggta 111600
agagatatag taggtcaaaa caaacagagg acattctggc acaagggaat atcagaagca 111660
aaggcatgta tgtctgagca tgcaaatgga tatgtctgag aacagtgaat aattatgact 111720
caagcttagg aacaaggaaa atggtgatag attgaatttg cagctatggg tcaaagacaa 111780
gttatagagt attaggataa tcttgtcatt tcagcttgta ttctattcag aaaacaactt 111840
gagttattga agttatgctt atttgtttgt ttttaagcag aatcctgata ttattagagt 111900
tgctctttag gaggaataat ctgatccctt taattaaatc cattaatatt tgtgttgtgg 111960
atgctatcca gatactgtat ggagagcttg aggtttgaaa tacaagtaat aattgaagcc 112020
atagatgaag acgaaatttt caactgggag agtgaaagta gggaaaatgt atcttgcctt 112080
caaacatctt aatttccttc tgagaattag agcatcttag tctggaaaag gctttataga 112140
cagcttgatt ttgttctcac attttacagg tgaagaaact gagaaccaga cagtccaact 112200
tatttgtcct accaaactag gtatatgatc attaaatggt gcatccggat cagaacctag 112260
atattttaac tctgactact actgtaattc acttttatat cagacaagaa agacacaact 112320
attaaaaata agataatatt tgctgcagaa tatttgcaaa aacattgatt gtaaatttta 112380

-continued gtgtaagtgg ggagccattt cctatctcat tggctgtcag tgctgatgcg taattgaaac 112440
ttatactaac agtgtgtgct gtctttttga tttttctaat attaggaagg gtatcaagac 112500
tacgaacctg aagcctaaga aatatctttg ctcccagttt cttgagatct gctgacagat 112560
gttccatcct gtacaagtgc tcagttccaa tgtgcccagt catgacattt ctcaaagttt 112620
ttacagtgta tctcgaagtc ttccatcagc agtgattgaa gtatctgtac ctgcccccac 112680
tcagcatttc ggtgcttccc tttcactgaa gtgaatacat ggtagcaggg tctttgtgtg 112740
ctgtggattt tgtggcttca atctacgatg ttaaaacaaa ttaaaaacac ctaagtgact 112800
accacttatt tctaaatcct cactattttt ttgttgctgt tgttcagaag ttgttagtga 112860
tttgctatca tatattataa gatttttagg tgtcttttaa tgatactgtc taagaataat 112920
gacgtattgt gaaatttgtt aatatatata atacttaaaa atatgtgagc atgaaactat 112980
gcacctataa atactaaata tgaaatttta ccattttgcg atgtgtttta ttcacttgtg 113040
tttgtatata aatggtgaga attaaaataa aacgttatct cattgcaaaa atattttatt 113100
tttatcccat ctcactttaa taataaaaat catgcttata agcaacatga attaagaact 113160
gacacaaagg acaaaaatat aaagttatta atagccattt gaagaaggag gaattttaga 113220
agaggtagag aaaatggaac attaacccta cactcggaat tccctgaagc aacactgcca 113280
gaagtgtgtt ttggtatgca ctggttcctt aagtggctgt gattaattat tgaaagtggg 113340
gtgttgaaga ccccaactac tattgtagag tggtctattt ctcccttcaa tcctgtcaat 113400
gtttgcttta cgtattttgg ggaactgttg tttgatgtgt atgtgtttat aattgttata 113460
catttttaat tgagcctttt attaacatat attgttattt ttgtctcgaa ataatttttt 113520
agttaaaatc tattttgtct gatattggtg tgaatgctgt acctttctga caataaataa 113580
tattcgacca tgaataaaaa aaaaaaaaaa gtgggttccc gggaactaag cagtgtagaa 113640
gatgattttg actacaccct ccttagagag ccataagaca cattagcaca tattagcaca 113700
ttcaaggctc tgagagaatg tggttaactt tgtttaactc agcattcctc actttttttt 113760
tttaatcatc agaaattctc tctctctctc tctcttttc tctcgctctc tttttttttt 113820
tttttttaca ggaaatgcct ttaaacatcg ttggaactac cagagtcacc ttaaaggaga 113880
tcaattctct agactgataa aaatttcatg gcctccttta aatgttgcca aatatatgaa 113940
ttctaggatt tttccttagg aaaggttttt ctctttcagg gaagatctat taactcccca 114000
tgggtgctga aaataaactt gatggtgaaa aactctgtat aaattaattt aaaaattatt 114060
tggtttctct ttttaattat tctggggcat agtcatttct aaaagtcact agtagaaagt 114120
ataatttcaa gacagaatat tctagacatg ctagcagttt atatgtattc atgagtaatg 114180
tgatatatat tgggcgctgg tgaggaagga aggaggaatg agtgactata aggatggtta 114240
ccatagaaac ttcctttttt acctaattga agagagacta ctacagagtg ctaagctgca 114300
tgtgtcatct tacactagag agaaatggta agtttcttgt tttatttaag ttatgtttaa 114360
gcaaggaaag gatttgttat tgaacagtat atttcaggaa ggttagaaag tggcggttag 114420
gatatatttt aaatctacct aaagcagcat attttaaaaa tttaaaagta ttggtattaa 114480
attaagaaat agaggacaga actagactga tagcagtgac ctagaacaat ttgagattag 114540
gaaagttgtg accatgaatt taaggattta tgtggataca aattctcctt taaagtgttt 114600
cttcccttaa tatttatctg acggtaattt ttgagcagtg aattacttta tatatcttaa 114660
tagtttattt gggaccaaac acttaaacaa aaagttcttt aagtcatata agccttttca 114720
ggaagcttgt ctcatattca ctcccgagac attcacctgc caagtggcct gaggatcaat 114780
ccagtcctag gtttattttg cagacttaca ttctcccaag ttattcagcc tcatatgact 114840
ccacggtcgg ctttaccaaa acagttcaga gtgcactttg gcacacaatt gggaacagaa 114900
caatctaatg tgtggtttgg tattccaagt ggggtctttt tcagaatctc tgcactagtg 114960
tgagatgcaa acatgtttcc tcatctttct ggcttatcca g 115001

<210> SEQ ID NO 3
<211> LENGTH: 1096
<212> TYPE: DNA
<213> ORGANISM: Homo sapiens

<400> SEQUENCE: 3
gaattcatta gccatggatg tattcatgaa aggactttca aaggccaagg agggagttgt 60
ggctgctgct gagaaaacca aacagggtgt ggcagaagca gcaggaaaga caaaagaggg 120
tgttctctat gtaggctcca aaaccaagga gggagtggtg catggtgtgg caacagtggc 180
tgagaagacc aaagagcaag tgacaaatgt tggaggagca gtggtgacgg gtgtgacagc 240
agtagcccag aagacagtgg agggagcagg gagcattgca gcagccactg gctttgtcaa 300
aaaggaccag ttgggcaagg aagggtatca agactacgaa cctgaagcct aagaaatatc 360
tttgctccca gtttcttgag atctgctgac agatgttcca tcctgtacaa gtgctcagtt 420
ccaatgtgcc cagtcatgac atttctcaaa gtttttacag tgtatctcga agtcttccat 480
cagcagtgat tgaagtatct gtacctgccc ccactcagca tttcggtgct tccctttcac 540
tgaagtgaat acatggtagc agggtctttg tgtgctgtgg attttgtggc ttcaatctac 600
gatgttaaaa caaattaaaa acacctaagt gactaccact tatttctaaa tcctcactat 660 tttttgttg ctgttgttca gaagttgtta gtgatttgct atcatatatt ataagatttt 720
taggtgtctt ttaatgatac tgtctaagaa taatgacgta ttgtgaaatt tgttaatata 780
tataatactt aaaaatatgt gagcatgaaa ctatgcacct ataaatacta aatatgaaat 840
tttaccattt tgcgatgtgt tttattcact tgtgtttgta tataaatggt gagaattaaa 900
ataaaacgtt atctcattgc aaaaatattt tatttttatc ccatctcact ttaataataa 960
aaatcatgct tataagcaac atgaattaag aactgacaca aaggacaaaa atataaagtt 1020
attaatagcc atttgaagaa ggaggaattt tagaagaggt agagaaaatg gaacattaac 1080
cctacactcg gaattc 1096

<210> SEQ ID NO 4
<211> LENGTH: 411
<212> TYPE: DNA
<213> ORGANISM: Homo sapiens

<400> SEQUENCE: 4
taaaggaatt cattagccat ggatgtattc atgaaaggac tttcaaaggc caaggaggga 60
gttgtggctg ctgctgagaa aaccaaacag ggtgtggcag aagcagcagg aaagacaaaa 120
gagggtgttc tctatgtagt ggctgagaag accaaagagc aagtgacaaa tgttggagga 180
gcagtggtga cgggtgtgac agcagtagcc cagaagacag tggagggagc agggagcatt 240
gcagcagcca ctggctttgt caaaaaggac cagttgggca agaatgaaga aggagcccca 300
caggaaggaa ttctggaaga tatgcctgtg gatcctgaca atgaggctta tgaaatgcct 360
tctgaggaag ggtatcaaga ctacgaacct gaagcctaag aaatatcttt g 411

<210> SEQ ID NO 5
<211> LENGTH: 1208
<212> TYPE: DNA
<213> ORGANISM: Homo sapiens

<400> SEQUENCE: 5
agagaggggg cgagcgaccg agcgccgcga cgcggaagtg aggtgcgtgc gggctgcagc 60
gcagaccccg gcccggcccc tccgagagcg tcctgggcgc tccctcacgc cttgccttca 120
agccttctgc ctttccaccc tcgtgagcgg agaactggga gtggccattc gacgacaggt 180
tagcgggttt gcctcccact cccccagcct cgcgtcgccg gctcacagcg gcctcctctg 240
gggacagtcc cccccgggtg ccgcctccgc ccttcctgtg cgctcctttt ccttcttctt 300
tcctattaaa tattatttgg gaattgttta aatttttttt ttaaaaaaaa gagagaggcg 360
gggaggagtc ggagttgtgg agaagcagag ggactcagtg tggtgtaaag gaattcatta 420
gccatggatg tattcatgaa aggactttca aaggccaagg agggagttgt ggctgctgct 480
gagaaaacca aacagggtgt ggcagaagca gcaggaaaga caaaagaggg tgttctctat 540
gtaggctcca aaaccaagga gggagtggtg catggtgtgg caacagtggc tgagaagacc 600
aaagagcaag tgacaaatgt tggaggagca gtggtgacgg gtgtgacagc agtagcccag 660
aagacagtgg agggagcagg gagcattgca gcagccactg gctttgtcaa aaaggaccag 720
ttgggcaaga atgaagaagg agccccacag gaaggaattc tggaagatat gcctgtggat 780
cctgacaatg aggcttatga aatgccttct gaggaagggt atcaagacta cgaacctgaa 840
gcctaagaaa tatctttgct cccagtttct tgagatctgc tgacagatgt tccatcctgt 900
acaagtgctc agttccaatg tgcccagtca tgacatttct caaagttttt acagtgtatc 960
tcgaagtctt ccatcagcag tgattgaagt atctgtacct gcccccactc agcatttcgg 1020
tgcttccctt tcactgaagt gaatacatgg tagcagggtc tttgtgtgct gtggattttg 1080
tggcttcaat ctacgatgtt aaaacaaatt aaaaacacct aagtgactac cacttatttc 1140
taaatcctca ctattttttg ttgctgttga aaaaaaaaaa aaaaaaaaaa aaaaaaaaaa 1200
aaaaaaaa 1208

<210> SEQ ID NO 6
<211> LENGTH: 708
<212> TYPE: DNA
<213> ORGANISM: Homo sapiens

<400> SEQUENCE: 6
agcgggagaa ggagaaggag gaggactagg aggaggagga cggcgacgac cagaaggggc 60
ccaagagagg gggcgagcga ccgagcgcgc gacgcggaag tgaggtgcgt gcgggctgca 120
gcgcagaccc cggcccggcc cctccgagag cgtcctgggc gctccctcac gccttgcctt 180
caagccttct gcctttccac cctcgtgagc ggagaactgg gagtggccat tcgacgacag 240
tgtggtgtaa aggaattcat tagccatgga tgtattcatg aaaggacttt caaaggccaa 300
ggagggagtt gtggctgctg ctgagaaaac caaacagggt gtggcagaag cagcaggaaa 360
gacaaaagag ggtgttctct atgtaggctc caaaaccaag gagggagtgg tgcatggtgt 420
ggcaacagtg gctgagaaga ccaaagagca agtgacaaat gttggaggag cagtggtgac 480
gggtgtgaca gcagtagccc agaagacagt ggagggagca gggagcattg cagcagccac 540
tggctttgtc aaaaaggacc agttgggcaa gaatgacaga aggagccaca caggaaggac 600
attctggcag atatgcctgt ggatcctgac aatgaggctt atgacatgcc ttctgaggaa 660
gggtatcaag actacgaacc tgaagcctaa gacatatctt tgctccca 708

<210> SEQ ID NO 7
<211> LENGTH: 516
<212> TYPE: DNA
<213> ORGANISM: Homo sapiens

<400> SEQUENCE: 7
ggaggacggc gacgaccaga aggggcccaa gagatggggc gagcgaccga gcgccgcgac 60
gcggaagtga gtgtggtgta aaggaattca ttagccatgg atgtattcat gaaaggactt 120
tcaaaggcca aggagggagt tgtggctgct gctgagaaaa ccaaacaggg tgtggcagaa 180
gcagcaggaa agacattttt tggtgttctc tatgtaggct ccaaaaccaa ggagggagtg 240
gtgcatggtg tggcaacagt ggctgagaag accaaagagc aagtgacaaa tgttggagga 300
gcagtggtga cgggtgtgac agcagtagcc cagaagacag tggagggagc agggagcatt 360
gcagcagcca ctggctttgt caaaaaggac cagttgggca agaatgaaga aggagcccca 420
caggaaggaa ttctggaaga tatgcctgtg gatcctgaca atgaggctta tgaaatgcct 480
tctgaggaag ggtatcaaga ctacgaacct gaagcc 516

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
acgaacctga agcctaagaa atatct 26

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
gagcacttgt acaggatgga acat 24

<210> SEQ ID NO 10
<211> LENGTH: 29
<212> TYPE: DNA
<213> ORGANISM: Artificial Sequence
<220> FEATURE:
<223> OTHER INFORMATION: Probe

<400> SEQUENCE: 10
tgctcccagt ttcttgagat ctgctgaca 29

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
aattccttta caccacactg 20

<210> SEQ ID NO 12
<211> LENGTH: 20

<212> TYPE: DNA
<213> ORGANISM: Artificial Sequence
<220> FEATURE:
<223> OTHER INFORMATION: Synthetic Oligonucleotide

<400> SEQUENCE: 12
atggctaatg aattccttta 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
gaatacatcc atggctaatg 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
gtcctttcat gaatacatcc 20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
tttgaaagtc ctttcatgaa 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tccttggcct ttgaaagtcc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ctcagcagca gccacaactc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
ttggttttct cagcagcagc 20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
atagagaaca ccctcttttg 20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
gttttggagc ctacatagag 20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
tccttggttt tggagcctac 20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
ttgccacacc atgcaccact 20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
ccaacatttg tcacttgctc 20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tgtcacaccc gtcaccactg 20

<210> SEQ ID NO 25
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 25

actggtcctt tttgacaaag                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26

cattcttgcc caactggtcc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27

gtcaggatcc acaggcatat                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28

ttcataagcc tcattgtcag                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29

aaggcatttc ataagcctca                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30

ttcctcagaa ggcatttcat                                               20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31

gatacccttc ctcagaaggc                                               20
```

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
cgtagtcttg atacccttcc 20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
tttcttaggc ttcaggttcg 20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
agatatttct taggcttcag 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ggagcaaaga tatttcttag 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
agcagatctc aagaaactgg 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
actgagcact tgtacaggat 20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ttggaactga gcacttgtac 20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
ggcacattgg aactgagcac 20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
ttgagaaatg tcatgactgg 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
tgtaaaaact ttgagaaatg 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
gaagacttcg agatacactg 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
tcaatcactg ctgatggaag 20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
tacagatact tcaatcactg 20

<210> SEQ ID NO 45

<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
gaccctgcta ccatgtattc 20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
agcacacaaa gaccctgcta 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
atccacagca cacaaagacc 20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
gaagccacaa aatccacagc 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
ggtagtcact taggtgtttt 20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
ataagtggta gtcacttagg 20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
ttagaaataa gtggtagtca 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
aacttctgaa caacagcaac 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
cttataatat atgatagcaa 20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gtatcattaa aagacaccta 20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
gtcattattc ttagacagta 20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
tatttttgca atgagataac 20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
aataaaatat ttttgcaatg 20

<210> SEQ ID NO 58
<211> LENGTH: 20
<212> TYPE: DNA

<213> ORGANISM: Artificial Sequence
<220> FEATURE:
<223> OTHER INFORMATION: Synthetic Oligonucleotide

<400> SEQUENCE: 58
gcttataagc atgattttta 20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
aattcatgtt gcttataagc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
gtgtcagttc ttaattcatg 20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
ggctattaat aactttatat 20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
ttcttcaaat ggctattaat 20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
ttctggcagt gttgcttcag 20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
cagtgcatac caaaacacac 20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
cttaaggaac cagtgcatac 20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
atcacagcca cttaaggaac 20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
tcaataatta atcacagcca 20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
ccactctaca atagtagttg 20

<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
tatcagacaa aatagatttt 20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
ttcacaccaa tatcagacaa 20

<210> SEQ ID NO 71
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 71
attgtcagaa aggtacagca 20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
aatattattt attgtcagaa 20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
catggtcgaa tattatttat 20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
tcgcaaaatg gtaaaatttc 20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 75
gtctgcgctg cagcccgcac 20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
ggaggcaaac ccgctaacct 20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
gtttacctac ctacatagag 20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
gttttggagc ctacaaaaac 20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
ttctcagcca ctggtacaaa 20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
ccattcccaa gagacccaga 20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
agaagaatca attgctttac 20

<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
taatcattta aaccttagta 20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gatacccttc ctaatattag 20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
gatacccttc cttgcccaac 20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
gccactacat agagaacacc 20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
cctttacacc acactgagtc 20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
atatctgcca gaatgtcctt 20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
ttacaccaca ctcacttccg 20

<210> SEQ ID NO 89
<211> LENGTH: 22
<212> TYPE: DNA
<213> ORGANISM: Artificial Sequence
<220> FEATURE:
<223> OTHER INFORMATION: Primer

<400> SEQUENCE: 89
ggtgcttccc tttcactgaa gt 22

<210> SEQ ID NO 90
<211> LENGTH: 24
<212> TYPE: DNA
<213> ORGANISM: Artificial Sequence
<220> FEATURE:
<223> OTHER INFORMATION: Primer

<400> SEQUENCE: 90
acatcgtaga ttgaagccac aaaa 24

<210> SEQ ID NO 91
<211> LENGTH: 32

<212> TYPE: DNA
<213> ORGANISM: Artificial Sequence
<220> FEATURE:
<223> OTHER INFORMATION: Probe

<400> SEQUENCE: 91
aatacatggt agcagggtct ttgtgtgctg tg 32

<210> SEQ ID NO 92
<211> LENGTH: 18
<212> TYPE: DNA
<213> ORGANISM: Artificial Sequence
<220> FEATURE:
<223> OTHER INFORMATION: Primer

<400> SEQUENCE: 92
ggagcaggga gcattgca 18

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
ccttcttcat tcttgcccaa ct 22

<210> SEQ ID NO 94
<211> LENGTH: 17
<212> TYPE: DNA
<213> ORGANISM: Artificial Sequence
<220> FEATURE:
<223> OTHER INFORMATION: Probe

<400> SEQUENCE: 94
cactggcttt gtcaaaa 17

<210> SEQ ID NO 95
<211> LENGTH: 19
<212> TYPE: DNA
<213> ORGANISM: Artificial Sequence
<220> FEATURE:
<223> OTHER INFORMATION: Primer

<400> SEQUENCE: 95
tggcagaagc agcaggaaa 19

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
tccttggttt tggagcctac a 21

<210> SEQ ID NO 97
<211> LENGTH: 17
<212> TYPE: DNA
<213> ORGANISM: Artificial Sequence
<220> FEATURE:
<223> OTHER INFORMATION: Probe

<400> SEQUENCE: 97
caaaagaggg tgttctc 17

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
gttgccacac catgcaccac 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
tgttgccaca ccatgcacca 20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
ctgttgccac accatgcacc 20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 101
actgttgcca caccatgcac 20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
cactgttgcc acaccatgca 20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
ccactgttgc cacaccatgc 20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
gccactgttg ccacaccatg 20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
agccactgtt gccacaccat 20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
cagccactgt tgccacacca 20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
tcagccactg ttgccacacc 20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
ctcagccact gttgccacac 20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
tctcagccac tgttgccaca 20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
ttctcagcca ctgttgccac 20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
cttctcagcc actgttgcca 20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
tcttctcagc cactgttgcc 20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
gtcttctcag ccactgttgc 20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
ggtcttctca gccactgttg 20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
tggtcttctc agccactgtt 20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
ttggtcttct cagccactgt 20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
tttggtcttc tcagccactg 20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
ctttggtctt ctcagccact 20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
tctttggtct tctcagccac 20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
ctctttggtc ttctcagcca 20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
gctctttggt cttctcagcc 20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
tgctctttgg tcttctcagc 20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
ttgctctttg gtcttctcag 20

<210> SEQ ID NO 124

<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
cttgctcttt ggtcttctca 20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
acttgctctt tggtcttctc 20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
cacttgctct ttggtcttct 20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
tcacttgctc tttggtcttc 20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
gtcacttgct ctttggtctt 20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
tgtcacttgc tctttggtct 20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
ttgtcacttg ctctttggtc 20

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
tttgtcactt gctctttggt 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
atttgtcact tgctctttgg 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
catttgtcac ttgctctttg 20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
acatttgtca cttgctcttt 20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
aacatttgtc acttgctctt 20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
caacatttgt cacttgctct 20

<210> SEQ ID NO 137
<211> LENGTH: 1296
<212> TYPE: DNA

<213> ORGANISM: Mus musculus

<400> SEQUENCE: 137

```
acagccctca cgcaccgcac ctccaaccaa cccgtcccct ccctaggaag aggagcgaag     60
gcacgaggca ggcgaggggc ggggagaggc gctgacaaat cagctgcggg ggcgacgtga    120
aggagccagg gagccagagc gcccggcagc aggcagcaga cggcaggaga ccagcaggtg    180
ttccccctgc ccctgcctgc ccttgcctct ttcattgaaa ttagattggg gaaaacagga    240
agaatcggag ttcttcagaa gcctagggag ccgtgtggag caaaaataca tctttagcca    300
tggatgtgtt catgaaagga ctttcaaagg ccaaggaggg agttgtggct gctgctgaga    360
aaaccaagca gggtgtggca gaggcagctg gaaagacaaa agagggagtc ctctatgtag    420
gttccaaaac taaggaagga gtggttcatg gagtgacaac agtggctgag aagaccaaag    480
agcaagtgac aaatgttgga ggagcagtgg tgactggtgt gacagcagtc gctcagaaga    540
cagtggaggg agctgggaat atagctgctg ccactggctt tgtcaagaag gaccagatgg    600
gcaagggtga ggaggggtac ccacaggaag gaatcctgga agacatgcct gtggatcctg    660
gcagtgaggc ttatgaaatg ccttcagagg aaggctacca agactatgag cctgaagcct    720
aagaatgtca ttgcacccaa tctcctaaga tctgccggct gctcttccat ggcgtacaag    780
tgctcagttc caatgtgccc agtcatgacc ttttctcaaa gctgtacagt gtgtttcaaa    840
gtcttccatc agcagtgatc ggcgtcctgt acctgcccct cagcatcccg gtgctcccct    900
ctcactacag tgaaaacctg gtagcagggt cttgtgtgct gtggatattg ttgtggcttc    960
acacttaaat tgttagaaga aacttaaaac acctaagtga ctaccactta tttctaaatc   1020
ttcatcgttt tctttttgtt gctgttctta agaagttgtg atttgctcca agagttttag   1080
gtgtcctgaa tgactctttc tgtctaagaa tgatgtgttg tgaaatttgt taatatatat   1140
tttaaaatta tgtgagcatg agactatgca cctataaata ttaatttatg aattttacag   1200
ttttgtgatg tgttttatta acttgtgttt gtatataaat ggtggaaaat aaaataaaat   1260
attatccatt gcaaaatcaa aaaaaaaaaa aaaaaa                             1296
```

<210> SEQ ID NO 138
<211> LENGTH: 24
<212> TYPE: DNA
<213> ORGANISM: Artificial Sequence
<220> FEATURE:
<223> OTHER INFORMATION: Primer

<400> SEQUENCE: 138

```
agaccaaaga gcaagtgaca aatg                                            24
```

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139

```
cctccactgt cttctgggct act                                             23
```

<210> SEQ ID NO 140
<211> LENGTH: 23
<212> TYPE: DNA
<213> ORGANISM: Artificial Sequence
<220> FEATURE:
<223> OTHER INFORMATION: Probe -continued

<400> SEQUENCE: 140
tggaggagca gtggtgacgg gtg 23

<210> SEQ ID NO 141
<211> LENGTH: 23
<212> TYPE: DNA
<213> ORGANISM: Artificial Sequence
<220> FEATURE:
<223> OTHER INFORMATION: Primer

<400> SEQUENCE: 141
gtcattgcac ccaatctcct aag 23

<210> SEQ ID NO 142
<211> LENGTH: 21
<212> TYPE: DNA
<213> ORGANISM: Artificial Sequence
<220> FEATURE:
<223> OTHER INFORMATION: Primer

<400> SEQUENCE: 142
gactgggcac attggaactg a 21

<210> SEQ ID NO 143
<211> LENGTH: 24
<212> TYPE: DNA
<213> ORGANISM: Artificial Sequence
<220> FEATURE:
<223> OTHER INFORMATION: Probe

<400> SEQUENCE: 143
cggctgctct tccatggcgt acaa 24

MODULATION OF ALPHA SYNUCLEIN EXPRESSION

CROSS REFERENCED TO RELATED APPLICATIONS

This application is a U.S. National Phase filing under 35 U.S.C. §371 claiming priority to International Serial No. PCT/US2011/061245 filed Nov. 17, 2011, which claims priority to U.S. Provisional Application 61/414,848, filed Nov. 17, 2010, each of which is incorporated herein by reference in its entirety.

SEQUENCE LISTING

The present application is being filed along with a Sequence Listing in electronic format. The Sequence Listing is provided as a file entitled BIOL0139USASEQ.txt created May 17, 2013, which is 170 Kb in size. The information in the electronic format of the sequence listing is incorporated herein by reference in its entirety.

FIELD OF THE INVENTION

Embodiments of the present invention provide methods, compounds, and compositions for inhibiting expression of alpha-synuclein mRNA and protein in an animal. Such methods, compounds, and compositions are useful to treat, prevent, or ameliorate neurodegenerative diseases, including, Parkinson's disease, dementia, multiple system atrophy, and Alzheimer's disease.

BACKGROUND OF THE INVENTION

Alpha-synuclein (also known as α-synuclein, SNCA, and a-SYN) is a small, highly charged 140-amino acid residue protein, predominantly expressed in central nervous system (CNS) neurons, where it is localized at presynaptic terminals in close proximity to synaptic vesicles (Iwai, et al., *Neuron.* 1995. 14: 467-475). Alpha-synuclein can associate with lipid membranes by forming amphipathic α-helices, as shown in vitro (Davidson, et al., *J. Biol. Chem.* 1998. 273: 9443-9449). Although the function of alpha-synuclein is still poorly understood, several studies suggest that it is involved in modulating synaptic transmission, the density of synaptic vesicles, and neuronal plasticity (Cabin et al., *J. Neurosci.* 2002. 22: 8797-8807). It has also been suggested that alpha-synuclein may have a chaperone function, as indicated by its effectiveness in preventing aggregation of proteins in in vitro assays (Souza et al., *FEBS Lett.* 2000. 474: 116-119). Moreover, in vivo assays demonstrate that alpha-synuclein chaperone activity is instrumental in promoting the assembly of the SNARE-complex, which is essential for neurotransmitter release in the presynaptic terminals of the brain (Burre et al., *Science.* 329: 1663-1667). Decreased SNARE-complex assembly is associated with neurological impairment, thus, indicating a link between presynaptic alpha-synuclein aggregates and neurodegeneration (Kramer and Schulz-Schaeffer, *J. Neurosci.* 2007. 27: 1405-1410). Knockout mouse models of alpha-synuclein are not lethal, and brain morphology is intact, suggesting that alpha-synuclein is not required for neuronal development and/or that compensatory pathways are present (Abeliovich et al., *Neuron.* 2000. 25: 239-252).

Misfolding, aggregation, and fibrillation of alpha-synuclein are implicated as critical factors in several neurodegenerative diseases, including, Parkinson's disease, Lewy body variant of Alzheimer's disease, diffuse Lewy body disease, dementia with Lewy bodies, and multiple system atrophy (Schulz-Schaeffer *Acta Neuropathol.* 2010. 120: 131-143; Yoshida. *Neuropathology.* 2007. 27: 484-493). In each of these cases, alpha-synuclein protein is misfolded and assembles in aggregates in Lewy bodies and Lewy neurites (Uversky. *J. Neurochem.* 2007. 103: 17-37). Several recent studies have shown that lipidic environments that promote alpha-synuclein folding also accelerate alpha-synuclein aggregation, suggesting that the lipid-associated conformation of alpha-synuclein may be relevant to alpha-synuclein misfolding in neurodegenerative diseases (Conway et al., *Science.* 2001. 294: 6-9; Lee et al., *J. Biol. Chem.* 2002. 277: 671-678). Mutations at position 53, where alanine is changed to threonine, and at position 30, where alanine is changed to proline, have been shown to cause alpha-synuclein to be in a random coil state, so that aggregation is more likely to occur (Clayton and George, *J. Neurosci.* 1999. 58: 120-129).

There is a currently a lack of acceptable options for treating such neurodegenerative disorders. It is therefore an object herein to provide compounds and methods for the treatment of such diseases and disorder.

SUMMARY OF THE INVENTION

Provided herein are methods, compounds, and compositions for modulating expression of alpha-synuclein mRNA and protein. In certain embodiments, alpha-synuclein specific inhibitors modulate expression of alpha-synuclein mRNA and protein. In certain embodiments, alpha-synuclein specific inhibitors are nucleic acids, proteins, antibodies, or small molecules.

In certain embodiments, modulation can occur in a cell or tissue. In certain embodiments, the cell or tissue is in an animal. In certain embodiments, the animal is a human. In certain embodiments, alpha-synuclein mRNA levels are reduced. In certain embodiments, alpha-synuclein protein levels are reduced. In certain embodiments, alpha-synuclein mRNA and protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such diseases, disorders, and conditions are neurodegenerative diseases, disorders, and conditions. In certain embodiments, such neurodegenerative diseases, disorders, and conditions include Parkinson's Disease, dementia, multiple system atrophy (also Shy-Drager syndrome), sporadic and familial Alzheimer's Disease, Lewy body variant of Alzheimer's disease, diffuse Lewy body disease, dementia with Lewy bodies, and pure autonomic failure (also known as Bradbury-Eggleston syndrome). In certain embodiments, such diseases, disorders, and conditions are termed synucleinopathies. In certain embodiments, such synucleinopathies include Parkinson's disease, dementia with Lewy bodies, multiple system atrophy, and pure autonomic failure.

Such diseases, disorders, and conditions can have one or more risk factors, causes, or outcomes in common. Certain risk factors and causes for development of a neurodegenerative disease, and, in particular, a synucleinopathy, include older age, exposure to neurotoxins, genetic predisposition, and trauma.

In certain embodiments, methods of treatment include administering an alpha-synuclein specific inhibitor to an individual in need thereof.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to an alpha-synuclein nucleic acid is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to, administering by a medical professional and self-administering.

"Alpha-synuclein nucleic acid" or "α-synuclein" or "SNCA" or "a-SYN" means any nucleic acid encoding alpha-synuclein. For example, in certain embodiments, an alpha-synuclein nucleic acid includes a DNA sequence encoding alpha-synuclein, an RNA sequence transcribed from DNA encoding alpha-synuclein (including genomic DNA comprising introns and exons), and an mRNA sequence encoding alpha-synuclein. "alpha-synuclein mRNA" means an mRNA encoding an alpha-synuclein protein.

"Alpha-synuclein specific inhibitor" refers to any agent capable of inhibiting the expression of alpha-synuclein mRNA and/or alpha-synuclein protein with few to no off-target effects. Alpha-synuclein specific inhibitors include, but are not limited to, nucleic acids (including antisense compounds), peptides, antibodies, small molecules, and other agents capable of inhibiting the expression of alpha-synuclein mRNA and/or alpha-synuclein protein. In certain embodiments, by specifically modulating alpha-synuclein mRNA expression and/or alpha-synuclein protein expression, alpha-synuclein specific inhibitors affect other downstream proteins and molecules.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid as compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two atoms. A bicyclic sugar is a modified sugar.

"Bicyclic nucleoside" means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in) one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for neurodegenerative disease" means identifying an animal having been diagnosed with a neurodegenerative disease or identifying an animal predisposed to develop a neurodegenerative disease. Such identification may be accomplished by any method including evaluating an individual's medical history and standard clinical tests or assessments.

"Immediately adjacent" means there are no intervening elements between the immediately adjacent elements.

"Inhibiting alpha-synuclein" means reducing expression of alpha-synuclein mRNA and/or protein levels in the presence of an alpha-synuclein specific inhibitor as compared to expression of alpha-synuclein mRNA and/or protein levels in the absence of an alpha-synuclein specific inhibitor.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Neurodegenerative disease" means a disease characterized by progressive loss of structure or function of neurons, including death of neurons.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," "target mRNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods, compounds, and compositions for inhibiting alpha-synuclein mRNA and protein expression.

Embodiments of the present invention provide methods for the treatment, prevention, or amelioration of diseases, disorders, and conditions associated with alpha-synuclein in an individual in need thereof. Also contemplated are methods for the preparation of a medicament for the treatment, prevention, or amelioration of a disease, disorder, or condition associated with alpha-synuclein. Alpha-synuclein associated diseases, disorders, and conditions include neurodegenerative diseases and synucleinopathies, which include Parkinson's Disease, dementia, multiple system atrophy (also Shy-Drager syndrome), sporadic and familial Alzheimer's Disease, Lewy body variant of Alzheimer's disease, diffuse Lewy body disease, and dementia with Lewy bodies.

Embodiments of the present invention provide for the use of an alpha-synuclein specific inhibitor for treating, preventing, or ameliorating an alpha-synuclein associated disease. In certain embodiments, alpha-synuclein specific inhibitors are nucleic acids (including antisense compounds), peptides, antibodies, small molecules, and other agents capable of inhibiting the expression of alpha-synuclein mRNA and/or alpha-synuclein protein.

In certain embodiments of the present invention, alpha-synuclein specific inhibitors are peptides or proteins, such as, but not limited to, synthetic construct alpha-synuclein (68-78), N-methylated at Gly73 as described in *Neurosci. Lett.* 2004. 359: 89-93; N-methylated derivative of SNCA (25-35) as described in *J. Biol. Chem.* 2000. 275: 25109-25112; ASI peptides as described in *FASEB J.* 2004. 18: 1315-1317; RGAVVTGR-amide and RGGAVVTGR-RRRRR-amide as described in *Biochem. Soc. Trans.* 2005. 33: 1106-1110; FK506 as described in *J. Neurosci.* 2010. 30: 2454-2463; tissue transglutaminase as described in *Protein Sci.* 2008. 17: 1395-1402; beta-synuclein as described in *J. Biol. Chem.* 2005. 280: 7562-7569; and peptidyl compounds which are retroenantiomers of the alpha-synuclein sequence as described in US 2009/0286745.

In certain embodiments of the present invention, alpha-synuclein specific inhibitors are antibodies, such as, but not limited to, human single-chain Fv (scFv) antibody, D10, as described in *Mol. Ther.* 2004. 10: 1023-1031; human alpha-SNCA antibodies as described in U.S. Pat. No. 7,727,957; anti-synuclein antibodies as described in U.S. Pat. No. 6,890,535; humanized or chimeric 9E4 antibody as described in USPPN 2010/0278814; humanized version of mouse monoclonal antibody 6H7 as described in USPPN 2010/0031377; and humanized anti-synuclein monoclonal antibody as described in USPPN 2008/0300204.

In certain embodiments of the present invention, alpha-synuclein specific inhibitors are small molecules, such as, but not limited to, curcumin, nicotine, and wine-related polyphenols as described in *Curr. Pharm. Des.* 2008. 14: 3247-3266; 4% $H_2O_2$ as described in *Biochim. Biophys. Acta* 2005. 1703: 157-169; selegiline as described in *J. Mol. Biol.* 2010. Nov. 1 Epub ahead of print; baicalein as described in *J. Neurochem.* 2010. 114: 419-429; cyclic tetrapyrrole phthalocyanine tetrasulfonate as described in *Proc. Natl. Acad. Sci. USA.* 2009. 106: 1057-62; SNX-0723 as described in *J. Pharmacol. Exp. Ther.* 2010. 332: 849-857; N'-benzylidene-benzohydrazide compounds as described in *Biochem. Biophys. Res. Commun.* 2010. 391: 461-466; MG132 and epoxomicin as described in *Neurotox. Res.* 2010. 17:215-227; congo red and Lacmoid as described in *Biochemistry.* 2009. 48: 8322-8334; flavonoid quinine as described in *Biochemistry.* 2009. 48: 8206-8224; valproic acid as described in *Neurotox. Res.* 2010. 17: 130-141; 3,4-dihydroxyphenylacetic acid (DOPAC) as described in *J. Mol. Biol.* 2009. 388: 597-610; PAMAM dendrimers as described in *Macromol. Biosci.* 2009. 9: 230-238; dopamine as described in *PLoS One.* 2008. 3: e3394; melatonin as described in *J. Pineal Res.* 2007. 42: 125-130; rifampicin as described in *Brain Res.* 2007. 1139: 220-225 and *Chem. Biol.* 2004. 11: 1513-1521; ganglioside GM1 as described in *Biochemistry.* 2007. 46: 4868-1877; 4-hydroxy-2-nonenal as described in *J. Biol. Chem.* 2007. 282: 5862-5870; trehalose as described in *J. Biol. Chem.* 2007. 282: 5641-5652; 1,2-dipalmitoyl-sn-glycero-3-phosphate/1,2-dipalmitoyl-sn-glycero-3-phosphocholine and 1,2-dipalmitoyl-sn-glycero-3-phospho-RAC-(1-glycerol)/1,2-dipalmitoyl-sn-glycero-3-phosphocholine as described in *J. Biol. Chem.* 2003. 278: 16873-16877; bis- and tris-dihydroxyaryl compounds and their methylenedioxy analogs as described in USPPN 2010/0179223 and U.S. Pat. No. 7,763,747; 5-(fluoromethyl)piperidine-3,4-diol, 5-(chloromethyl)piperidine-3,4-diol as described in USPPN 2010/0261753; ramelteon as described in USPPN 2010/0056622; cleavage agents as described in USPPN 2010/0036122; *Uncaria tomentosa* extract, gingko biloba, green tea extract, grape seed extract and curcumin as described in USPPN 2009/0123575; catechin or green tea extract as described in USPPN 2008/0306143; farnesyl transferase inhibitor as described in USPPN 2007/0213366.

Embodiments of the present invention provide antisense compounds targeted to an alpha-synuclein nucleic acid. In certain embodiments, the alpha-synuclein nucleic acid is any of the sequences set forth in GENBANK Accession No. NM_000345.3, incorporated herein as SEQ ID NO: 1; the complement of GENBANK Accession No. NT_016354.17 truncated from nucleotides 15140000 to 15255000, incorporated herein as SEQ ID NO: 2; GENBANK Accession No. NM_007308.1, incorporated herein as SEQ ID NO: 3; GENBANK Accession No. L36674.1, incorporated herein as SEQ ID NO: 4; GENBANK Accession No. BC013293.2, incorporated herein as SEQ ID NO: 5; GENBANK Accession No. BG701026.1, incorporated herein as SEQ ID NO: 6; or GENBANK Accession No. BM069769.1, incorporated herein as SEQ ID NO: 7.

In certain embodiments, the invention provides a compound comprising a modified oligonucleotide. In certain embodiments, the compound of the invention comprises a modified oligonucleotide consisting of 12 to 30 linked nucleosides.

In certain embodiments, the compound of the invention may comprise a modified oligonucleotide comprising a nucleobase sequence at least 80%, at least 85%, at least 90%, at least 95%, at least 96%, at least 97%, at least 98%, at least 99% complementary to an equal length portion of SEQ ID NO: 1, 2, 3, 4, 5, 6, or 7. In certain embodiments, the compound of the invention may comprise a modified oligonucleotide comprising a nucleobase sequence 100% complementary to an equal length portion of SEQ ID NO: 1, 2, 3, 4, 5, 6, or 7.

In certain embodiments, the invention provides a compound comprising a modified oligonucleotide comprising a nucleobase sequence complementary to at least a portion of nuncleobases 404 to 463 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 404 to 463 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in SH-SY5Y cells (e.g., as described in Example 6).

In certain embodiments, the invention provides a compound comprising a modified oligonucleotide comprising a nucleobase sequence complementary to at least a portion of nuncleobases 107 to 126 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 107 to 126 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 236 to 301 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 236 to 301 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 304 to 331 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 304 to 331 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 361 to 400 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 361 to 400 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 70% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 404 to 423 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 404 to 423 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 444 to 463 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 444 to 463 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 469 to 488 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 469 to 488 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 90% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 542 to 573 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 542 to 573 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 607 to 721 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 607 to 721 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 734 to 837 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 734 to 837 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 881 to 927 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 881 to 927 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 952 to 983 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 952 to 983 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1001 to 1020 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1001 to 1020 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1030 to 1049 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1030 to 1049 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1055 to 1091 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1055 to 1091 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 80% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1242 to 1261 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1242 to 1261 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1292 to 1333 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1292 to 1333 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1345 to 1374 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1345 to 1374 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 20% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1432 to 1501 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1432 to 1501 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 30% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1522 to 1541 of SEQ ID NO: 1. Said modified oligonucleotide may comprise at least at least 10, at least 12, at least 14, at least 15, at least 16, at least 17, at least 18, at least 19, at least 20 contiguous nucleobases complementary to an equal length portion of nucleobases 1522 to 1541 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 40% inhibition of human mRNA levels as determined using an RT-PCR assay method, optionally in HuVEC cells (e.g., as described in Example 1).

In certain embodiments, the invention provides a compound comprising a modified oligonucleotide comprising a nucleobase sequence complementary to at least a portion of nuncleobases 1703 to 1742 of SEQ ID NO: 1. Said modified oligonucleotide may comprise at least 8, at least 10, at least 12, at least 14, at least 15, at least 16, at least 17, at least 18, at least 19, at least 20 contiguous nucleobases complementary to an equal length portion of nucleobases 1703 to 1742 of SEQ ID NO: 1. Said modified oligonucleotide may comprise a nucleobase sequence at least 80%, at least 85%, at least 90%, at least 91%, at least 92%, at least 93%, at least 94%, at least 95%, at least 96%, at least 97%, at least 98%, or at least 99% complementary to an equal length portion of SEQ ID NO: 1. Said modified oligonucleotide may comprise a nucleobase sequence 100% complementary to an equal length portion of SEQ ID NO: 1. Said modified oligonucleotide may achieve at least 60% inhibition of human mRNA levels as determined using an RT-PCR assay method, optionally in HuVEC cells (e.g., as described in Example 1).

Embodiments of the present invention provide, a modified oligonucleotide consisting of 12 to 30 linked nucleosides having a nucleobase sequence comprising at least 12 contiguous nucleobases of a nucleobase sequence selected from among the nucleobase sequences recited in SEQ ID NOs: 11 to 88 and 98 to 136.

In certain embodiments, the modified oligonucleotide is a single-stranded oligonucleotide.

In certain embodiments, the modified oligonucleotide has a nucleobase sequence that is 100% complementary to a human alpha-synuclein nucleic acid.

In certain embodiments, the modified oligonucleotide comprises at least one modified internucleoside linkage.

In certain embodiments, the at least one modified internucleoside linkage is a phosphorothioate internucleoside linkage.

In certain embodiments, the at least one nucleoside of the modified oligonucleotide comprises a modified sugar.

In certain embodiments, the modified sugar is a bicyclic sugar.

In certain embodiments, the bicyclic sugar comprises a 4'-$CH(CH_3)$—O-2' bridge.

In certain embodiments, the at least one tetrahydropyran modified nucleoside wherein a tetrahydropyran ring replaces the furanose ring.

In certain embodiments, each of the at least one tetrahydropyran modified nucleoside has the structure:

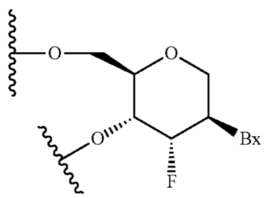

wherein Bx is an optionally protected heterocyclic base moiety.

In certain embodiments, the modified sugar comprises a 2'-O-methoxyethyl group.

In certain embodiments, the at least one nucleoside of the modified oligonucleotide comprises a modified nucleobase.

In certain embodiments, the modified nucleobase is a 5-methylcytosine.

In certain embodiments, the modified oligonucleotide comprises:

(i) a gap segment consisting of linked deoxy nucleosides;
(ii) a 5' wing segment consisting of linked nucleosides;
(iii) a 3' wing segment consisting of linked nucleosides; wherein the gap segment is positioned between the 5' wing segment and the 3' wing segment and wherein each nucleoside of each wing segment comprises a modified sugar.

In certain embodiments, the modified oligonucleotide comprises:

(i) a gap segment consisting of ten linked deoxynucleosides;
(ii) a 5' wing segment consisting of five linked nucleosides;
(iii) a 3' wing segment consisting of five linked nucleosides; wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5-methylcytosine.

Embodiments of the present invention provide methods for identifying an animal having a neurodegenerative disease and administering to said animal a therapeutically effective amount of a composition comprising a modified oligonucleotide consisting of 12 to 30 linked nucleosides having a nucleobase sequence comprising at least 12 contiguous nucleobases of a nucleobase sequence selected from among the nucleobase sequences recited in SEQ ID NOs: SEQ ID NOs: 11 to 88 and 98 to 136.

In certain embodiments, the administration reduces expression of alpha-synuclein.

In certain embodiments, the administration improves motor coordination.

In certain embodiments, the administration improves olfaction.

In certain embodiments, the administration improves spatial memory.

In certain embodiments, the administration reduces aggregation of alpha-synuclein.

Embodiments of the present invention provide, a modified oligonucleotide consisting of 12 to 30 linked nucleosides and having a nucleobase sequence comprising a portion of at least 8, 9, 10, 11, 12, 13, 14, 15, 16, 17, 18, 19, or 20 contiguous nucleobases complementary to an equal length portion of nucleobases 404 to 463 of SEQ ID NO: 1; and wherein the nucleobase sequence of the modified oligonucleotide is at least 90%, 91%, 92%, 93%, 94%, 95%, 96%, 97%, 98%, 99%, or 100% complementary to SEQ ID NO: 1.

Embodiments of the present invention provide, the use of any antisense oligonucleotide described herein for reducing expression of alpha-synuclein in an animal.

Embodiments of the present invention provide, the use of any antisense oligonucleotide described herein for improving motor coordination in an animal.

Embodiments of the present invention provide, the use of any antisense oligonucleotide described herein for reducing aggregation of alpha-synuclein in an animal.

Embodiments of the present invention provide, the use of any antisense oligonucleotide described herein for use in treating an animal having a disease or condition associated with alpha-synuclein by administering to the animal a therapeutically effective amount of the compound so that expression of alpha-synuclein is inhibited.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an alpha-synuclein nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides targeted to an alpha-synuclein nucleic acid may be shortened or truncated. For example, a single subunit may be deleted from the 5' end (5' truncation), or alternatively from the 3' end (3' truncation). A shortened or truncated antisense compound targeted to an alpha-synuclein nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to an alpha-synuclein nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to an alpha-synuclein nucleic acid possess a 5-10-5 gapmer motif.

In certain embodiments, an antisense compound targeted to an alpha-synuclein nucleic acid has a gap-widened motif.

Target Nucleic Acids, Target Regions and Nucleotide Sequences

Nucleotide sequences that encode alpha-synuclein include, without limitation, the following: GENBANK Accession No. NM_000345.3, incorporated herein as SEQ ID NO: 1; the complement of GENBANK Accession No. NT_016354.17 truncated from nucleotides 15140000 to 15255000, incorporated herein as SEQ ID NO: 2; GENBANK Accession No. NM_007308.1, incorporated herein as SEQ ID NO: 3; GENBANK Accession No. L36674.1, incorporated herein as SEQ ID NO: 4; GENBANK Accession No. BC013293.2, incorporated herein as SEQ ID NO: 5; GENBANK Accession No. BG701026.1, incorporated herein as SEQ ID NO: 6; or GENBANK Accession No. BM069769.1, incorporated herein as SEQ ID NO: 7.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for alpha-synuclein can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in alpha-synuclein mRNA levels are indicative of inhibition of alpha-synuclein expression. Reductions in levels of an alpha-synuclein protein are also indicative of inhibition of target mRNA expression. Further, phenotypic changes are indicative of inhibition of alpha-synuclein expression. For example, improved motor coordination, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, recovery from loss in olfaction, and improved autonomic function, such as, decreased orthostatic hypotension.

Hybridization

In some embodiments, hybridization occurs between an antisense compound disclosed herein and an alpha-synuclein nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an alpha-synuclein nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an alpha-synuclein nucleic acid).

Non-complementary nucleobases between an antisense compound and an alpha-synuclein nucleic acid may be tolerated provided that the antisense compound remains able to specifically hybridize to a target nucleic acid. Moreover, an antisense compound may hybridize over one or more segments of an alpha-synuclein nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an alpha-synuclein nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an alpha-synuclein nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an alpha-synuclein nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an alpha-synuclein nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an alpha-synuclein nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substitutent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5', 2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'-O($CH_2$)2O$CH_3$ substituent groups. The substituent at the 2' position can also be selected from allyl, amino, azido, thio, O-allyl, O—$C_1$-$C_{10}$ alkyl, $OCF_3$, O($CH_2$)2S$CH_3$, O($CH_2$)2-O—N(Rm)(Rn), and O—$CH_2$—C(=O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-($CH_2$)—O-2' (LNA); 4'-($CH_2$)—S-2; 4'-$(CH_2)_2$—O-2' (ENA); 4'-CH($CH_3$)—O-2' and 4'-CH($CH_2OCH_3$)—O-2', and analogs thereof (see, U.S. Pat. No. 7,399,845, issued on Jul. 15, 2008); 4'-C($CH_3$)($CH_3$)—O-2', and analogs thereof (see, published PCT International Application WO2009/006478, published Jan. 8, 2009); 4'-$CH_2$—N($OCH_3$)-2', and analogs thereof (see, published PCT International Application WO2008/150729, published Dec. 11, 2008); 4'-$CH_2$—O—N($CH_3$)-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, Chattopadhyaya, et al., *J. Org. Chem.*, 2009, 74, 118-134); and 4'-$CH_2$—C(=$CH_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from $—[C(R_a)(R_b)]_n—$, $—C(R_a)=C(R_b)—$, $—C(R_a)=N—$, $—C(=NR_a)—$, $—C(=O)—$, $—C(=S)—$, $—O—$, $—Si(R_a)_2—$, $—S(=O)_x—$, and $—N(R_a)—$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, $—[C(R_a)(R_b)]_n—$, $—[C(R_a)(R_b)]_n—O—$, $—C(R_aR_b)—N(R)—O—$ or, $—C(R_aR_b)—O—N(R)—$. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2', and 4'-$CH_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA, (G) methylene-thio (4'-$CH_2$—S-2') BNA, (H) methylene-amino (4'-CH2-N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

(A)

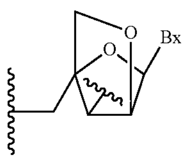

-continued (B)

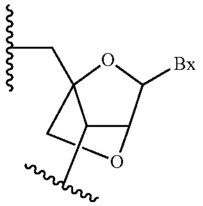

(C)

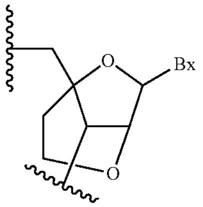

(D)

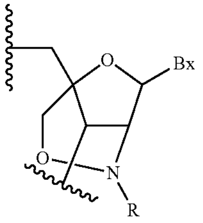

(E)

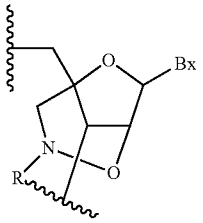

(F)

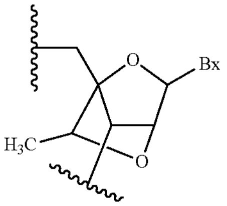

(G)

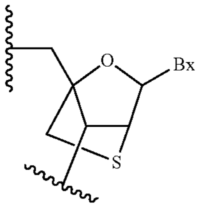

(H)

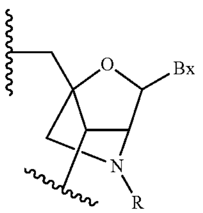

-continued (I)

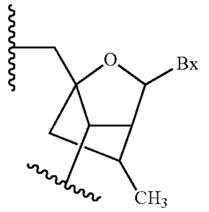

(J)

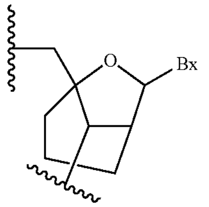

wherein Bx is the base moiety and R is, independently, H, a protecting group or $C_1$-$C_{12}$ alkyl.

In certain embodiments, bicyclic nucleoside having Formula I:

I

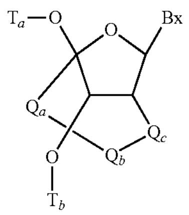

wherein:

Bx is a heterocyclic base moiety;

-$Q_a$-$Q_b$-$Q_c$- is —$CH_2$—N($R_c$)—$CH_2$—, —C(═O)—N($R_c$)—$CH_2$—, —$CH_2$—O—N($R_c$)—, —$CH_2$—N($R_c$)—O—, or —N($R_c$)—O—$CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

II

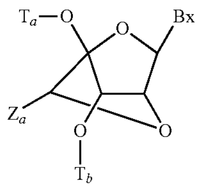

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(═X)$J_c$, and $NJ_e$C(═X)$NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

III

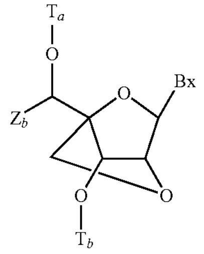

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(═O)—).

In certain embodiments, bicyclic nucleoside having Formula IV:

IV

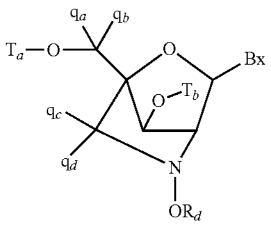

wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

V

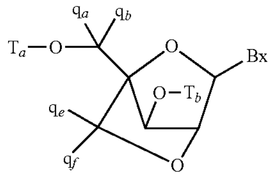

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl, or substituted $C_1$-$C_{12}$ alkyl. The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

VI

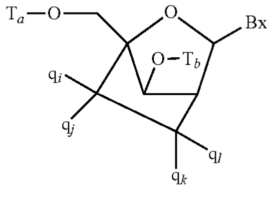

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-$(CH_2)_3$-2' bridge and the alkenyl analog, bridge 4'-CH=CH—$CH_2$-2', have been described (see, e.g., Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C$(=O)N(H)$CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), or those compounds having Formula X:

Formula X:

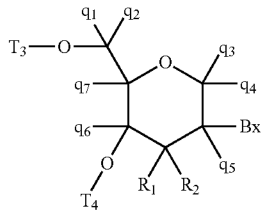

X wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an alpha-synuclein nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an alpha-synuclein nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of alpha-synuclein nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HuVEC cells and SH-SY5Y cells.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of an alpha-synuclein nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an alpha-synuclein nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of alpha-synuclein nucleic acids can be assessed by measuring alpha-synuclein protein levels. Protein levels of alpha-synuclein can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human alpha-synuclein are commercially available.

In Vivo Testing of Antisense Compounds

Antisense compounds, for example, antisense oligonucleotides, are tested in animals to assess their ability to inhibit expression of alpha-synuclein and produce phenotypic changes, such as, improved motor coordination, improved olfaction, improved spatial memory, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, and improved autonomic function, such as, decreased orthostatic hypotension. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, subcutaneous, intramuscular, intraarterial, or intracranial administration, e.g., intrathecal or intracerebroventricular administration. Calculation of antisense oligonucleotide dosage and dosing frequency depends upon many factors such as route of administration and animal body weight. Following a period of treatment with antisense oligonucleotides, RNA is isolated from liver tissue and changes in alpha-synuclein nucleic acid expression are measured. Changes in alpha-synuclein protein levels are also measured.

Certain Indications

In certain embodiments, the invention provides methods, compounds, and compositions of treating an individual comprising administering one or more pharmaceutical compositions of the present invention. In certain embodiments, the individual has a neurodegenerative disease. In certain embodiments, the neurodegenerative disease is Parkinson's Disease, dementia, multiple system atrophy (also Shy-Drager syndrome), sporadic and familial Alzheimer's Disease, Lewy body variant of Alzheimer's disease, diffuse Lewy body disease, or dementia with Lewy bodies. In certain embodiments, the individual has a synucleinopathy. In certain embodiments, the synucleinopathy is Parkinson's Disease, dementia with Lewy bodies, or multiple system atrophy. In certain embodiments, the individual is at risk for developing a neurodegenerative disease and/or a synucleinopathy. This includes individuals having one or more risk factors for developing a neurodegenerative disease and/or synucleinopathy, including, include older age, exposure to neurotoxins, and genetic predisposition. In certain embodiments, the individual has been identified as in need of treatment for a neurodegenerative disease and/or synucleinopathy. In certain embodiments the invention provides methods for prophylactically reducing alpha-synuclein expression in an individual. Certain embodiments include treating an individual in need thereof by administering to an individual a therapeutically effective amount of an antisense compound targeted to an alpha-synuclein nucleic acid.

In certain embodiments, administration of an antisense compound targeted to an alpha-synuclein nucleic acid results in reduction of alpha-synuclein expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to an alpha-synuclein nucleic acid results in improved motor coordination, improved olfaction, improved spatial memory, reduced incidence of resting tremor, reduced incidence of bradykinesia (slow movement), reduced rigidity or inflexibility, improved balance, improved fine motor dexterity, improved gross motor coordination, reduced aggregation of alpha-synuclein, and improved autonomic function, such as, decreased orthostatic hypotension. In certain embodiments, administration of an alpha-synuclein antisense compound improves motor coordination, reduces incidence of resting tremor, reduces incidence of bradykinesia (slow movement), reduces rigidity or inflexibility, improves balance, improves fine motor dexterity, improves gross motor coordination, reduces aggregation of alpha-synuclein, improves autonomic function, and decreases orthostatic hypotension by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to alpha-synuclein are used for the preparation of a medicament for treating a patient suffering or susceptible to a neurodegenerative disease and/or synucleinopathy.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Certain Combination Therapies

In certain embodiments, one or more pharmaceutical compositions of the present invention are co-administered with one or more other pharmaceutical agents. In certain embodiments, one or more pharmaceutical compositions of the present invention are antisense oligonucleotides. In certain embodiments, one or more other pharmaceutical agents are any of peptides, antibodies, or small molecules. In certain embodiments, the peptides, antibodies, or small molecules are any of those described hereinabove (e.g., see Certain Embodiments above).

In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately. In certain embodiments, one or more other pharmaceutical agents include levodopa, dopamine agonists, COMT inhibitors, and antidepressants.

In certain embodiments, one more pharmaceutical compositions of the present invention are administered with physical therapy.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human Alpha-Synuclein (SNCA) in HuVEC Cells

Antisense oligonucleotides targeted to an SNCA nucleic acid were tested for their effects on SNCA mRNA in vitro. Cultured HuVEC cells at a density of 5,000 cells per well were transfected using LipofectAMINE2000® reagent with 10 nM antisense oligonucleotide. After a treatment period of approximately 24 hours, RNA was isolated from the cells and SNCA mRNA levels were measured by quantitative real time PCR using the human primer probe set RTS2621 (forward sequence ACGAACCTGAAGCCTAAGAAATATCT, designated herein as SEQ ID NO: 8; reverse sequence GAGCACTTGTACAGGATGGAACAT, designated herein as SEQ ID NO: 9, probe sequence TGCTCCCAGTTTCTTGAGATCTGCTGACA, designated herein as SEQ ID NO: 10). SNCA mRNA levels were adjusted according to total RNA content, as measured by RIBOGREEN. Results are presented as percent inhibition of SNCA, relative to untreated control cells.

The chimeric antisense oligonucleotides in Tables 1, 2, and 3 were designed as 5-10-5 MOE gapmers. The gapmers are 20 nucleosides in length, wherein the central gap segment is comprised of ten 2'-deoxynucleosides and is flanked on both sides (in the 5' and 3' directions) by wings comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytidine residues throughout each gapmer are 5-methylcytidines. "Start site" indicates the 5'-most nucleoside to which the gapmer is targeted in the human gene sequence. "Stop site" indicates the 3'-most nucleoside to which the gapmer is targeted in the human gene sequence. Each gapmer listed in Table 1 is targeted to SEQ ID NO: 1 (GENBANK Accession No. NM_000345.3). Each gapmer listed in Table 2 is targeted to SEQ ID NO: 2 (the complement of GENBANK Accession No. NT_016354.17 truncated from nucleotides 15140000 to 15255000). Each gapmer listed in Table 3 is targeted to either SEQ ID NO: 3 (GENBANK Accession No. NM_007308.1), SEQ ID NO: 4 (GENBANK Accession No. L36674.1), SEQ ID NO: 5 (GENBANK Accession No. BC013293.2), SEQ ID NO: 6 (GENBANK Accession No. BG701026.1), or SEQ ID NO: 7 (GENBANK Accession No. BM069769.1).

As shown in Tables 1 and 2, several of the gapmers exhibited at least 50% inhibition, as measured by primer probe set RTS2621, including ISIS numbers: 387973, 387974, 387975, 387976, 387977, 387978, 387979, 387980, 387981, 387982, 387983, 387984, 387985, 387986, 387987, 387988, 387989, 387990, 387991, 387994, 387995, 387996, 387997, 387998, 387999, 388000, 388001, 388002, 388004, 388005, 388006, 388007, 388008, 388009, 388010, 388012, 388013, 388014, 388016, 388017, 388021, 388025, 388026, 388027, 388029, 388032, 388033, and 3880309.

Several of the gapmers exhibited at least 60% inhibition, including ISIS numbers: 387973, 387974, 387975, 387976, 387977, 387978, 387979, 387980, 387981, 387982, 387983, 387984, 387985, 387986, 387988, 387989, 387990, 387994, 387995, 387996, 387997, 387998, 387999, 388000, 388001, 388002, 388004, 388005, 388006, 388007, 388008, 388009, 388010, 388014, 388016, 388017, 388026, 388027, 388029, 388032, 388033, and 388039.

Several of the gapmers exhibited at least 70% inhibition, including ISIS numbers: 387973, 387974, 387975, 387976, 387977, 387978, 387979, 387980, 387981, 387982, 387983, 387984, 387985, 387986, 387989, 387994, 387995, 387996, 387997, 387998, 387999, 388000, 388001, 388004, 388006, 388008, 388009, 388010, 388014, 388016, 388017, 388027, 388029, and 388039.

Several of the gapmers exhibited at least 80% inhibition, including ISIS numbers: 387973, 387974, 387975, 387976, 387978, 387979, 387981, 387983, 387984, 387985, 387986, 387994, 387998, 387999, 388000, 388001, 388004, 388006, 388008, 388009, 388010, 388014, 388016, and 388017.

Several of the gapmers exhibited at least 90% inhibition, including ISIS numbers: 387973, 387975, 387983, 387984, 387985, 387986, 387994, 387998, and 388004.

TABLE 1

Inhibition of human SNCA mRNA levels by chimeric antisense oligonucleotides having 5-10-5 MOE wings and deoxy gap targeted to SEQ ID NO: 1

| Start Site | Stop Site | Oligo ID | Sequence | % inhibition | SEQ ID NO |
|---|---|---|---|---|---|
| 236 | 255 | 387973 | AATTCCTTTACACCACACTG | 92 | 11 |
| 246 | 265 | 387974 | ATGGCTAATGAATTCCTTTA | 89 | 12 |
| 256 | 275 | 387975 | GAATACATCCATGGCTAATG | 90 | 13 |
| 266 | 285 | 387976 | GTCCTTTCATGAATACATCC | 89 | 14 |
| 273 | 292 | 387977 | TTTGAAAGTCCTTTCATGAA | 78 | 15 |
| 282 | 301 | 387978 | TCCTTGGCCTTTGAAAGTCC | 88 | 16 |
| 304 | 323 | 387979 | CTCAGCAGCAGCCACAACTC | 80 | 17 |
| 312 | 331 | 387980 | TTGGTTTTCTCAGCAGCAGC | 77 | 18 |
| 361 | 380 | 387981 | ATAGAGAACACCCTCTTTTG | 83 | 19 |
| 375 | 394 | 387982 | GTTTTGGAGCCTACATAGAG | 77 | 20 |
| 381 | 400 | 387983 | TCCTTGGTTTTGGAGCCTAC | 91 | 21 |
| 404 | 423 | 387984 | TTGCCACACCATGCACCACT | 92 | 22 |
| 444 | 463 | 387985 | CCAACATTTGTCACTTGCTC | 95 | 23 |
| 469 | 488 | 387986 | TGTCACACCCGTCACCACTG | 96 | 24 |
| 542 | 561 | 387987 | ACTGGTCCTTTTTGACAAAG | 58 | 25 |
| 554 | 573 | 387988 | CATTCTTGCCCAACTGGTCC | 65 | 26 |
| 607 | 626 | 387989 | GTCAGGATCCACAGGCATAT | 78 | 27 |
| 622 | 641 | 387990 | TTCATAAGCCTCATTGTCAG | 63 | 28 |
| 629 | 648 | 387991 | AAGGCATTTCATAAGCCTCA | 52 | 29 |
| 637 | 656 | 387992 | TTCCTCAGAAGGCATTTCAT | 39 | 30 |
| 644 | 663 | 387993 | GATACCCTTCCTCAGAAGGC | 40 | 31 |
| 653 | 672 | 387994 | CGTAGTCTTGATACCCTTCC | 93 | 32 |
| 671 | 690 | 387995 | TTTCTTAGGCTTCAGGTTCG | 77 | 33 |
| 676 | 695 | 387996 | AGATATTTCTTAGGCTTCAG | 71 | 34 |
| 683 | 702 | 387997 | GGAGCAAAGATATTTCTTAG | 77 | 35 |
| 702 | 721 | 387998 | AGCAGATCTCAAGAAACTGG | 92 | 36 |
| 734 | 753 | 387999 | ACTGAGCACTTGTACAGGAT | 86 | 37 |
| 739 | 758 | 388000 | TTGGAACTGAGCACTTGTAC | 87 | 38 |
| 745 | 764 | 388001 | GGCACATTGGAACTGAGCAC | 87 | 39 |
| 764 | 783 | 388002 | TTGAGAAATGTCATGACTGG | 67 | 40 |
| 774 | 793 | 388003 | TGTAAAAACTTTGAGAAATG | 31 | 41 |
| 792 | 811 | 388004 | GAAGACTTCGAGATACACTG | 94 | 42 |
| 808 | 827 | 388005 | TCAATCACTGCTGATGGAAG | 66 | 43 |
| 818 | 837 | 388006 | TACAGATACTTCAATCACTG | 82 | 44 |
| 881 | 900 | 388007 | GACCCTGCTACCATGTATTC | 68 | 45 |
| 891 | 910 | 388008 | AGCACACAAAGACCCTGCTA | 88 | 46 |
| 897 | 916 | 388009 | ATCCACAGCACACAAAGACC | 80 | 47 |

TABLE 1-continued

Inhibition of human SNCA mRNA levels by chimeric antisense oligonucleotides having 5-10-5 MOE wings and deoxy gap targeted to SEQ ID NO: 1

| Start Site | Stop Site | Oligo ID | Sequence | % inhibition | SEQ ID NO |
|---|---|---|---|---|---|
| 908 | 927 | 388010 | GAAGCCACAAAATCCACAGC | 86 | 48 |
| 952 | 971 | 388011 | GGTAGTCACTTAGGTGTTTT | 49 | 49 |
| 958 | 977 | 388012 | ATAAGTGGTAGTCACTTAGG | 57 | 50 |
| 964 | 983 | 388013 | TTAGAAATAAGTGGTAGTCA | 57 | 51 |
| 1001 | 1020 | 388014 | AACTTCTGAACAACAGCAAC | 82 | 52 |
| 1030 | 1049 | 388015 | CTTATAATATATGATAGCAA | 34 | 53 |
| 1055 | 1074 | 388016 | GTATCATTAAAAGACACCTA | 86 | 54 |
| 1072 | 1091 | 388017 | GTCATTATTCTTAGACAGTA | 82 | 55 |
| 1242 | 1261 | 388018 | TATTTTTGCAATGAGATAAC | 28 | 56 |
| 1249 | 1268 | 388019 | AATAAAATATTTTTGCAATG | 0 | 57 |
| 1292 | 1311 | 388020 | GCTTATAAGCATGATTTTTA | 31 | 58 |
| 1302 | 1321 | 388021 | AATTCATGTTGCTTATAAGC | 51 | 59 |
| 1314 | 1333 | 388022 | GTGTCAGTTCTTAATTCATG | 20 | 60 |
| 1345 | 1364 | 388023 | GGCTATTAATAACTTTATAT | 29 | 61 |
| 1355 | 1374 | 388024 | TTCTTCAAATGGCTATTAAT | 45 | 62 |
| 1432 | 1451 | 388025 | TTCTGGCAGTGTTGCTTCAG | 59 | 63 |
| 1452 | 1471 | 388026 | CAGTGCATACCAAAACACAC | 61 | 64 |
| 1462 | 1481 | 388027 | CTTAAGGAACCAGTGCATAC | 77 | 65 |
| 1472 | 1491 | 388028 | ATCACAGCCACTTAAGGAAC | 31 | 66 |
| 1482 | 1501 | 388029 | TCAATAATTAATCACAGCCA | 70 | 67 |
| 1522 | 1541 | 388030 | CCACTCTACAATAGTAGTTG | 44 | 68 |
| 1693 | 1712 | 388031 | TATCAGACAAAATAGATTTT | 0 | 69 |
| 1703 | 1722 | 388032 | TTCACACCAATATCAGACAA | 67 | 70 |
| 1723 | 1742 | 388033 | ATTGTCAGAAAGGTACAGCA | 64 | 71 |
| 1733 | 1752 | 388034 | AATATTATTTATTGTCAGAA | 0 | 72 |
| 1741 | 1760 | 388035 | CATGGTCGAATATTATTTAT | 5 | 73 |
| 1170 | 1189 | 388037 | TCGCAAAATGGTAAAATTTC | 35 | 74 |
| 107 | 126 | 388039 | GTCTGCGCTGCAGCCCGCAC | 79 | 75 |

TABLE 2

Inhibition of human SNCA mRNA levels by chimeric antisense oligonucleotides having 5-10-5 MOE wings and deoxy gap targeted to SEQ ID NO: 2

| Start Site | Stop Site | Oligo ID | Sequence | % inhibition | SEQ ID NO |
|---|---|---|---|---|---|
| 3451 | 3470 | 387973 | AATTCCTTTACACCACACTG | 92 | 11 |
| 3461 | 3480 | 387974 | ATGGCTAATGAATTCCTTTA | 89 | 12 |
| 3471 | 3490 | 387975 | GAATACATCCATGGCTAATG | 90 | 13 |
| 3481 | 3500 | 387976 | GTCCTTTCATGAATACATCC | 89 | 14 |

TABLE 2-continued

Inhibition of human SNCA mRNA levels by chimeric antisense oligonucleotides having 5-10-5 MOE wings and deoxy gap targeted to SEQ ID NO: 2

| Start Site | Stop Site | Oligo ID | Sequence | % inhibition | SEQ ID NO |
|---|---|---|---|---|---|
| 3488 | 3507 | 387977 | TTTGAAAGTCCTTTCATGAA | 78 | 15 |
| 3497 | 3516 | 387978 | TCCTTGGCCTTTGAAAGTCC | 88 | 16 |
| 3519 | 3538 | 387979 | CTCAGCAGCAGCCACAACTC | 80 | 17 |
| 3527 | 3546 | 387980 | TTGGTTTTCTCAGCAGCAGC | 77 | 18 |
| 3576 | 3595 | 387981 | ATAGAGAACACCCTCTTTTG | 83 | 19 |
| 10958 | 10977 | 387983 | TCCTTGGTTTTGGAGCCTAC | 91 | 21 |
| 10981 | 11000 | 387984 | TTGCCACACCATGCACCACT | 92 | 22 |
| 16775 | 16794 | 387985 | CCAACATTTGTCACTTGCTC | 95 | 23 |
| 16800 | 16819 | 387986 | TGTCACACCCGTCACCACTG | 96 | 24 |
| 16873 | 16892 | 387987 | ACTGGTCCTTTTTGACAAAG | 58 | 25 |
| 109906 | 109925 | 387989 | GTCAGGATCCACAGGCATAT | 78 | 27 |
| 109921 | 109940 | 387990 | TTCATAAGCCTCATTGTCAG | 63 | 28 |
| 109928 | 109947 | 387991 | AAGGCATTTCATAAGCCTCA | 52 | 29 |
| 112485 | 112504 | 387994 | CGTAGTCTTGATACCCTTCC | 93 | 32 |
| 112503 | 112522 | 387995 | TTTCTTAGGCTTCAGGTTCG | 77 | 33 |
| 112508 | 112527 | 387996 | AGATATTTCTTAGGCTTCAG | 71 | 34 |
| 112515 | 112534 | 387997 | GGAGCAAAGATATTTCTTAG | 77 | 35 |
| 112534 | 112553 | 387998 | AGCAGATCTCAAGAAACTGG | 92 | 36 |
| 112566 | 112585 | 387999 | ACTGAGCACTTGTACAGGAT | 86 | 37 |
| 112571 | 112590 | 388000 | TTGGAACTGAGCACTTGTAC | 87 | 38 |
| 112577 | 112596 | 388001 | GGCACATTGGAACTGAGCAC | 87 | 39 |
| 112596 | 112615 | 388002 | TTGAGAAATGTCATGACTGG | 67 | 40 |
| 112606 | 112625 | 388003 | TGTAAAAACTTTGAGAAATG | 31 | 41 |
| 112624 | 112643 | 388004 | GAAGACTTCGAGATACACTG | 94 | 42 |
| 112640 | 112659 | 388005 | TCAATCACTGCTGATGGAAG | 66 | 43 |
| 112650 | 112669 | 388006 | TACAGATACTTCAATCACTG | 82 | 44 |
| 112713 | 112732 | 388007 | GACCCTGCTACCATGTATTC | 68 | 45 |
| 112723 | 112742 | 388008 | AGCACACAAAGACCCTGCTA | 88 | 46 |
| 112729 | 112748 | 388009 | ATCCACAGCACACAAAGACC | 80 | 47 |
| 112740 | 112759 | 388010 | GAAGCCACAAAATCCACAGC | 86 | 48 |
| 112784 | 112803 | 388011 | GGTAGTCACTTAGGTGTTTT | 49 | 49 |
| 112790 | 112809 | 388012 | ATAAGTGGTAGTCACTTAGG | 57 | 50 |
| 112796 | 112815 | 388013 | TTAGAAATAAGTGGTAGTCA | 57 | 51 |
| 112833 | 112852 | 388014 | AACTTCTGAACAACAGCAAC | 82 | 52 |
| 112862 | 112881 | 388015 | CTTATAATATATGATAGCAA | 34 | 53 |
| 112887 | 112906 | 388016 | GTATCATTAAAAGACACCTA | 86 | 54 |
| 112904 | 112923 | 388017 | GTCATTATTCTTAGACAGTA | 82 | 55 |

TABLE 2-continued

Inhibition of human SNCA mRNA levels by chimeric antisense oligonucleotides having 5-10-5 MOE wings and deoxy gap targeted to SEQ ID NO: 2

| Start Site | Stop Site | Oligo ID | Sequence | % inhibition | SEQ ID NO |
|---|---|---|---|---|---|
| 113074 | 113093 | 388018 | TATTTTTGCAATGAGATAAC | 28 | 56 |
| 113081 | 113100 | 388019 | AATAAAATATTTTTGCAATG | 0 | 57 |
| 113124 | 113143 | 388020 | GCTTATAAGCATGATTTTTA | 31 | 58 |
| 113134 | 113153 | 388021 | AATTCATGTTGCTTATAAGC | 51 | 59 |
| 113146 | 113165 | 388022 | GTGTCAGTTCTTAATTCATG | 20 | 60 |
| 113177 | 113196 | 388023 | GGCTATTAATAACTTTATAT | 29 | 61 |
| 113187 | 113206 | 388024 | TTCTTCAAATGGCTATTAAT | 45 | 62 |
| 113264 | 113283 | 388025 | TTCTGGCAGTGTTGCTTCAG | 59 | 63 |
| 113284 | 113303 | 388026 | CAGTGCATACCAAAACACAC | 61 | 64 |
| 113294 | 113313 | 388027 | CTTAAGGAACCAGTGCATAC | 77 | 65 |
| 113304 | 113323 | 388028 | ATCACAGCCACTTAAGGAAC | 31 | 66 |
| 113314 | 113333 | 388029 | TCAATAATTAATCACAGCCA | 70 | 67 |
| 113354 | 113373 | 388030 | CCACTCTACAATAGTAGTTG | 44 | 68 |
| 113525 | 113544 | 388031 | TATCAGACAAAATAGATTTT | 0 | 69 |
| 113535 | 113554 | 388032 | TTCACACCAATATCAGACAA | 67 | 70 |
| 113555 | 113574 | 388033 | ATTGTCAGAAAGGTACAGCA | 64 | 71 |
| 113565 | 113584 | 388034 | AATATTATTTATTGTCAGAA | 0 | 72 |
| 113573 | 113592 | 388035 | CATGGTCGAATATTATTTAT | 5 | 73 |
| 113002 | 113021 | 388037 | TCGCAAAATGGTAAAATTTC | 35 | 74 |
| 2053 | 2072 | 388039 | GTCTGCGCTGCAGCCCGCAC | 79 | 75 |
| 2183 | 2202 | 388040 | GGAGGCAAACCCGCTAACCT | 63 | 76 |
| 3590 | 3609 | 388042 | GTTTACCTACCTACATAGAG | 8 | 77 |
| 10952 | 10971 | 388043 | GTTTTGGAGCCTACAAAAAC | 56 | 78 |
| 16748 | 16767 | 388044 | TTCTCAGCCACTGGTACAAA | 40 | 79 |
| 49342 | 49361 | 388045 | CCATTCCCAAGAGACCCAGA | 92 | 80 |
| 73617 | 73636 | 388046 | AGAAGAATCAATTGCTTTAC | 85 | 81 |
| 94236 | 94255 | 388047 | TAATCATTTAAACCTTAGTA | 32 | 82 |
| 112476 | 112495 | 388048 | GATACCCTTCCTAATATTAG | 46 | 83 |

TABLE 3

Inhibition of human SNCA mRNA levels by chimeric antisense oligonucleotides having 5-10-5 MOE wings and deoxy gap targeted to SEQ ID NOs: 3-7

| Target SEQ ID NO | Start Site | Stop Site | Oligo ID | Sequence | % inhibition | SEQ ID NO |
|---|---|---|---|---|---|---|
| 3 | 310 | 329 | 388036 | GATACCCTTCCTTGCCCAAC | 12 | 84 |
| 4 | 124 | 143 | 388038 | GCCACTACATAGAGAACACC | 78 | 85 |
| 5 | 392 | 411 | 388041 | CCTTTACACCACACTGAGTC | 91 | 86 |

TABLE 3-continued

| Inhibition of human SNCA mRNA levels by chimeric antisense oligonucleotides having 5-10-5 MOE wings and deoxy gap targeted to SEQ ID NOs: 3-7 | | | | | | |
|---|---|---|---|---|---|---|
| Target SEQ ID NO | Start Site | Stop Site | Oligo ID | Sequence | % inhibition | SEQ ID NO |
| 6 | 595 | 614 | 388049 | ATATCTGCCAGAATGTCCTT | 86 | 87 |
| 7 | 62 | 81 | 388050 | TTACACCACACTCACTTCCG | 55 | 88 |

Example 2

Dose-Dependent Antisense Inhibition of Human SNCA in HuVEC Cells

Eleven gapmers, exhibiting over 84 percent or greater in vitro inhibition of human SNCA in the study described in Example 1, were tested at various doses in HuVEC cells. Cells were plated at a density of 6,000 cells per well and transfected using LipofectAMINE2000® reagent with 0.08 nM, 0.25 nM, 0.74 nM, 2.22 nM, 6.67 nM, and 20.00 nM concentrations of antisense oligonucleotide, as specified in Table 4. After a treatment period of approximately 16 hours, RNA was isolated from the cells and SNCA mRNA levels were measured by quantitative real-time PCR. Human SNCA primer probe set RTS2621 (described herein above in Example 1) was used to measure mRNA levels. SNCA mRNA levels were adjusted according to total RNA content, as measured by RIBOGREEN. Results are presented as percent inhibition of SNCA, relative to untreated control cells. As illustrated in Table 4, SNCA mRNA levels were reduced in a dose-dependent manner in antisense oligonucleotide treated cells.

TABLE 4

| Dose-dependent antisense inhibition of human SNCA in HuVEC cells | | | | | | | |
|---|---|---|---|---|---|---|---|
| Oligo ID | 0.08 nM | 0.25 nM | 0.74 nM | 2.22 nM | 6.67 nM | 20.00 nM | $IC_{50}$ (nM) |
| 387973 | 0 | 11 | 23 | 46 | 72 | 81 | 2.6 |
| 387975 | 9 | 8 | 25 | 57 | 72 | 83 | 2.1 |
| 387978 | 13 | 28 | 39 | 68 | 81 | 89 | 1.1 |
| 387983 | 0 | 8 | 17 | 49 | 75 | 85 | 2.6 |
| 387984 | 3 | 15 | 30 | 66 | 82 | 86 | 1.5 |
| 387985 | 0 | 6 | 24 | 66 | 77 | 89 | 1.8 |
| 387986 | 0 | 17 | 33 | 67 | 77 | 84 | 1.7 |
| 388004 | 0 | 11 | 30 | 65 | 78 | 86 | 1.8 |
| 388008 | 2 | 0 | 26 | 59 | 77 | 88 | 2.1 |
| 388010 | 0 | 8 | 24 | 54 | 71 | 87 | 2.3 |
| 388041 | 0 | 10 | 27 | 55 | 77 | 86 | 2.2 |

Example 3

Dose-Dependent Antisense Inhibition of Human SNCA in SH-SY5Y Cells

Gapmers were selected from the study described in Example 2 and tested at various doses in SH-SY5Y cells. Cells were plated at a density of 20,000 cells per well and transfected using electroporation with 5 μM, 10 μM, and 20 μM concentrations of antisense oligonucleotide, as specified in Table 5. After a treatment period of approximately 16 hours, RNA was isolated from the cells and SNCA mRNA levels were measured by quantitative real-time PCR. Human SNCA primer probe set RTS2620 (forward sequence GGTGCTTCCCTTTCACTGAAGT, designated herein as SEQ ID NO: 89; reverse sequence ACATCGTAGATTGAAGCCACAAAA, designated herein as SEQ ID NO: 90, probe sequence AATACATGGTAGCAGGGTCTTTGTGTGCTGTG, designated herein as SEQ ID NO: 91) was used to measure mRNA levels. SNCA mRNA levels were adjusted according to total RNA content, as measured by RIBOGREEN. Results are presented as percent inhibition of SNCA, relative to untreated control cells. As illustrated in Table 5, SNCA mRNA levels were reduced in a dose-dependent manner in antisense oligonucleotide treated cells.

TABLE 5

| Dose-dependent antisense inhibition of human SNCA in SH-SY5Y cells | | | |
|---|---|---|---|
| Oligo ID | 5 μM | 10 μM | 20 μM |
| 387978 | 79 | 85 | 94 |
| 387984 | 79 | 92 | 96 |
| 387985 | 54 | 82 | 93 |
| 387986 | 63 | 84 | 91 |
| 388004 | 71 | 88 | 92 |

Example 4

Tolerability of Antisense Oligonucleotides Targeting Human SNCA in a Mouse Model ISIS oligonucleotides that demonstrated dose-dependent inhibition in the studies described herein in Examples 2 and 3 were evaluated for tolerability in a mouse model by monitoring changes in the levels of various metabolic markers in C57BL/6 mice.

Treatment

C57BL/6 mice were injected with 50 mg/kg of ISIS 387973, ISIS 387975, ISIS 387978, ISIS 387983, ISIS 387984, ISIS 387985, ISIS 387986, ISIS 388004, ISIS 388008, ISIS 388010, or ISIS 388041 administered subcutaneously twice a week for 3 weeks. A control group of mice was injected with phosphate buffered saline (PBS) administered subcutaneously twice a week for 3 weeks. Mice were sacrificed 48 hrs after receiving the last dose. Plasma was collected for further analysis.

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured at the end of the treatment period. The results presented in Table 6 indicate that liver transaminases were within normal parameters for all the ISIS oligonucleotides, except for ISIS 387986.

TABLE 6

| Effect of antisense oligonucleotide treatment on ALT and AST (IU/L) of C57BL/6 mice | | |
|---|---|---|
| | ALT | AST |
| PBS | 32 | 62 |
| ISIS 387973 | 37 | 65 |
| ISIS 387975 | 67 | 94 |
| ISIS 387978 | 33 | 51 |
| ISIS 387983 | 45 | 81 |
| ISIS 387984 | 60 | 75 |
| ISIS 387985 | 30 | 49 |
| ISIS 387986 | 780 | 384 |
| ISIS 388004 | 36 | 59 |
| ISIS 388008 | 48 | 66 |
| ISIS 388010 | 73 | 79 |
| ISIS 388041 | 61 | 90 |

Body and Organ Weights

The body weights of the mice, as well as liver, spleen and kidney weights were measured at the end of the study. All the weights measured were within 13% that of the corresponding weights in the PBS control. The results demonstrate that none of the ISIS oligonucleotides had any adverse effect on the overall health of the mice.

Example 5

Potency of Antisense Oligonucleotides Targeting Human SNCA in a Transgenic Mouse Model (SNCA PAC Mice)

The ISIS oligonucleotides were further evaluated for potency in the SNCA PAC (PAC-Tg(SNCA$^{WT}$) Snca$^{-/-}$) transgenic mouse model. These mice harbor a knockout Snca allele and a transgene encoding human SNCA under a PAC (P 1 artificial chromosome construct) promoter.

Treatment

Groups of 4 SNCA PAC mice each were injected with 100 μg of ISIS 387973, ISIS 387975, ISIS 387978, ISIS 387983, ISIS 387984, ISIS 387985, ISIS 388004, ISIS 388008, ISIS 388010, or ISIS 388041 administered via an intrastriatal bolus injection. A control group of mice was injected with phosphate buffered saline (PBS) administered via an intrastriatal bolus injection. Mice were sacrificed 2 weeks after receiving the injection. Brain tissue was collected for further analysis.

RNA Analysis

RNA was extracted from the striatal and cortical tissues of the brain for real-time PCR analysis of human SNCA mRNA. The results are presented in Table 7, and demonstrate that most of the ISIS oligonucleotides inhibit human SNCA mRNA significantly compared to the PBS control.

TABLE 7

| Percent inhibition of human SNCA mRNA in SNCA PAC mice compared to the PBS control | | |
|---|---|---|
| Oligo ID | Striatum | Cortex |
| 387973 | 99 | 92 |
| 387975 | 93 | 65 |
| 387978 | 39 | 69 |
| 387983 | 97 | 65 |
| 387984 | 90 | 78 |
| 387985 | 98 | 75 |
| 388004 | 98 | 54 |
| 388008 | 0 | 0 |
| 388010 | 0 | 15 |
| 388041 | 99 | 74 |

Example 6

Antisense Inhibition of Human SNCA in SH-SY5Y Cells by Oligonucleotides Designed by Microwalk Additional gapmers were designed targeting the region of the SNCA gene between the target sites of ISIS 387984 (start site 404 of SEQ ID NO: 1) and ISIS 387985 (start site 444 of SEQ ID NO: 1), which demonstrated significant inhibition of SNCA mRNA. These gapmers were designed by creating gapmers shifted by one nucleobase from each other (i.e. "microwalk") of the region between the two gapmers. The new antisense oligonucleotides were designed as 5-10-5 gapmers. These gapmers were tested in vitro. ISIS 387984 and ISIS 387985 were also included in the assay for comparison. Cultured SH-SY5Y cells at a density of 5,000 cells'per well were transfected using electroporation with 2,000 nM antisense oligonucleotide. After a treatment period of approximately 24 hours, RNA was isolated from the cells and SNCA mRNA levels were measured by quantitative real-time PCR. Two human primer probe set 672 (forward sequence TGGCAGAAGCAGCAGGAAA, designated herein as SEQ ID NO: 95; reverse sequence TCCTTGGTTTTGGAGCCTACA, designated herein as SEQ ID NO: 96; probe sequence CAAAAGAGGGTGTTCTC, designated herein as SEQ ID NO: 97) and primer probe set 673 (forward sequence GGAGCAGGGAGCATTGCA, designated herein as SEQ ID NO: 92; reverse sequence CCTTCTTCATTCTTGCCCAACT, designated herein as SEQ ID NO: 93; probe sequence CACTGGCTTTGTCAAAA, designated herein as SEQ ID NO: 94) were individually used to measure SNCA mRNA levels. SNCA mRNA levels were adjusted according to total RNA content, as measured by Cyclophilin levels. Results are presented as percent inhibition of SNCA, relative to untreated control cells. The results are presented in Table 8.

The 5-10-5 MOE gapmers are 20 nucleosides in length, wherein the central gap segment is comprised of ten 2'-deoxynucleotides and is flanked on both sides (in the 5' and 3' directions) by wings comprising five nucleosides each. The internucleoside linkages throughout each gapmer are phosphorothioate (P═S) linkages. All cytidine residues throughout each gapmer are 5-methylcytidines. "Target start site" indicates the 5'-most nucleoside to which the gapmer is targeted. "Target stop site" indicates the 3'-most nucleoside to which the gapmer is targeted. Each gapmer listed in Table 8 is targeted SEQ ID NO: 1 (GENBANK Accession No. NM_000345.3).

As shown in Table 8, several of the gapmers exhibited at least 50% inhibition, as measured by primer probe set 673, including ISIS numbers: 387984, 489351, 489352, 489353, 489354, 489355, 489356, 489357, 489358, 489359, 489360, 489361, 489362, 489364, 489365, 489366, 489367, 489368, 489369, 489371, 489372, 489373, 489374, 489375, 489381, 489382, 489383, 489387, and 387985.

Several of the gapmers exhibited at least 60% inhibition, including ISIS numbers: 387984, 489351, 489352, 489353, 489355, 489356, 489357, 489358, 489359, 489360, 489361, 489366, 489371, 489372, 489373, 489374, 489381, 489383, and 387985.

Several of the gapmers exhibited at least 70% inhibition, including ISIS numbers: 387984, 489351, 489352, 489356, 489357, 489358, 489359, 489360, 489361, 489373, 489374, 489381, and 387985.

Several of the gapmers exhibited at least 80% inhibition, including ISIS numbers: 489357, 489358, 489359, and 489360.

Two of the gapmers exhibited at least 85% inhibition, including ISIS numbers: 489357 and 489358.

One gapmer exhibited at least 90% inhibition, which is ISIS 489357.

TABLE 8

Inhibition of human SNCA mRNA levels by chimeric antisense oligonucleotides targeted to SEQ ID NO: 1

| Target Start Site | Target Stop Site | Oligo ID | Sequence | % inhibition (primer probe set 672) | % inhibition (primer probe set 673) | SEQ ID NO |
|---|---|---|---|---|---|---|
| 404 | 423 | 387984 | TTGCCACACCATGCACCACT | 79 | 76 | 22 |
| 405 | 424 | 489351 | GTTGCCACACCATGCACCAC | 81 | 76 | 98 |
| 406 | 425 | 489352 | TGTTGCCACACCATGCACCA | 75 | 70 | 99 |
| 407 | 426 | 489353 | CTGTTGCCACACCATGCACC | 70 | 64 | 100 |
| 408 | 427 | 489354 | ACTGTTGCCACACCATGCAC | 62 | 56 | 101 |
| 409 | 428 | 489355 | CACTGTTGCCACACCATGCA | 67 | 61 | 102 |
| 410 | 429 | 489356 | CCACTGTTGCCACACCATGC | 82 | 79 | 103 |
| 411 | 430 | 489357 | GCCACTGTTGCCACACCATG | 92 | 90 | 104 |
| 412 | 431 | 489358 | AGCCACTGTTGCCACACCAT | 90 | 87 | 105 |
| 413 | 432 | 489359 | CAGCCACTGTTGCCACACCA | 89 | 83 | 106 |
| 414 | 433 | 489360 | TCAGCCACTGTTGCCACACC | 88 | 84 | 107 |
| 415 | 434 | 489361 | CTCAGCCACTGTTGCCACAC | 83 | 76 | 108 |
| 416 | 435 | 489362 | TCTCAGCCACTGTTGCCACA | 64 | 57 | 109 |
| 417 | 436 | 489363 | TTCTCAGCCACTGTTGCCAC | 54 | 49 | 110 |
| 418 | 437 | 489364 | CTTCTCAGCCACTGTTGCCA | 65 | 59 | 111 |
| 419 | 438 | 489365 | TCTTCTCAGCCACTGTTGCC | 58 | 53 | 112 |
| 420 | 439 | 489366 | GTCTTCTCAGCCACTGTTGC | 68 | 64 | 113 |
| 421 | 440 | 489367 | GGTCTTCTCAGCCACTGTTG | 62 | 51 | 114 |
| 422 | 441 | 489368 | TGGTCTTCTCAGCCACTGTT | 61 | 54 | 115 |
| 423 | 442 | 489369 | TTGGTCTTCTCAGCCACTGT | 61 | 53 | 116 |
| 424 | 443 | 489370 | TTTGGTCTTCTCAGCCACTG | 55 | 49 | 117 |
| 425 | 444 | 489371 | CTTTGGTCTTCTCAGCCACT | 75 | 68 | 118 |
| 426 | 445 | 489372 | TCTTTGGTCTTCTCAGCCAC | 65 | 60 | 119 |
| 427 | 446 | 489373 | CTCTTTGGTCTTCTCAGCCA | 79 | 75 | 120 |
| 428 | 447 | 489374 | GCTCTTTGGTCTTCTCAGCC | 76 | 72 | 121 |
| 429 | 448 | 489375 | TGCTCTTTGGTCTTCTCAGC | 58 | 51 | 122 |
| 430 | 449 | 489376 | TTGCTCTTTGGTCTTCTCAG | 46 | 38 | 123 |
| 431 | 450 | 489377 | CTTGCTCTTTGGTCTTCTCA | 49 | 46 | 124 |
| 432 | 451 | 489378 | ACTTGCTCTTTGGTCTTCTC | 44 | 34 | 125 |
| 433 | 452 | 489379 | CACTTGCTCTTTGGTCTTCT | 46 | 35 | 126 |
| 434 | 453 | 489380 | TCACTTGCTCTTTGGTCTTC | 50 | 45 | 127 |

TABLE 8-continued

Inhibition of human SNCA mRNA levels by chimeric antisense oligonucleotides targeted to SEQ ID NO: 1

| Target Start Site | Target Stop Site | Oligo ID | Sequence | % inhibition (primer probe set 672) | % inhibition (primer probe set 673) | SEQ ID NO |
|---|---|---|---|---|---|---|
| 435 | 454 | 489381 | GTCACTTGCTCTTTGGTCTT | 80 | 73 | 128 |
| 436 | 455 | 489382 | TGTCACTTGCTCTTTGGTCT | 67 | 58 | 129 |
| 437 | 456 | 489383 | TTGTCACTTGCTCTTTGGTC | 70 | 65 | 130 |
| 438 | 457 | 489384 | TTTGTCACTTGCTCTTTGGT | 42 | 31 | 131 |
| 439 | 458 | 489385 | ATTTGTCACTTGCTCTTTGG | 54 | 43 | 132 |
| 440 | 459 | 489386 | CATTTGTCACTTGCTCTTTG | 42 | 38 | 133 |
| 441 | 460 | 489387 | ACATTTGTCACTTGCTCTTT | 58 | 50 | 134 |
| 442 | 461 | 489388 | AACATTTGTCACTTGCTCTT | 46 | 39 | 135 |
| 443 | 462 | 489389 | CAACATTTGTCACTTGCTCT | 59 | 49 | 136 |
| 444 | 463 | 387985 | CCAACATTTGTCACTTGCTC | 76 | 71 | 23 |

Example 7

Potency of Antisense Oligonucleotides Targeting Human SNCA in a Transgenic Mouse Model (SNCA PAC Mice)

The ISIS oligonucleotides that demonstrated significant inhibition in the study described herein in Example 6 were further evaluated for potency in SNCA PAC mice.

Treatment

Groups of 12 SNCA PAC mice each were injected with 50 μg of ISIS 387985, ISIS 489351, ISIS 489352, ISIS 489356, ISIS 489357, ISIS 489358, ISIS 489359, ISIS 489360, ISIS 489373, ISIS 489374, ISIS 489381, or ISIS 489383 administered via an intrastriatal bolus injection. A control group of mice was injected with phosphate buffered saline (PBS) administered via an intrastriatal bolus injection. Mice were sacrificed 2 weeks after receiving the injection. Brain tissue was collected for further analysis.

RNA Analysis

RNA was extracted from the hippocampal, striatal and cortical tissues of the brain for real-time PCR analysis of human SNCA mRNA using primer probe set 673 (described herein in Example 6 above). The results are presented in Table 9, and demonstrate that most of the ISIS oligonucleotides inhibit human SNCA mRNA significantly compared to the PBS control.

TABLE 9

Percent (%) inhibition of human SNCA mRNA in SNCA PAC mice compared to the PBS control

| Oligo ID | Cortex | Striatum | Hippocampus |
|---|---|---|---|
| 387985 | 86 | 76 | 72 |
| 489351 | 77 | 31 | 28 |
| 489352 | 81 | 38 | 54 |
| 489356 | 83 | 0 | 43 |
| 489357 | 91 | 49 | 76 |
| 489358 | 75 | 0 | 76 |
| 489359 | 81 | 62 | 65 |
| 489360 | 72 | 0 | 70 |

TABLE 9-continued

Percent (%) inhibition of human SNCA mRNA in SNCA PAC mice compared to the PBS control

| Oligo ID | Cortex | Striatum | Hippocampus |
|---|---|---|---|
| 489373 | 78 | 34 | 64 |
| 489374 | 77 | 53 | 82 |
| 489381 | 73 | 34 | 72 |
| 489383 | 59 | 61 | 34 |

Example 8

Potency of Antisense Oligonucleotides Targeting Human SNCA in a Transgenic Mouse Model (Thy1-aSYN Mice)

The ISIS oligonucleotides that demonstrated significant inhibition in the study described herein in Example 7 were further evaluated in Thy1-aSYN mice.

Treatment

Groups of 4 Thy1-aSYN mice each were injected with 50 μg of ISIS 387985, ISIS 489352, ISIS 489356, and ISIS 489357 administered via an intrastriatal bolus injection. Mice were anesthetized with sodium pentobarbitone (66 mg/kg Nembutal in sterile 0.9% saline, i.p.). The scalps of the mice were then shaved and, following loss of the pedal reflex, mice were placed in a stereotaxic frame (David Kopf Instruments, CA). To maintain a surgical plane of anesthesia, mice were administered with isoflurane (1-2% in 100% oxygen at 0.5 L/min) via a nose cone, as required. The scalp was sterilized using three alternating wipes of Betadine and 70% ethanol. An incision was made in the scalp and the skull surface exposed and bregma positively identified. A hole was drilled in the skull at 0.5 mm AP, 2 mm ML, relative to bregma. ISIS 387985, ISIS 489352, ISIS 489356, and ISIS 489357 at a dose of 50 μg in a 2 μL solution was injected unilaterally into the right striatum, using a 10 uL Hamilton syringe with a 27 gauge needle connected to a microsyringe pump controller (KD Scientific 310) at a flow rate of 0.2 uL/min. The DV coordinate was measured at 3 mm below the skull surface. The needle was left in place for a further 3 minutes after injection to allow diffusion of the solution into the brain. After slowly withdrawing the syringe, the scalp was sutured and mice were subcutaneously injected with 0.5 mL warm sterile saline to aid rehydration, and placed on a warm water heat pad and monitored until they regained consciousness and mobility. A group of 4 mice was injected with PBS in a similar manner. Mice were returned to their home cage and supplied with mashed food on the cage floor. The body weights and health of mice was monitored daily post-surgery. Mice were sacrificed 2 weeks after receiving the injection. Brain tissue was collected for further analysis. A group of 4 mice was injected with PBS in a similar manner.

RNA Analysis

RNA was extracted from the striatal and cortical tissues of the brain for real-time PCR analysis of human SNCA mRNA normalized to Cyclophilin A mRNA. The results are presented in Table 10.

TABLE 10

Percent inhibition of human SNCA mRNA in Thy1-aSYN mice compared to the PBS control

| Oligo ID | Cortex | Striatum |
|---|---|---|
| 387985 | 67 | 63 |
| 489352 | 50 | 18 |
| 489356 | 56 | 20 |
| 489357 | 64 | 53 |

Protein Analysis

Protein was extracted from cell lysates of the striatal and cortical tissues of the brain and quantified by western blot analysis using anti-alpha-synuclein, clone Syn211 (Millipore, NY). The results were normalized to alpha-tubulin and are presented in Table 11.

TABLE 11

Percent inhibition of human SNCA protein levels in Thy1-aSYN mice compared to the PBS control

| Oligo ID | Cortex | Striatum |
|---|---|---|
| 387985 | 24 | 37 |
| 489352 | 30 | 51 |
| 489356 | 0 | 66 |
| 489357 | 0 | 78 |

Quantification of Antisense Oligonucleotide Levels in Brain Sections

The rostral and caudal regions of striatal and cortical tissues of the brain were individually stained using immunofluoresent antibodies against the antisense oligonucleotides (Ab6653, ISIS Pharmaceuticals, CA) or mouse anti-SNCA (BD Transduction Laboratories, CA). Images of the stained sections were acquired using a microarray scanner (Agilent Technologies, CA). Immunofluorescent intensity was quantified using ImageJ (NIH). The results of the quantification of immunofluoresence are presented in Tables 12 and 13. The results from Table 12 demonstrate the even distribution of the antisense oligonucleotides to different regions of the brain, relative to the PBS control level, which was designated zero intensity. Table 13 presents the SNCA protein levels in the corresponding brain sections, and demonstrates inhibition of SNCA by some of the ISIS oligonucleotides.

TABLE 12

Antisense oligonucleotide levels in Thy1-aSYN mice compared to the PBS control (arbitrary units)

| Oligo ID | Cortex (rostral) | Striatum (rostral) | Cortex (caudal) | Striatum (caudal) |
|---|---|---|---|---|
| 387985 | 22607 | 25225 | 29899 | 34625 |
| 489352 | 34604 | 30315 | 32535 | 36067 |
| 489356 | 26615 | 22943 | 26549 | 24441 |
| 489357 | 25219 | 25095 | 27427 | 30458 |

TABLE 13

Percent reduction in SNCA levels in Thy1-aSYN mice compared to the PBS control

| Oligo ID | Cortex (rostral) | Striatum (rostral) | Cortex (caudal) | Striatum (caudal) |
|---|---|---|---|---|
| 387985 | 17 | 23 | 37 | 16 |
| 489352 | 14 | 12 | 28 | 10 |
| 489356 | 0 | 0 | 0 | 0 |
| 489357 | 0 | 0 | 21 | 0 |

Evaluation of Toxicity Due to Antisense Oligonucleotide Administration in Brain Sections The rostral and caudal regions of striatal and cortical tissues of the brain were also individually stained with immunofluorescent antibodies rabbit anti-GFAP (Dako Inc, CA) or anti-NeuN (Chemicon Inc). Images of the stained sections were acquired using a microarray scanner (Agilent Technologies, CA). Immunofluorescent intensity was quantified using ImageJ (NIH). The results of the quantification are presented in Tables 14 and 15. Table 14 shows the levels of glial fibrillary acidic protein (GFAP), which is moderately increased in a non-specific manner as a result of antisense oligonucleotide administration. This is an expected outcome (Chiasson et al., *Cell. Mol. Neurobiol.* 1994. 14: 507-521) and the results demonstrate that the increase is non-significant. Table 15 presents the data on NeuN, a neuron marker that indicates neuronal toxicity. The results indicate none of the ISIS oligonucleotides induced increase in NeuN levels relative to the PBS control.

The brain sections were separately stained with rabbit anti-Ibal (Wako Chem. Inc, CA) to detect microglial cells, followed by probing with a biotinylated secondary antibody. The sections were developed using a complex of avidin-biotin peroxidase. The sections were then developed by DAB substrate. The optical fractionator function of Stereo Investigator (MicroBrightField) was used to count 4 representative samples of Ibal-positive microglial cells in the striatum and cortex. The microglia were then scored as either resting or activated microglia. The scoring was based on morphological criteria of either ramified (resting) or amoeboid (activated) appearance. Activated microglia are a marker of neuronal toxicity. The average of the results was expressed as a percent of the number of activated Ibal-positive cells compared to the total number of Ibal-positive cells. The results are presented in Table 18, and demonstrate that treatment with either ISIS 387985 or ISIS 489357 does not cause microglial activation. Hence, treatment with either antisense oligonucleotide did not cause any neural toxicity.

TABLE 14

| Percent increase in GFAP levels in Thy1-aSYN mice compared to the PBS control | | |
|---|---|---|
| Oligo ID | Cortex (caudal) | Striatum (caudal) |
| 387985 | 70 | 128 |
| 489352 | 66 | 151 |
| 489356 | 61 | 82 |
| 489357 | 120 | 130 |

TABLE 15

| Percent change in NeuN levels in Thy1-aSYN mice compared to the PBS control | | |
|---|---|---|
| Oligo ID | Cortex (caudal) | Striatum (caudal) |
| 387985 | −11 | −11 |
| 489352 | −28 | −38 |
| 489356 | −5 | −1 |
| 489357 | −10 | −15 |

TABLE 16

| Percent of activated microglia in Thy1-aSYN mice | | |
|---|---|---|
| | Cortex | Striatum |
| PBS | 7 | 19 |
| ISIS 387985 | 26 | 27 |
| ISIS 489352 | 43 | 49 |
| ISIS 489356 | 35 | 66 |
| ISIS 489357 | 21 | 37 |

Example 9

Potency of Antisense Oligonucleotides Targeting Human SNCA in a Transgenic Mouse Model (Thy1-aSYN Mice)

Some of the ISIS oligonucleotides from the study described herein in Example 5 were further evaluated in Thy1-aSYN mice, which overexpress human SNCA (Rockenstein et al., J. Neurosci. Res. 68: 568-578, 2002). ISIS 387978, ISIS 387983, ISIS 387984, and ISIS 387985 all target the transgene mRNA in Thy-aSYN mice and were tested in this model.

The target sites of the human oligonucleotides to the human mRNA sequence, SEQ ID NO: 1 (GENBANK Accession No. NM_000345.3) are presented in Table 17. Some of the human oligonucleotides are cross-reactive with mouse SNCA sequences. The greater the complementarity between the human oligonucleotide and the murine sequence, the more likely the human oligonucleotide can cross-react with the murine sequence. The target start sites of the human oligonucleotides to the murine sequence SEQ ID NO: 137 (GENBANK Accession No NM_001042451.1) are also presented in Table 17. 'n/a' indicates that the antisense oligonucleotide has more than 3 mismatches to the murine sequence.

TABLE 17

| Target Start Sites of antisense oligonucleotides targeting SEQ ID NO: 1 and SEQ ID NO: 137 | | | |
|---|---|---|---|
| Human Target Start Site | ISIS No | Murine Target Start Site | SEQ ID NO |
| 282 | 387978 | 318 | 16 |
| 381 | 387983 | n/a | 20 |
| 404 | 387984 | n/a | 22 |
| 444 | 387985 | 480 | 23 |

Treatment

Groups of 4 Thy1-aSYN mice each were injected with 50 μg of ISIS 387978, ISIS 387983, ISIS 387984, or ISIS 387985, administered via intrastriatal bolus injection. Mice were anesthetized with sodium pentobarbitone (66 mg/kg Nembutal in sterile 0.9% saline, i.p.). The scalps of the mice were then shaved and, following loss of the pedal reflex, mice were placed in a stereotaxic frame (David Kopf Instruments, CA). To maintain a surgical plane of anesthesia, mice were administered with isoflurane (1-2% in 100% oxygen at 0.5 L/min) via a nose cone, as required. Oxygen was administered throughout the surgery and for 30 min post-surgically. The temperature of the mice was monitored using a rectal probe thermometer (Physitemp). The scalp was sterilized using three alternating wipes of Betadine and 70% ethanol. An incision was made in the scalp and the skull surface exposed and bregma positively identified. After ensuring that the skull surface was flat, i.e. a dorsoventral (DV) deviation of <0.2 mm at bregma +/−2 mm antero-posterior (AP), a hole was drilled in the skull at 0.5 mm AP, 2 mm medialateral (ML), relative to bregma. Each of the ISIS oligonucleotides at a concentration of 50 mg/mL in a 2 μL solution was injected unilaterally into the right striatum, using a 10 μL Hamilton syringe with a 27 gauge needle connected to a microsyringe pump controller (KD Scientific 310) at a flow rate of 0.2 μL/min. The DV coordinate was measured at 3 mm below the skull surface. The needle was left in place for a further 3 minutes after injection to allow diffusion of the solution into the brain. After slowly withdrawing the syringe, the scalp was sutured, and the mice were subcutaneously injected with 0.5 mL warm sterile PBS, to aid rehydration. The mice were placed on a warm water heat pad and monitored until they regained consciousness and mobility. A group of 4 mice was injected with PBS in a similar manner. The animals were then returned to their home cage and supplied with mashed food on the cage floor. The body weights and health of mice was monitored daily post-surgery. Mice were sacrificed 2 weeks after receiving the injection by cervical dislocation.

The brains of the mice were immediately collected and dissected. Using a coronal brain matrix, 1 mm slices of the brain were harvested for mRNA and protein extraction. A 1 mm slice immediately rostral to the injection site was taken for mRNA and a 1 mm slice immediately caudal to the injection site was taken for protein analyses. The striatum and cortex from the ipsilateral hemisphere were dissected on ice.

RNA Analysis

For mRNA purification, brain tissue was rapidly frozen on dry ice in 2 mL tubes containing 0.5 mL GITC/BME and sterile ceramic beads. RNA was extracted from the striatal and cortical tissues of the brain for real-time PCR analysis of human SNCA mRNA normalized to Cyclophilin A mRNA. Human SNCA mRNA levels were measured using human primer probe set RTS2618 (forward sequence AGACCAAAGAGCAAGTGACAAATG, designated herein as SEQ ID NO: 138; reverse sequence CCTCCACT-GTCTTCTGGGCTACT, designated herein as SEQ ID NO: 139; probe sequence TGGAGGAGCAGTGGT-GACGGGTG, designated as SEQ ID NO: 140). The results are presented in Table 18, expressed as percent inhibition compared to the PBS control. Mouse SNCA mRNA levels were also measured using murine primer probe set RTS2956 (forward sequence GTCATTGCACCCAATCTCCTAAG, designated herein as SEQ ID NO: 141; reverse sequence GACTGGGCACATTGGAACTGA, designated herein as SEQ ID NO: 142; probe sequence CGGCTGCTCTTC-CATGGCGTACAA, designated herein as SEQ ID NO: 143). The results are presented in Table 19, expressed as percent inhibition compared to the PBS control. Since ISIS 387978 and ISIS 387985 both target SEQ ID NO: 137, treatment with either antisense oligonucleotide inhibits murine SNCA mRNA expression.

TABLE 18

Percent inhibition of human SNCA mRNA in Thy1-aSYN mice compared to the PBS control

| ISIS No | Striatum | Cortex |
|---|---|---|
| 387978 | 35 | 0 |
| 387983 | 16 | 0 |
| 387984 | 67 | 35 |
| 387985 | 89 | 70 |

TABLE 19

Percent inhibition of murine SNCA mRNA in Thy1-aSYN mice compared to the PBS control

| ISIS No | Striatum | Cortex |
|---|---|---|
| 387978 | 62 | 44 |
| 387983 | 16 | 0 |
| 387984 | 18 | 2 |
| 387985 | 84 | 83 |

Protein Analysis

Tissue samples for protein analysis were rapidly frozen in tubes containing sterile ceramic beads. Protein levels of SNCA were measured by western blot analysis using an anti-SNCA antibody (Signet, #4D6) targeting both human and murine SNCA. The results are presented in Table 20, expressed as percent inhibition compared to the PBS control.

TABLE 20

Percent inhibition of SNCA protein levels in Thy1-aSYN mice compared to the PBS control

| ISIS No | Striatum | Cortex |
|---|---|---|
| 387978 | 0 | 0 |
| 387983 | 9 | 0 |
| 387984 | 0 | 0 |
| 387985 | 29 | 76 |

Immunofluorescence Analysis

One coronal section from each brain was taken at the level of the caudal striatum. After washing in PBS, the sections were incubated in M.O.M. mouse IgG blocking reagent (Vector Laboratories, PK-2200) for 1 hour. Sections were then incubated overnight at 4° C. in 2% NGS, 0.5% Triton X-100 in PBS with primary antibodies, mouse anti-NeuN (1:500 dilution; Chemicon MAB377) and 6653Ab rabbit anti-ASO (1:3,000 dilution; ISIS Pharmaceuticals). After washing in PBS, the sections were incubated for 2 hours in 5% NGS in PBS with secondary antibodies, Cy3-conjugated goat anti-rabbit (1:250 dilution; Millipore) and Cy5-conjugated goat anti-mouse (1:250 dilution; Jackson Immunoresearch). Several sections were incubated with secondary antibodies alone, omitting primary antibody incubation, to serve as controls. After washing in PBS, sections were mounted onto glass microscope slides in water and dried overnight. Slides were scanned using a high-resolution microarray scanner (Agilent) using lasers to excite the Cy3 and Cy5 fluorochromes. The images of the scanned sections were then analyzed using ImageJ (NIH) to quantify the intensity of the immunofluorescent staining. The average intensity of staining in the striatum and cortex of the ipsilateral and contralateral hemispheres from the brains of mice receiving ASOs was calculated and compared to that of the control mice. The immunofluorescence intensity of the PBS control was considered the baseline and was arbitrarily designated as 1.00. The results are presented in Table 21 and indicate that there was negligible neuronal toxicity in most of the ISIS oligonucleotides tested.

TABLE 21

NeuN quantification by immunofluorescent intensity in the striatum and cortex

| | Striatum | Cortex |
|---|---|---|
| PBS | 1.00 | 1.00 |
| 387978 | 0.47 | 0.85 |
| 387983 | 0.77 | 1.17 |
| 387984 | 0.78 | 1.02 |
| 387985 | 0.90 | 0.96 |

The distribution of ASO, as displayed by Ab6653 staining, was widespread throughout the ipsilateral hemisphere, including the striatum and cortex, extending along the entire rostral-caudal axis of the striatum. Other brain structures, including the globus pallidus, the rostral extent of the hippocampus and the thalamus, were also immunopositive.

Example 10

Effect on Behavior of Thy1-aSYN Mice after Administration of Antisense Oligonucleotides Targeting Human SNCA ISIS 387985, which demonstrated significant potency in the studies described above is administered to Thy1-aSYN mice. Motor function, olfaction, and spatial memory are tested in the mice.

Treatment

Groups of 16 male Thy1-aSYN mice each, 3.5 months in age, are infused ICV, using Alzet minipump model #2002 with brain infusion kit, with 50 μg/day of ISIS 387985 or with sterile PBS for 2 weeks. This is followed by 2 weeks washout, wherein the minipump is removed and mice are allowed to recover. The mice are tested behaviorally between 4.5 months and 5 months of age. The tests used to analyze behavior are a motor test, which includes a challenging beam and pole task (Fleming, S. M. et al., J. Neurosci. 24: 9434-9440, 2004), an olfaction test using a buried pellet (Fleming, S. M. et al., Eur. J. Neurosci. 28: 247-256, 2008), and a spatial working memory test using novel place recognition (Magen et al., submitted). Mice are euthanized at 5 months of age. The brain and peripheral tissues are harvested for biochemical and histological analysis.

What is claimed is:

1. A modified, single-stranded oligonucleotide consisting of 12 to 30 linked nucleosides comprising a nucleobase sequence that is complementary to at least 8 contiguous nucleobases of nucleobases 236-301 of SEQ ID NO: 1; and wherein the nucleobase sequence of the modified oligonucleotide is at least 90% complementary to SEQ ID NO: 1 and wherein at least one nucleoside of the modified oligonucleotide comprises a 5-methylcytosine.

2. The modified oligonucleotide of claim 1, wherein the modified oligonucleotide has a nucleobase sequence that is 100% complementary to SEQ ID NO: 1.

3. The modified oligonucleotide of claim 1, wherein the modified oligonucleotide comprises at least one modified internucleoside linkage.

4. The modified oligonucleotide of claim 3, wherein at least one modified internucleoside linkage is a phosphorothioate internucleoside linkage.

5. The modified oligonucleotide of claim 1, wherein at least one nucleoside of the modified oligonucleotide comprises a modified sugar.

6. The modified oligonucleotide of claim 5, wherein the modified sugar is a bicyclic sugar.

7. The modified oligonucleotide of claim 6, wherein the bicyclic sugar comprises a 4'-$CH(CH_3)$—O-2' bridge.

8. The modified oligonucleotide of claim 5, comprising at least one tetrahydropyran modified nucleoside wherein a tetrahydropyran ring replaces the furanose ring.

9. The modified oligonucleotide of claim 8, wherein each of the at least one tetrahydropyran modified nucleoside has the structure:

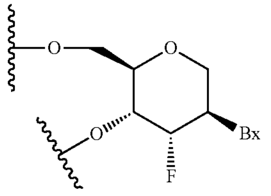

wherein Bx is an optionally protected heterocyclic base moiety.

10. The modified oligonucleotide of claim 5, wherein the modified sugar comprises a 2'-O-methoxyethyl group.

11. The modified oligonucleotide of claim 1, wherein the modified oligonucleotide comprises:

a gap segment consisting of linked deoxy nucleosides;

a 5' wing segment consisting of linked nucleosides;

a 3' wing segment consisting of linked nucleosides;

wherein the gap segment is positioned between the 5' wing segment and the 3' wing segment, wherein each nucleoside of each wing segment comprises a modified sugar.

12. The modified oligonucleotide of claim 11, wherein the modified oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5-methylcytosine.

13. A compound comprising a single-stranded modified oligonucleotide consisting of at least 12 contiguous nucleobases of a nucleobase sequence selected from among the nucleobase sequences recited in SEQ ID Nos: 11-16, wherein at least one nucleoside of the modified oligonucleotide comprises a 5-methylcytosine.

14. The modified oligonucleotide of claim 1, wherein the nucleobase sequence comprises a nucleobase sequence selected from among the nucleobase sequences recited in SEQ ID Nos: 11-16.

15. The modified oligonucleotide of claim 1, wherein the nucleobase sequence consists of a nucleobase sequence selected from among the nucleobase sequences recited in SEQ ID Nos: 11-16.

* * * * *